(12) United States Patent
Pribish et al.

(10) Patent No.: US 6,365,597 B1
(45) Date of Patent: *Apr. 2, 2002

(54) 4-AZA STEROIDS

(75) Inventors: James R. Pribish, Sharonville; Cynthia A. Gates, Fairfield; Philip M. Weintraub, Cincinnati, all of OH (US)

(73) Assignee: Aventis Pharmaceuticals Inc., Bridgewater, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/798,258

(22) Filed: Feb. 11, 1997

Related U.S. Application Data
(60) Provisional application No. 60/046,877, filed on Feb. 14, 1996.

(51) Int. Cl.$^7$ .................. A61K 31/44; C07D 221/18; C07D 221/22; A61P 17/10
(52) U.S. Cl. ............... 514/284; 546/77; 546/78
(58) Field of Search .............. 546/77, 78; 514/284

(56) References Cited

U.S. PATENT DOCUMENTS

| | | | |
|---|---|---|---|
| 4,009,208 A | * 2/1977 | Lesher | 260/559 |
| 4,347,245 A | * 8/1982 | Shapiro | 514/175 |
| 4,757,061 A | 7/1988 | Faustini et al. | 514/177 |
| 4,859,681 A | 8/1989 | Rasmusson et al. | 514/284 |
| 4,888,336 A | * 12/1989 | Holt et al. | 514/278 |
| 4,891,367 A | 1/1990 | Angelastro et al. | 514/178 |
| 4,966,897 A | 10/1990 | Angelastro et al. | 514/177 |
| 4,966,898 A | 10/1990 | Angelastro et al. | 514/182 |
| 5,075,464 A | 12/1991 | Blohm et al. | 552/522 |
| 5,116,983 A | 5/1992 | Bhattacharya et al. | 546/14 |
| 5,120,840 A | 6/1992 | Weintraub et al. | 540/94 |
| 5,143,909 A | 9/1992 | Weintraub et al. | 514/177 |
| 5,151,429 A | 9/1992 | Rasmusson et al. | 514/284 |
| 5,180,711 A | * 1/1993 | Hodgen | 514/15 |
| 5,359,071 A | 10/1994 | Durette et al. | 546/78 |
| 5,486,511 A | 1/1996 | Weintraub et al. | 514/178 |
| 5,536,727 A | 7/1996 | Witzel et al. | 514/284 |

FOREIGN PATENT DOCUMENTS

| | | |
|---|---|---|
| EP | 0428366 | 11/1990 |
| EP | 0473225 | 8/1991 |
| EP | 0473226 | 8/1991 |
| WO | 9315104 | 8/1993 |
| WO | 9323039 | 11/1993 |
| WO | 9323053 | 11/1993 |
| WO | 9323420 | 11/1993 |
| WO | 9420104 | 9/1994 |
| WO | 9428010 | 12/1994 |

OTHER PUBLICATIONS

Bhattacharya et al, Silyation–Mediated Oxidation of 4–Aza–3–ketosteroids with DDQ Proceeds via DDQ–Substrate Adducts, J. Am. chem. Soc. 110:3318–3319, (1988).
Milewich et al, 17β–Hydroxy–5–Oxo–3, 5–seco–4–Norandrostane–3–Carboxylic Acid, Organic Syntheses vol. 6, 690–691, 1988.
Bohlmann, A New Route to Seroidal Vinyl Fluorides, Tetrahedron Ltrs, 35 (1):85–88, (1994).
Klinik et al., Steroid biosynthesis inhibitors of Cushing's syndrome, Clin. Investig., 72:481–488 (1994).
Raamunson, et al., Azasteroids: Structure–Activity Relationships for Inhibition of 5α–Reductase and of Androgen Receptor Binding, J. Med. Chem., 29:2296–2315 (1986).
Xun et al., J. Med. Chem., 38, 1158–1173 (1995).

* cited by examiner

Primary Examiner—Richard L. Raymond
Assistant Examiner—Brenda Coleman
(74) Attorney, Agent, or Firm—Lawrence L. Martin; Barbara E. Kurys; J. Michael Dixon

(57) ABSTRACT

The invention related to 4-aza-17β-(cyclopropoxy)-androst-5α-androstan-3-one, 4-aza-17β-(cyclopropylamino)-androst-4-en-3-one and related compounds and to compositions incorporating these compounds, as well as the inhibition of $C_{17-20}$ lyase, 5α-reductase and $C_{17α}$-hydroxylase and to the use of these compounds in the treatment of androgen and estrogen mediated disorders, including benign prostatic hyperplasia, androgen mediated prostate cancer, estrogen mediated breast cancer and to DHT-mediated disorders such as acne. Disorders relating to the oversynthesis of cortisol, for example, Cushing's Syndrome, are also included. The treatment of androgen-dependent disorders also includes a combination therapy with known androgen-receptor antagonists, such as flutamide. The compounds of the invention have the following general formula:

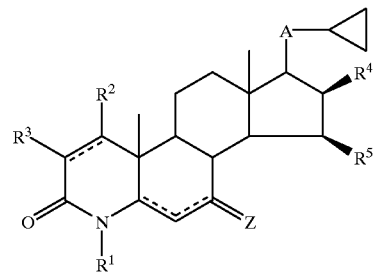

10 Claims, 10 Drawing Sheets

4-AZA STEROIDS

This application claims the benefit of U.S. Provisional Application No. 60/046,877, filed Feb. 14, 1996.

BACKGROUND OF THE INVENTION

The enzyme steroid $C_{17,20}$ lyase cleaves the 17–20 carbon-carbon bond in steroids having a two carbon side chain at the 17β-carbon position to form important precursor molecules to the formation of testosterone, 5α-dihydrotestosterone and the estrogens, principally estrone and estradiol. Compounds which inhibit this enzyme would thus serve to inhibit the formation of the indicated precursors and thereby be useful in the treatment of various androgenic as well as estrogenic disorders. A treatment incorporating such enzymatic inhibitors is not limited to the origin of the precursor molecule, such as various organ ablation techniques which are currently known. For example, while orchiectomy will effectively reduce gonadal androgen, it will have not have significant effect upon adrenal androgen production. Moreover, such an enzymatic treatment is a much more focused treatment in that it is directed to the immediate hormonal imbalance believed responsible for the condition, as opposed to a broad spectrum remedy which not only affects the particular symptom, but causes permanent endocrine defects necessitating lifelong dependency on replacement therapy.

It is further known that certain types of breast cancers are estrogen dependent. Adrenalectomy, ovariectomy and hypophysectomy have been employed as well as non-surgical techniques resulting in tumor regressions. It has been shown that human patients with advanced breast cancer, who are administered estrogen biosynthesis enzyme inhibitors, show dramatically reduced plasma estradiol levels and improved therapeutic effects, at least as effective as adrenalectomy. (Jean Van Wauve and Paul A. J. Janssen, *Journal of Medicinal Chemistry*, 32, 10:2231–2239).

Prostatic cancer, or neoplastic tissue disorders which originate in the parenchymal epithelium of the prostate is one of the most common malignancies among men, and exhibits one of the highest cancer-specific deaths of all malignant carcinomas. It is known that patients with metastatic prostate cancer respond positively to hormonal therapy. It is reported by Cookson and Sarosdy that androgen ablation has had a positive, beneficial response for as high as 60% to 80% for all patients tested. (Cookson C. S. and Sarosdy, M. F., South Med. J 87:1–6).

More specifically, $C_{17,20}$ lyase inhibitors would be useful in the treatment of hormonal dependent prostatic carcinoma, prostatic hyperplasia, virilism, congenital adrenal hyperplasia due to 21-hydroxylase deficiency, hirsutism, hormonal dependent breast cancer, polycystic ovarian syndrome correlated with elevated $C_{17,21}$ lyase activity as well as other neoplastic tissue disorders such as endometrial, hepatocellular and adrenal carcinomas.

The enzyme steroid 5α-reductase, present in mammalian tissues including skin, male genitalia and the prostate, catalyzes the conversion of testosterone (17β-hydroxy-androstan-4-en-3-one) into dihydrotestosterone or DHT (17β-hydroxy-5α-androst-3-one), which is also known as stanolone. DHT is a more potent androgen than testosterone, and acts as an end-organ effecter in certain tissues, particularly in mediating growth. DHT formation can occur in certain tissues themselves by the action of 5α-reductase. In the treatment of androgen dependent disorders, such as benign prostatic hyperplasia and prostatic cancer, including hormonal dependent carcinoma, the inhibition of DHT would be highly desirable.

The conversion of testosterone to DHT itself can be associated with various androgenic disorders, especially when DHT levels build up to excessive amounts. For example, high levels of DHT in the skin has been associated in the pathogenesis of acne, including acne vulgaris.

Agents which have the ability to inhibit both $C_{17-20}$ lyase and 5α-reductase would not only inhibit DHT production, but also testosterone formation. In inhibiting the principal androgenic steroidal hormones, such compounds would have enhanced utility in the treatment of androgen disorders.

The enzyme $C_{17}$-hydroxylase catalyzes the $C_{17}$ hydration of steroid substrates during the biosynthesis of cortisol. As $C_{17-20}$ lyase and $C_{17}$-hydroxylase are different active sites of the same enzyme, the inhibition of one usually results in the disabling of the other. Cortisol excess results in a syndrome characterized by hypokalemia, metabolic alkalosis, polydipsia, polyuria, Cushing's syndrome and hypertensive conditions. Inhibition of cortisol synthesis via $C_{17}α$-hydroxylase would therefor have therapeutic effect for the treatment of these disorders or conditions.

SUMMARY OF THE INVENTION

The present invention relates to 4-aza-17-(cyclopropoxy)-androst-5α-androstan-3-one, 4-aza-17-(cyclopropylamino)-androst-4-en-3-one and related compounds and to compositions incorporating these compounds, as well as the use of these compounds in the treatment of conditions which would be affected by inhibition of $C_{17-20}$ lyase and/or 5α-reductase, including androgen and estrogen ediated disorders, such as, for example benign prostatic hyperplasia, DHT-mediated disorders, such as, for example, acne, estrogen dependent breast cancer and androgen mediated prostatic cancer. As the present compounds also disable the operation of $C_{17α}$-hydroxylase, disorders which are characterized by an oversynthesis of cortisol can also be treated by the compounds of the invention. For example, hypokalemia, metabolic alkalosis, polydipsia, polyuria, Cushing's syndrome and hypertensive conditions.

In another embodiment, the compounds of the invention may be administered in combination with other effective treatment for enhanced therapeutic effect. For example, in the treatment of androgen-dependent disorders, including prostatic cancer, flutamide, a known androgen receptor antagonist may be used in combination with the compounds of the invention.

More particularly, the present invention is directed to a group of compounds, and to their pharmaceutically acceptable salts, having the following general formula:

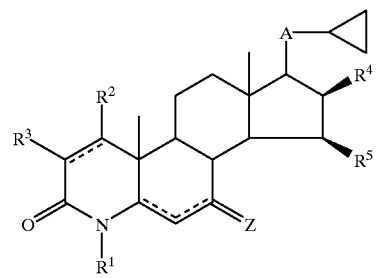

wherein:
A is O or NH;
$R^1$ is H or $C_{1-4}$ alkyl;

$R^2$ is halo, phenylthio, phenylsulfinyl or phenylsulfonyl;

$R^3$ is halo, $C_{1-4}$ alkylthio, $C_{1-4}$ alkylsulfinyl or $C_{1-4}$ alkylsulfonyl;

$R^4$ is H, $C_{1-4}$ alkyl or $C_{2-4}$ alkenyl;

$R^5$ is H, $C_{1-4}$ alkyl;

Z can be:
   a) oxo;
   b) (H)(H) or an a-hydrogen and a β-substituent selected from the group consisting of: $C_{1-4}$ alkyl, $C_{2-4}$ alkenyl, hydroxy, $C_{1-4}$ alkanoyloxy, $C_{1-4}$ alkoxycarbonylmethyl, carboxymethyl, $C_{1-4}$ alkoxycarbonyl, carboxy, $C_{1-4}$ alkanoyl and halo;

with the proviso that when:
   a) $R^2$ is present and is other than hydrogen, a 1,2-double bond is present, and
   b) Z is oxo a 6,7, double bond is not present.

DETAILED DESCRIPTION OF THE INVENTION

Figure 1:
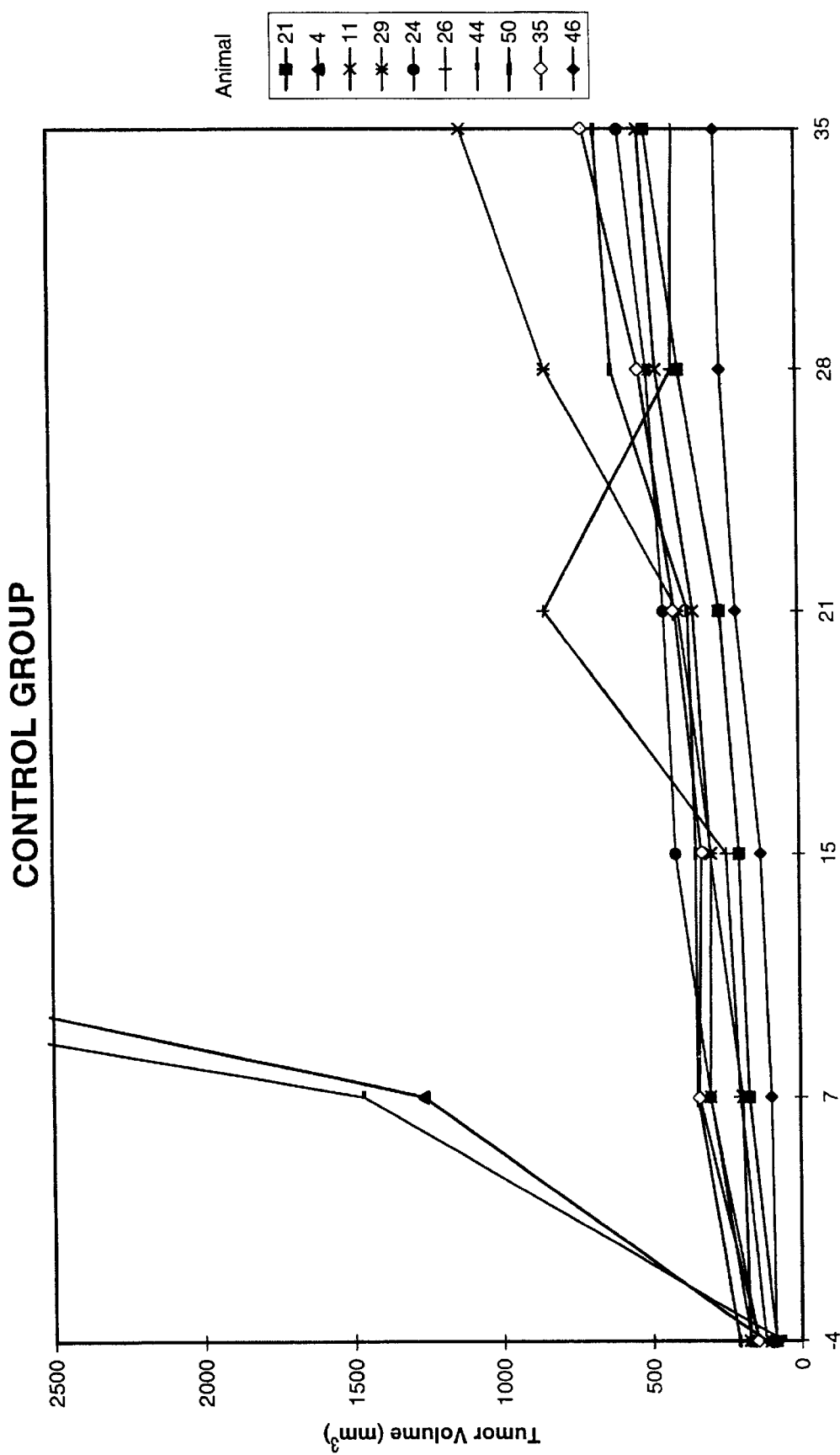
FIG. 1 Illustrates the tumor volume for individual animals over time of the vehicle control group in PC-82 nude mouse assay.

As used herein, the term "$C_{1-4}$ alkyl" means any straight or branched chain alkyl radical of one to four carbon atoms. For example, methyl, ethyl, n-propyl, isopropyl, n-butyl, sec-butyl, tert-butyl and the like.

As used herein, the term "$C_{2-4}$ alkenyl" means any straight or branched chain alkene radical of two to four carbon atoms. For example, ethenyl, vinyl, allyl, 1-propenyl, isopropenyl, 1-butenyl, 2-butenyl, 3-butenyl, 1,3-butenyl and the like.

As used herein, the term "$C_{1-4}$ alkylthio, $C_{1-4}$ alkylsulfinyl or $C_{1-4}$ alkylsulfonyl" means $C_{1-4}$ alkyl-Y-, where $C_{1-4}$ alkyl is as defined above, and Y is S, SO or $SO_2$ radical, respectively, and as depicted in Scheme G. "Phenylthio, phenylsulfinyl or phenylsulfonyl" is defined in a similar manner, or Ph—S—, Ph—SO— or Ph—$SO_2$—.

As used herein, the term "$C_{1-4}$ alkanoyloxy" defines a final product molecule which is the ester condensation product of the corresponding steroid alcohol with a straight or branched chain unsaturated carboxylic acid of from one to four carbon atoms. For example, formyloxy, acetyloxy, n-proprionyloxy, isoproprionyloxy, n-butanoyloxy, s-butanoyloxy, t-butanoyloxy and the like. It is graphically represented by compound 49 in Scheme I or compound 56 of Scheme J.

As used herein, the term "$C_{1-4}$ alkoxycarbonylmethyl" means a $C_{1-4}$ alkyl, as defined above, ester of acetic acid, all of which forms a substituent bonded at the α-carbonyl carbon to the steroid nucleus, as represented in Scheme K.

As used herein, the term "$C_{1-4}$-alkoxycarbonyl" means $C_{1-4}$ alkyl, as defined above, ester of formic acid, all of which forms a substituent bonded at the carbonyl carbon to the steroid nucleus, as represented in Scheme L.

As used herein, the term "$C_{1-4}$ alkanoyl" means a ketone of from one to four carbon atoms, bonded to the steroid nucleus at the carbonyl carbon, as represented in Scheme M. or example, ethanoyl, isopropanoyl, n-butanoyl, s-butanoyl, t-butanoyl.

As used herein, the term "halo" means a chloro, bromo or iodo substituent.

As used herein, the term "pharmaceutically acceptable salt" is intended to mean any organic or inorganic acid salt which is capable of forming a non-toxic acid addition salt which is suitable for use as a pharmaceutical. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di- and tri-carboxylic acids. For example, acetic, glycolic, lactic, pyruvic, malonic, succinic, glutaric, fumaric, malic, tartaric, citric, ascorbic, maleic, hydroxymaleic, hydroxybenzoic, phenylacetic, cinnamic, salicylic, glutamic, gluconic, formic and sulfonic acids such as methane sulfonic acid and 2-hydroxyethane sulfonic acid. Further examples of suitable pharmaceutically-acceptable salts are recited in Berge, S. M. et al, *J. Pharm Sci.* 66:1, 1 (1977), which is herein incorporated by reference. Such salts can exist in either a hydrated or substantially anhydrous form.

As used herein, the term "patient" refers to a warm blooded animal such as a mammal which is afflicted with a particular disease. It is explicitly understood that guinea pigs, dogs, cats, rats, mice, horses, cattle, sheep and humans are example of animals within the scope of the meaning of the term.

As used herein, the term "effective inhibitory amount", is such an amount wherein an enzyme inhibitory effect is achieved sufficient to cause a therapeutic effect in the patient. The exact amount of compound to be administered can be readily determined by the attending diagnostician, as one skilled in the art, by the use of conventional techniques and by observing results obtained under analogous circumstances. Factors significant in determining the dose include: the dose; the species of animal, its size, age and general health; the specific disease involved, the degree of or involvement or the severity of the disease; the response of the individual patient; the particular compound administered; the mode of administration; the bioavailability characteristics of the preparation administered; the dose regimen selected; the use of concomitant medication; and other relevant circumstances. That said, the exact amount employed may vary over a wide range. For example, from about 0.625 to 200 mg/kg of body weight per day, preferably from about 0.5 mg to 100 mg/kg of body weight per day.

In practicing the methods of this invention, the active ingredient is preferably incorporated into a composition containing a pharmaceutical carrier, although the compounds are effective, and can be administered, in and of themselves. The term "pharmaceutical carrier" refers to known pharmaceutical excipients useful in formulating pharmaceutically active compounds for administration, and which are substantially nontoxic and nonsensitizing under conditions of use. The exact proportion of these excipients are determined by the solubility and chemical properties of the active compound, the chosen route of administration as well as standard pharmaceutical practice.

That said, the proportion of active ingredient can vary from about 5% to about 90% by weight.

Formulations

The pharmaceutical compositions of the invention are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, powders, syrups, and the like. As used herein, the term "pharmaceutical carrier" means one or more excipients.

In preparing formulations of the compounds of the invention, care should be taken to ensure bioavailability of an effective inhibitory amount, including oral, parental and subcutaneous routes. For example, effective routes of administration may include, subcutaneously, intramuscularly, intravenously, transdermally, intranasally, rectally and the like including release from implants as well as direct injection of the active ingredient and/or composition directly into the tissue or tumor sites. Suitable pharmaceutical carriers and formulation techniques are found in standard texts, such as *Remington'sPharmacuetical Sciences*, Mack Publishing Co., Easton Pa., which is herein incorporated by reference.

For oral administration, the compounds can be formulated into solid or liquid preparation, with or without inert diluents or edible carrier(s), such as capsules, pills, tablets, troches, powders, solutions, suspensions or emulsions. The tablets, pills, capsules, troches and the like may also contain on or more of the following adjuvants: binders such as microcrystalline cellulose, gum tragacanth or gelatin; excipients such as starch or lactose, disintegrating agents such as alginic acid, Primogel®, corn starch and the like; lubricants such as stearic acid, magnesium stearate or Sterotex®, glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or a fatty oil. Materials used should be pharmaceutically pure and non-toxic in the amounts used.

For parental administration, the compounds may be administered as injectable dosages of a solution or suspension of the compound in a physiologically acceptable diluent with a pharmaceutical carrier which can be a sterile liquid such as water-in-oil or without the additions of a surfactant and other pharmaceutically acceptable excipients. Illustrative of oils which can be employed in the preparations are those of petroleum, animal, vegetable or synthetic origin. For example, peanut oil, soybean oil, and mineral oil. In general, water, saline, aqueous dextrose and related sugar solutions, ethanols and glycols, such as propylene glycol are preferred liquid carriers, particularly for injectable solutions. The parental preparation can be enclosed in ampules, disposable syringes or multiple dose vials made of inert glass or plastic.

The solutions or suspension described above may also include one or more of the following adjuvants: sterile diluents such as water for injection, saline solution, fixed oils, polyethylene glycols, glycerine, propylene glycol or other synthetic solvents, antibacterial agents such as ascorbic acid or sodium bisulfite; chelating agent such as ethylene diaminetetraacetic acid; buffers such as acetates, citrates or phosphates and agents for the adjustment of tonicity such as sodium chloride or dextrose.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Further information on suitable pharmaceutical carriers and formulation techniques are found in standard texts such as *Remington's Pharmaceutical Sciences*.

Chemical Syntheses

The following reaction schemes and descriptive text describe the preparation of the various compounds of the invention. Different combinations and permutations to arrive at individual compounds are readily apparent to one of ordinary skill in the art.

Scheme A represents a potential syntheses for the $C_{17}$-cyclopropyl-5-ene steroid compounds of the invention starting from testesterone. Testosterone or 17β-hydroxy-androst-5(6)-en-3-one [1] is treated with a strong oxidizer which breaks open the A-ring of the steroid nucleus to give the corresponding 4-nor-3,5-seco-acid [2]. For example potassium permanganate with sodium periodate in aqueous potassium carbonate and tert-butanol or methanolic ozone in methylene chloride at reduced temperature have proved effective. Care should be taken, however, to assure that over-oxidation does not occur, thereby converting the $C_{17}$-hydroxy substituent into a ketone.

The seco-acid [2] can be converted into the corresponding lactam or 4-aza steroid [3] by refluxing in the presence of an ammonium acid addition salt and an acid. For example, ammonium acetate in acetic acid. The corresponding 4-alkyl-aza compounds of the invention can be prepared by refluxing with the appropriate alkylamine or alkylamine hydrochloride under acidic conditions. For example, to create the desired 4-methyl-4-aza steroid, the seco-acid [2] is refluxed with methylamine hydrochloride in the presence of acetic acid. The acid addition ester [3] can be converted into the corresponding 17-alcohol [4] under basic hydrolysis conditions, such as aqueous sodium hydroxide in ethanol. Tetrahydrofuran (THF) may be employed, as necessary to assist in the solubility of the steroid substrate.

The 17-alcohol [4] can be converted into the vinyl ether [5] by etherification with a vinyl ether in the presence of a suitable etherification catalyst and solvent. For example, ethyl vinyl ether and mercuric acetate in chloroform or chloroform/tert-butyl methyl ether. A. B. Charette, et al., *Tet. Lett.* 35(4), 513–516 (1994). The vinyl ether [5] can then be converted into the cyclopropyl ether [6] under typical cyclopropanation conditions, such as by reaction with tert-butyl methyl ether, diethyl zinc and methylene iodide in methylene chloride.

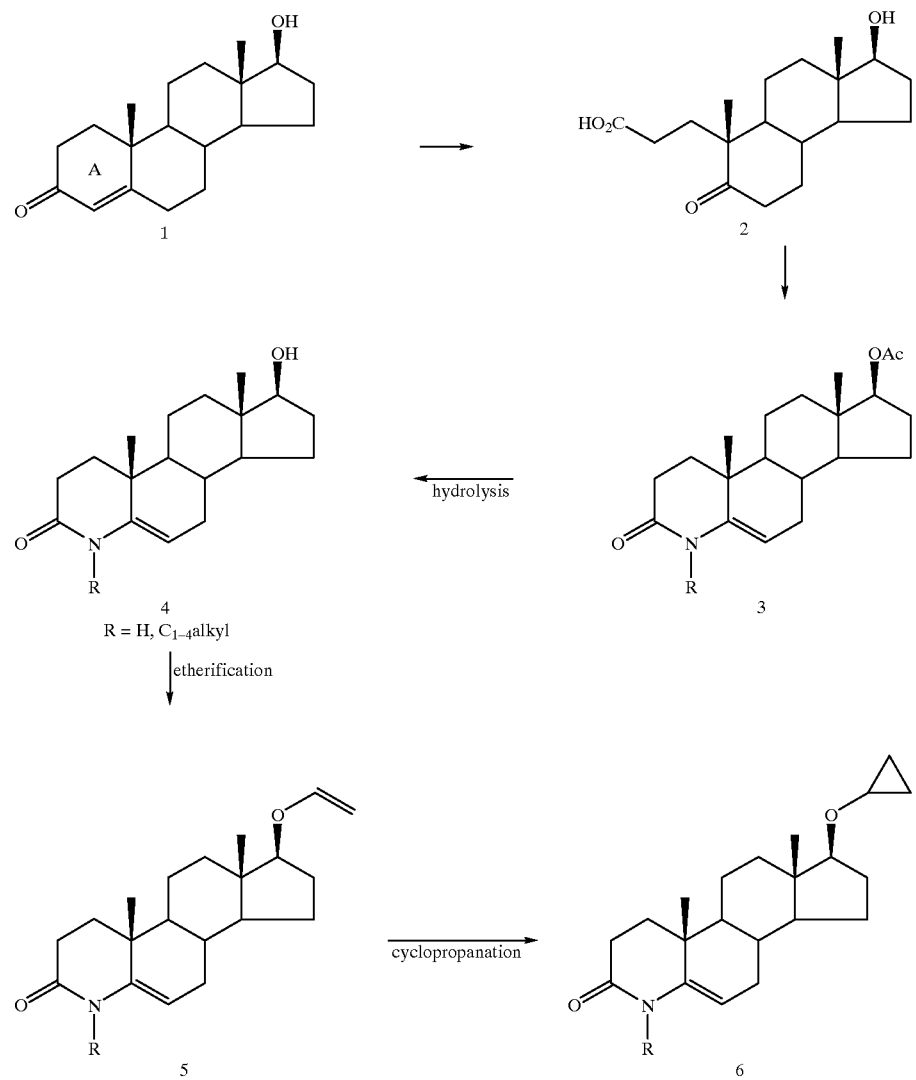

Scheme A

Scheme B graphically illustrates a synthetic route for the preparation of the saturated B-ring $C_{17}$-cyclopropyl ether compounds of the invention. In Scheme B, Option A, the 5-ene $C_{17}$-acid ester [3] is hydrogenated to the saturated acid ester [7] and then hydrolyzed to the saturated 17-alcohol [8]. Typical hydrogenation conditions include heating with hydrogen in the presence of ethanol and 5% palladium on carbon catalyst. The hydrolysis conditions are similar to those reported under Scheme A, aqueous sodium hydroxide in ethanol and tetrahydrofuran, the solvent choice as necessary to dissolve the reactants. However, the hydrogenation and hydrolysis steps may be reversed, that is, under Option B, the 5(6) unsaturated 17-alcohol [4] is created directly by hydrolyzing the acid ester [3], and then hydrogenated to give the saturated 17-alcohol [8]. The 17-alcohol [8], can then be etherified and cyclopropanated as described in Scheme A to give the 17β-cyclopropylether [9]. By "inert substituent" in the definition of R', it is meant a substituent(s) which is (are) unaffected by the reaction conditions of the scheme.

application of conditions similar to those described for the corresponding reaction in Scheme A. For example, refluxing in the presence of ammonium acetate and acetic acid. The 4-alkyl compounds may be prepared in a similar manner,

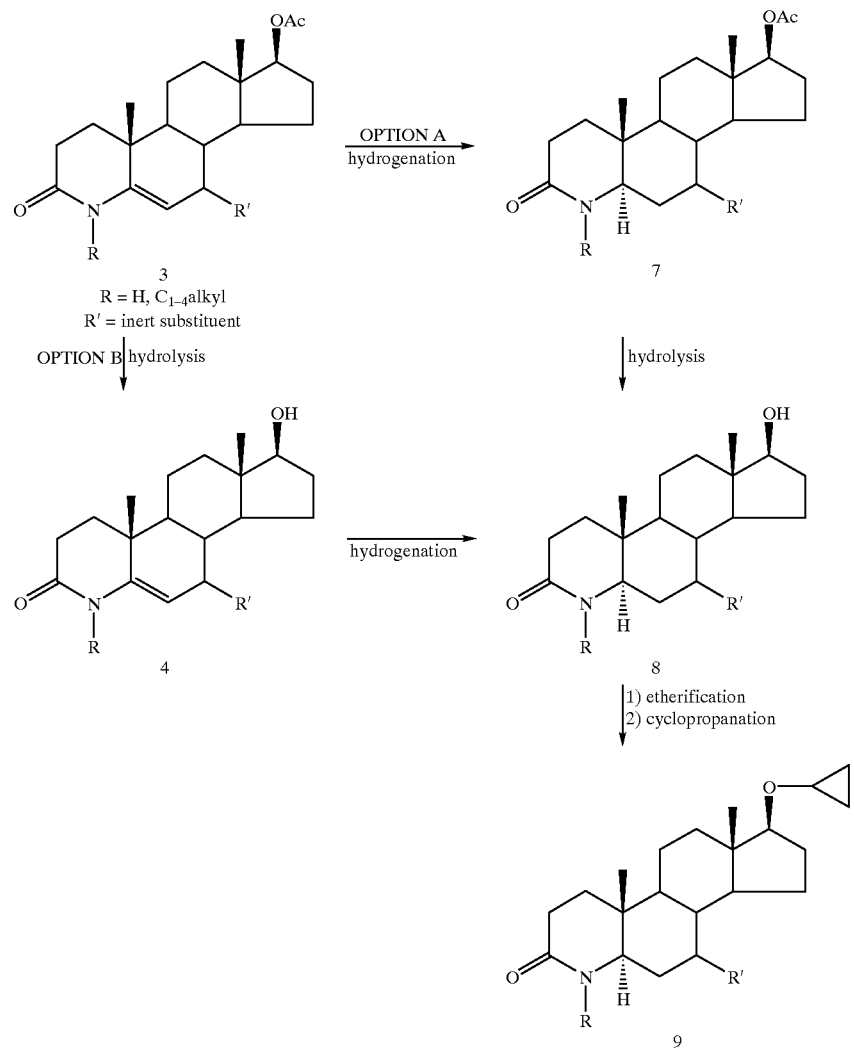

Scheme B

Scheme C illustrate a potential synthesis for the preparation of the compounds of the invention having a 17-cyclopropylamino substituent. The starting compound, testosterone [1] is treated to oxidation conditions sufficient to break open the A-ring of the steroid nucleus to give the corresponding 17-keto-4-nor-3,5-seco-acid [10]. This may be effected in a manner similar to that described for the preparation of compound [2] in Scheme A. Preferably, since oxidation of the $C_{17}$-hydroxy substituent to the $C_{17}$-ketone is desirable, modified reaction conditions from the Scheme A ring cleavage are employed. For example, bubbling ozone at reduced temperature (−78° C.) in methylene chloride and ethyl acetate. Non-alchoholic solvents are employed to ensure that transesterification with the newly formed seco-acid does not occur. The seco-acid [10] is converted into the corresponding 17-keto lactam or 4-aza steroid [11] under the e.g., refluxing in acidic alkylamine or acidic alkylamine hydrochloride. To obtain the 5(6)-olefin, as defined by Route A, the 17-keto lactam [11] is converted into the corresponding 17-cyclopropylimino compound [12] by reaction with cyclopropylamine in chloroform. THF may be used as a cosolvent, if necessary to solubilize the steroid substrate. The cyclopropylimine [12] is reduced to the corresponding 17-cyclopropylamine [13] by reaction with a suitable reducing agent such as sodium borohydride.

The saturated cyclopropylamino compounds of the invention can be prepared also under Scheme C following Route B. The 17-keto lactam [11] is hydrogenated preferentially by action of $H_2$ gas with palladium catalyst to obtain the saturated 17-hydroxy lactam [14]. The 17-alcohol [14] may be oxidized to the corresponding 17-ketone

Scheme C

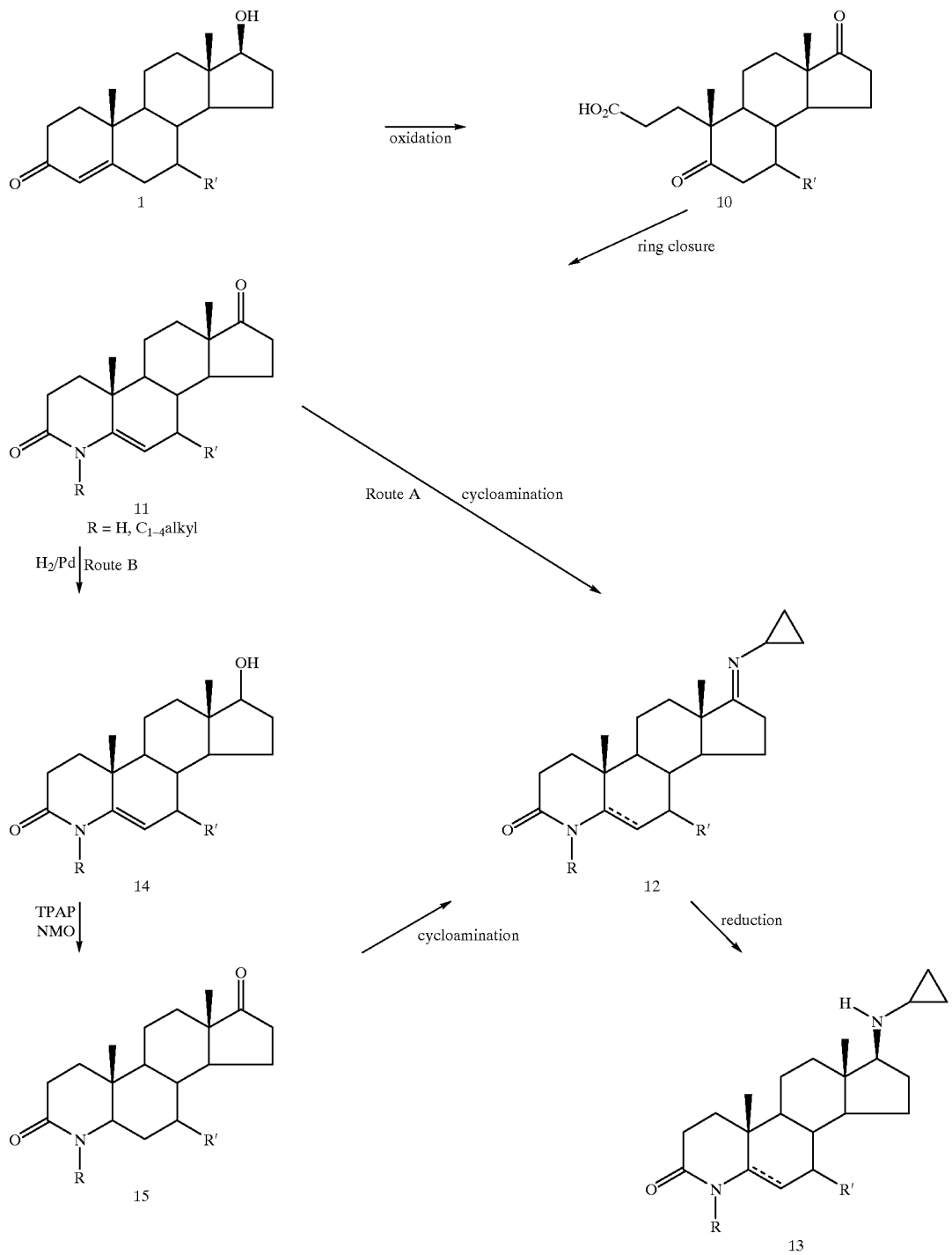

[15] by reaction with tetrapropylammonium perruthenate (VII) (TPAP) and 4-methylmorpholine N-oxide (NMO) in the presence of 4 Å molecular sieves. The 17-ketone [15] is then converted into the corresponding cyclopropylimine [12] and reduced to give the 17-cyclopropylamino compound [13] in a similar manner as described in Route A, above.

Scheme D illustrates a potential synthesis for the 1-halo-$\Delta^1$ compounds of the invention. The synthesis may begin with the saturated acid ester [7], also an intermediate of Scheme B. To obtain the 1-halo-$\Delta^1$-4-aza compounds of the invention, The acid ester [7] is then dehydrogenated preferentially at the $\Delta^{1(2)}$ positions to give the corresponding 1(2)-ene [16], as is known. For example, reaction with 2,3-dichloro-5,6-dicyano-1,4-benzoquinone (DDQ) and bis (trimethylsilyl)-trifluoroacetamide (BSTFA) in dioxane. Bhattacharya et al. *J.Am. Chem. Soc.*, 1988, 110, 3318–3319. Under Option A, the hydrolysis, vinylation and cyclopropanation may be performed in a manner similar to that described under Scheme A to give the $\Delta^{1(2)}$-ene-17-cyclopropylether [17]. Under Option B, the 17-cyclopropylamine [17] is formed by first hydrolysing to the 17-alcohol, as under option A, but then oxidizing, cycloaminating and reducing as described under Route B in Scheme C.

Compound [17] can be converted into the corresponding 1-phenylthioether [18] by reaction with phenylmercaptan (thiophenol) in sodium hydride. The thioether [18] can be changed into the 1,2-halo compound [19] by reaction with N-bromo-succinimide (NBS) and diethylaminosulfur trifluoride (DAST). Bohlmann, R. *Tetrahedron Lett.* 1994, 35(1), 85–88. The 2-halo substituent can then be eliminated by reaction with tributyltin hydride and azobisisobutylronitrile to give the desired 1-fluoro-$\Delta^{1(2)}$ compound [20]. This compound [20], may be hydrogenated, if desired by reaction with $H_2$ gas over palladium to give the saturated 1-fluoride [21].

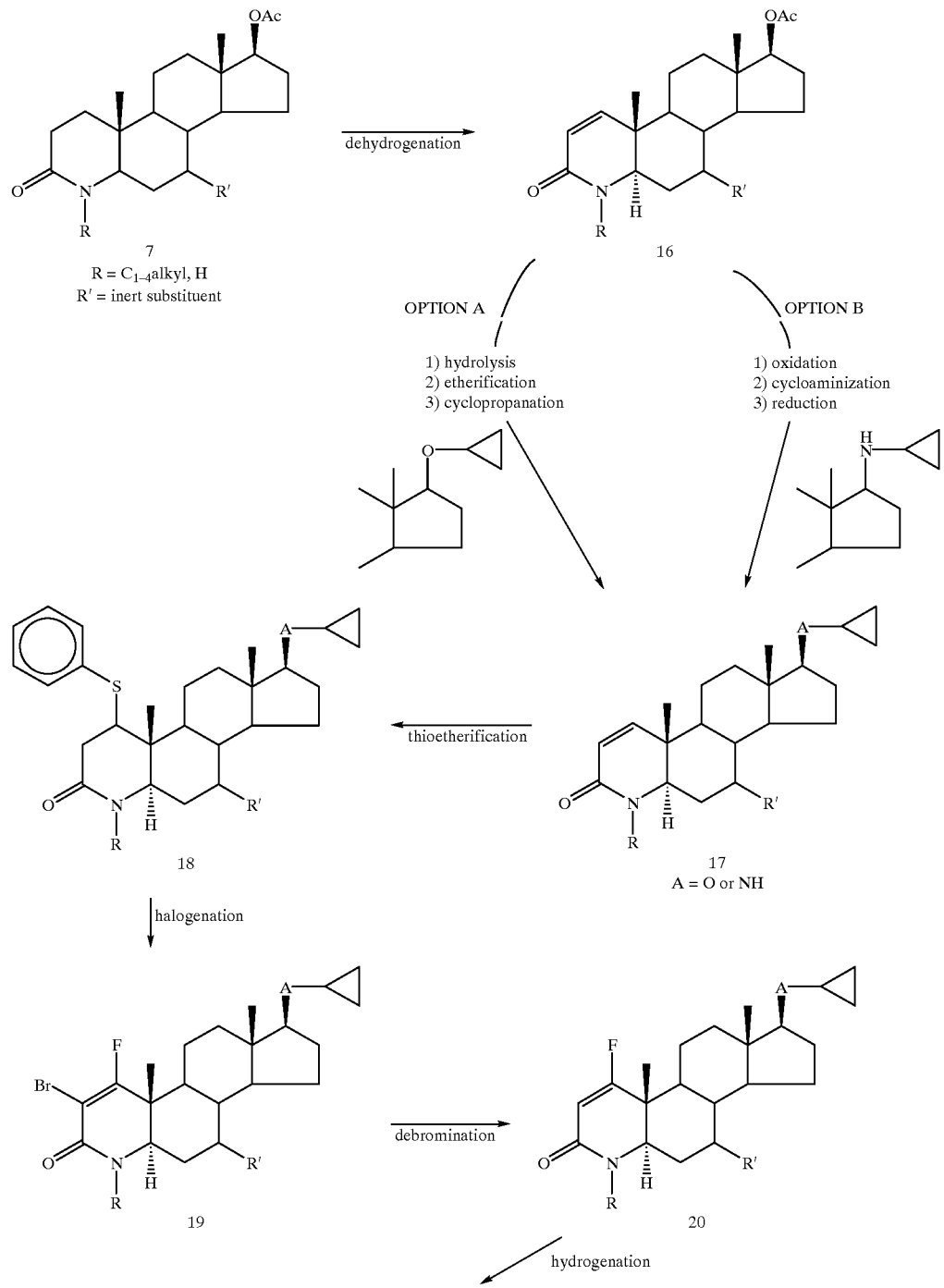

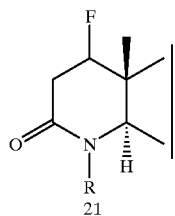

Scheme E graphically represents a potential synthesis for the 1-phenylsulfinyl and 1-phenylsulfonyl compounds of the invention, starting from the 1-phenylthioether [18], the preparation thereof described in Scheme D, as is known. For example, compound 18 may be reacted with 3-chloroperoxybenzoic acid at reduced temperature (−78° C.) for 3 hours under nitrogen to create the 1-phenylsulfinyl thioether. The 1-phenylsulfonyl thioether is created under similar reaction conditions as the sulfinyl ether, except the reaction occurs at room temperature, and the time is extended to 16 hours.

The protected ether [14] may then be halogenated by reaction with N,N,N',N'-tetramethylethylenediamine (TMEDA) and the desired halogenated silylating agent at reduced temperature under an inert atmosphere. Once halogenated, the protecting group is removed for subsequent conversion of the 17-substituent. For example, to create the bromide [25], trimethylsilyliodide and bromine in TMEDA and toluene may be used initially, followed by tetrabutyl ammonium fluoride (TBAF) in tetrahydrofuran (THF). Correspondingly, the iodide [26], may be created by trim-

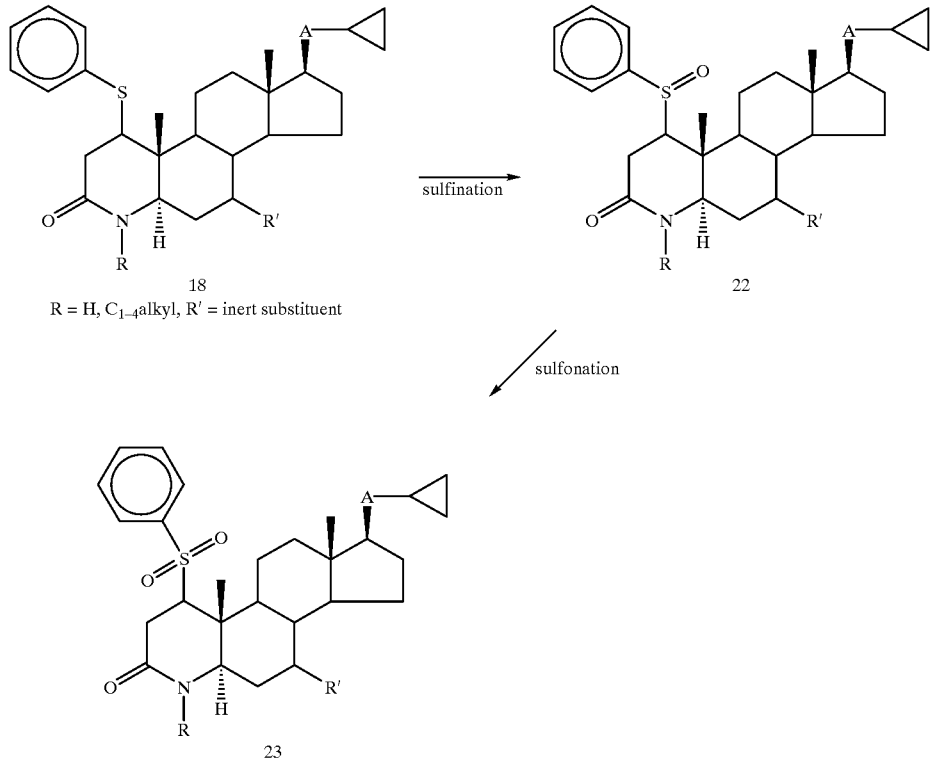

Scheme F represents the preparation of the 2α-halo compounds of the invention, starting from the 4-aza-17-alcohol [14], the preparation thereof is described in Scheme C, Route B. The 17-alcohol [14] is first converted into the protected ether [14] by any effective means, for example by reaction with trimethylsilyl chloride in methylene chloride.

ethylsilylchloride and iodine in TMEDA in toluene, followed by the action of TBAF in THF. The 2α-halogens [25]–[26] can then be converted into the corresponding 17β-cyclopropylamino compound [27]–[28 as in Scheme C, or the corresponding 17β-cyclopropyloxy compound [27]–[28] as described in Scheme A.

Scheme F

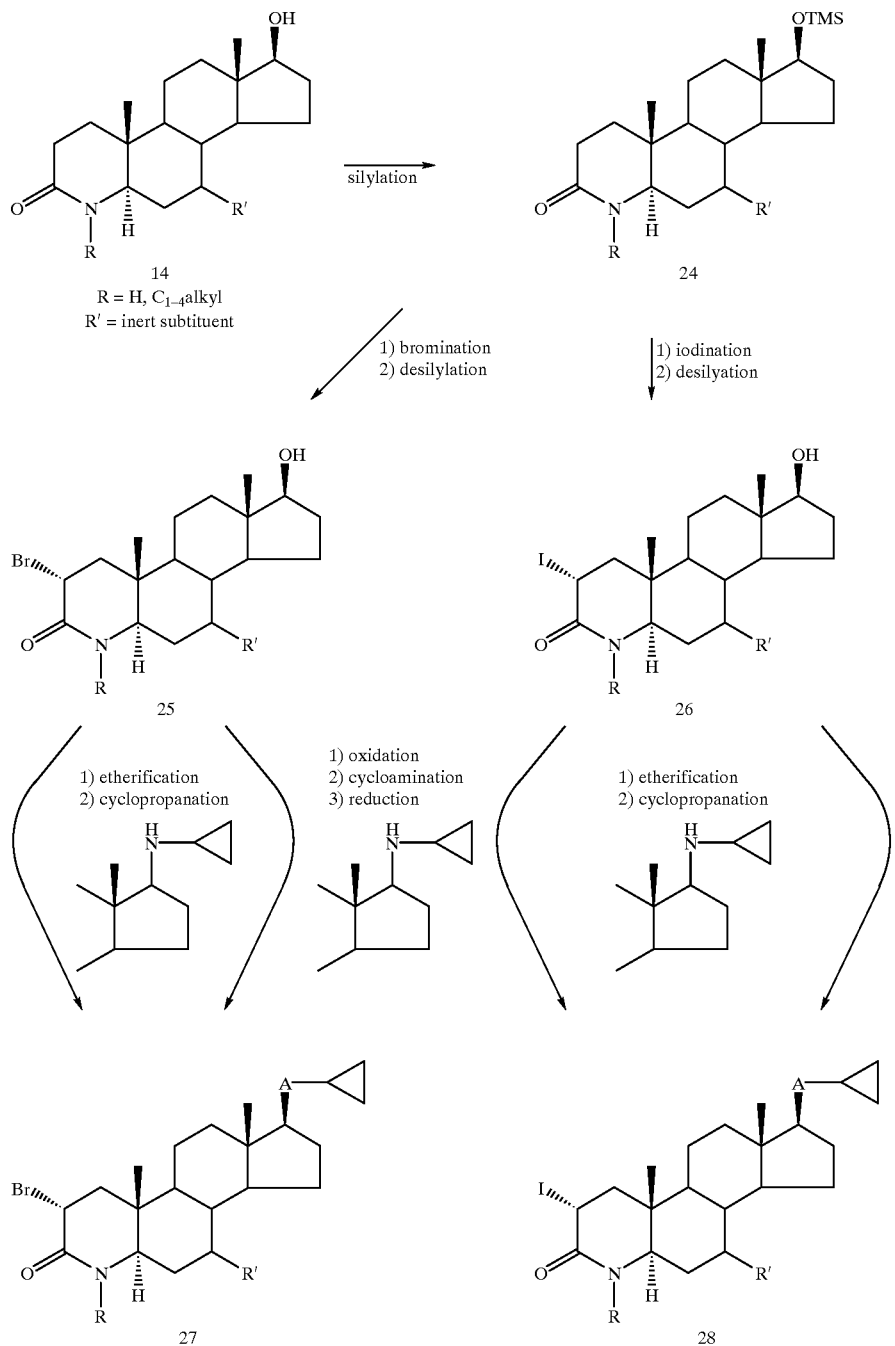

Scheme G represents a synthesis for the creation of the 2α-alky-thio/alkyl-sulfinyl/and alkyl-sulfonyl compounds of the invention starting from the 2α-iodo -cyclopropyl- ether or -cyclopropylamino compound [28]. The alkyl thio- ether [29] may be created by reaction with the corresponding alkali metal salt of the alkyl thiol in a suitable solvent, as is known. For example, the methyl thioether may be created by employing sodium thiomethoxide (sodium methyl sulfide; sodium methanethiolate) in ethanol. The sulfoxide [30] and sulfone [31] can then be created as in Scheme E.

Scheme G

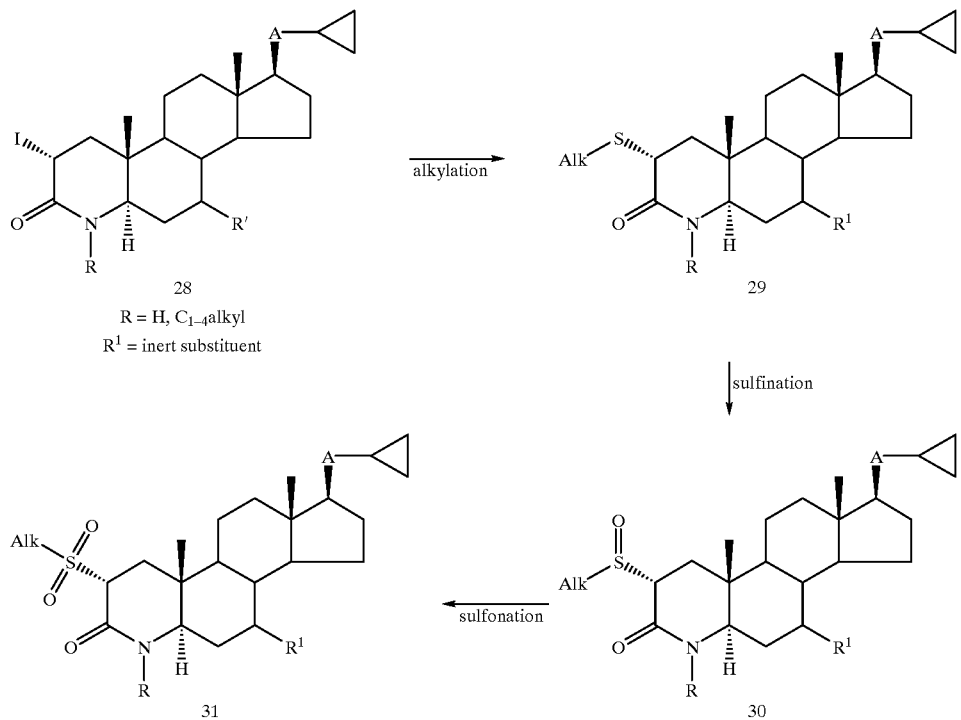

Scheme H₁ represents a synthesis for the creation of the 7β-alkyl compounds of the invention starting from 17β-hydroxy-androst-5-en-3-ol 3-acetate [32]. In Scheme H₁, compound 32 is first protected by any suitable protecting agent. For example, t-butyldimethylsilyl chloride and diazabicyclo[5.4.0]undec-7-ene (DBU) in methylene chloride. The protected acetate [33] is then C₇-oxidized to create the 7-ketone [34] by any known means. For example, by reaction with t-butylchromate in acetic anhydride, acetic acid and carbon tetrachloride. Pinto, A. et al., *Chem. Pharm. Bull.* 1988, 36(12), 4689–4692. The 7-ketone is then reacted with the appropriate Grignard to give the corresponding 7-alkyl-7-alcohol [35]. For example, the 7-ethyl-7-alcohol may be formed by reaction with ethylmagnesium chloride in THF. For example, the 7-aryl-7-alcohol can be formed by reaction with 4-bromotolylmagnesium chloride in THF.

The 7-substituted-7-alcohol [35] is dehydrated to the 7-alkyl diene [36] by reaction in a suitable matter, such as for example, by reaction with aluminum isopropoxide in the presence of toluene and cyclohexanone. Eastham, J. F. & Teranihi, R., *Org. Synth., Coll. Vol. IV* 1963, 192–195; Djerassi, C. *Org. React.* 1961, 6, 207–272. The diene [36] can then be hydrogenated and isomerized under known conditions to give the olefin [37]. For example, reaction with dry ammonia and lithium metal in t-butanol and toluene. Crabtree et al. *Org. Synth.* 1991, 70, 256–264; Caine, D. et al. *Org. Synth. Coll. Vol. VI* 1988, 51–55; Caine D. *Org. React.* 1976, 23, 1–258.

Scheme H₁

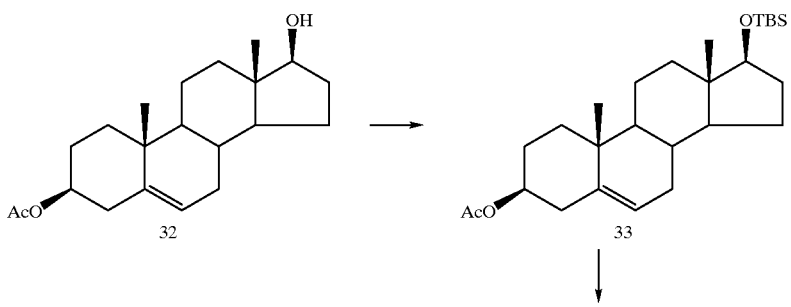

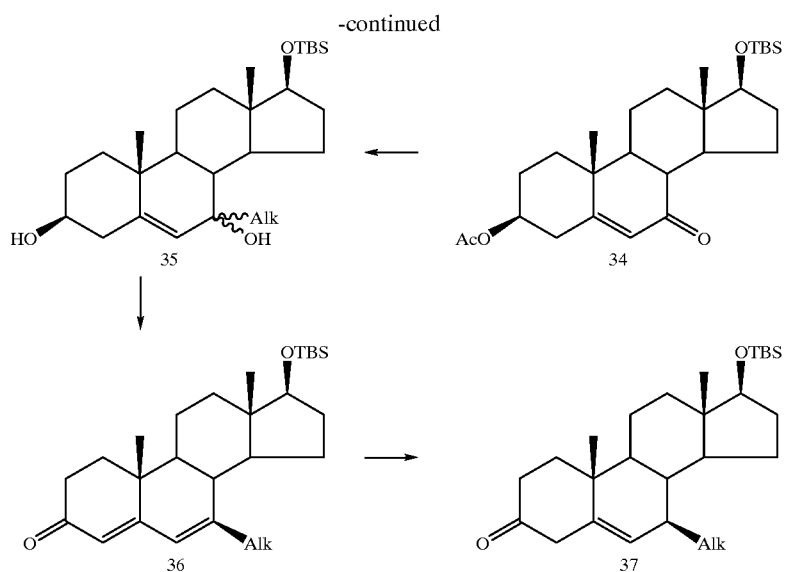

In Scheme H$_2$, the olefin [37] can be isomerized and desilyated to the 4-en-17-alcohol [38] by any appropriate reagents. For example, reaction with 1,8-diazabicyclo[5.4.0]undec-7-ene at reflux followed by cooling to room temperature and reaction with tetrabutylammonium fluoride. Under Route A, compound [38] is then oxidized, lactamized and hydrolyzed as described in Scheme A to give the 4-aza-17-alcohol [39], which can then be etherified and cyclopropanated as in Scheme A to give the corresponding cyclopropyl ether [40].

In the creation of the cyclopropylamine [42] under Route B, the 17-alcohol [39] can be oxidized to the ketone [41] and then cycloaminated and reduced as in Scheme C, Route B. However, it is also readily apparent that the cyclopropylamine can be prepared from the 17-alcohol [38] with fewer synthetic steps by performing the oxidative ring cleavage, lactamization, cycloamination and reduction as described in Scheme C, Route A (not shown in Scheme H$_2$).

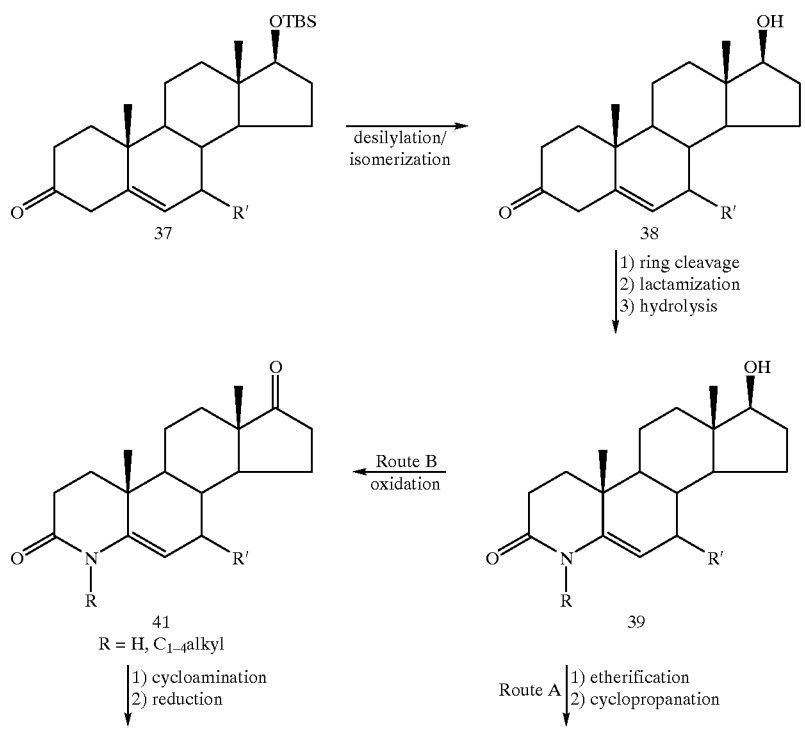

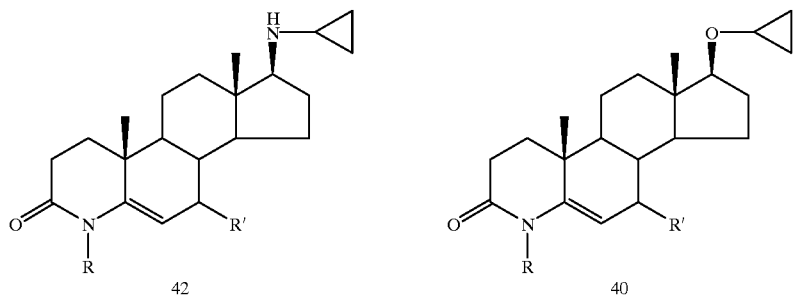

Scheme I graphically describes a synthesis for the 7-hydroxy-, 7-oxo- and 7-alkanoyloxy-17β-cyclopropyl ether compounds of the invention from 3β-acetoxy-17β-t-butyldimethylsilyloxy-androst-5-en-7-one [34]. Compound [34] is ketalized under appropriate known reaction conditions, such as, for example reaction with 1,2-bis(trimethylsiloxy)ethane and trimethylsilyl trifluoromethanesulfonate in methylene chloride at −78° C., to give the 7-ketal 3-acetate [43]. Tsunoda, T. et al., *Tetrahedron Lett.* 1980, 21 (14), 1357–1358; Hwu, J. R. et al., *J. Org. Chem.* 1987, 52(2), 188–191. Compound [43] is hydrolyzed as in Scheme A followed by oxidation to the 3-ketone [44]. The oxidation may be carried out, for example, similarly as the conversion of of compound [35] to [36] in Scheme $H_1$, i.e., refluxing with aluminum isopropoxide in the presence of toluene and cyclohexanone. The 3-ketone [44] is then desilylated/isomerized, oxidized, lactamized and hydrolyzed as described in Scheme $H_2$ to give the 17-alcohol [45]. The 17-alchohol [45] can then be etherified and cyclopropanated as in Scheme A to give the 3,7-dioxo-17β-cyclopropyl ether [46].

The cyclopropyl ether [46] can be reduced directly into the 7-alcohol [48], as is indicated in Option A, or it can first be hydrogenated to compound [47] and subsequently reduced, as indicated in Option B. The reduction conditions may be similar to those used in previous Schemes, for example, sodium borohydride in ethanol and THF. The hydrogenation may also be carried out in a manner similar to that described previously (Scheme B), for example, heating in the presence of hydrogen and palladium catalyst.

The cyclopropylether 7-alcohol [48] may be esterified into alkyl alcohol esters [49] by reaction with the appropriate alkyl anhydrides. For example, to create the alcohol ester of proprionic acid, compound [48] is reacted with prionic anhydride in pyridine. Baer, H. H. et al., *Can. J. Chem.* 1991, 69, 1563–1574.

Scheme I

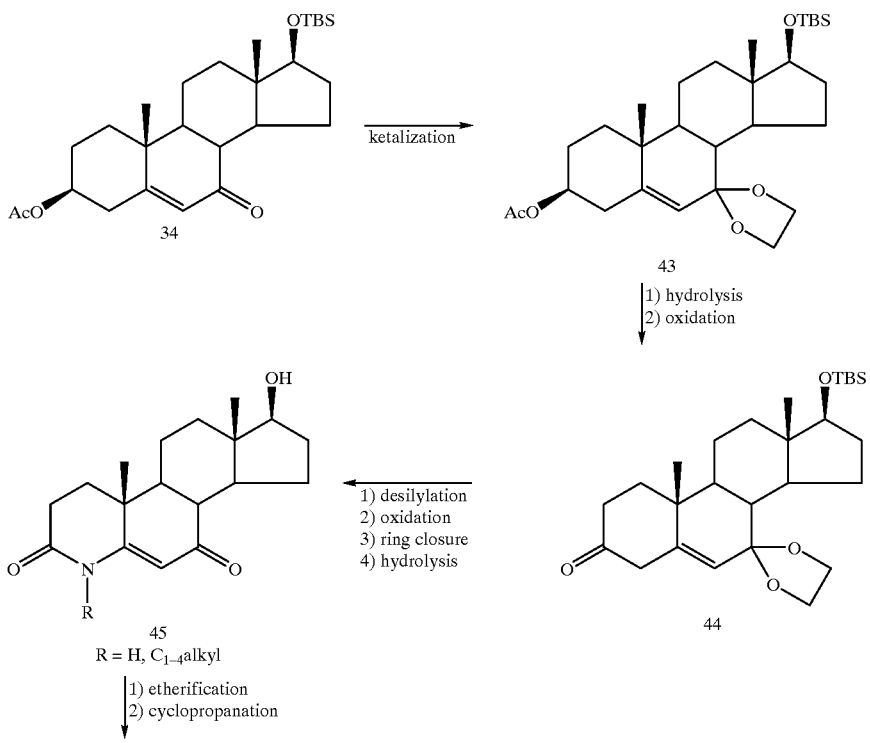

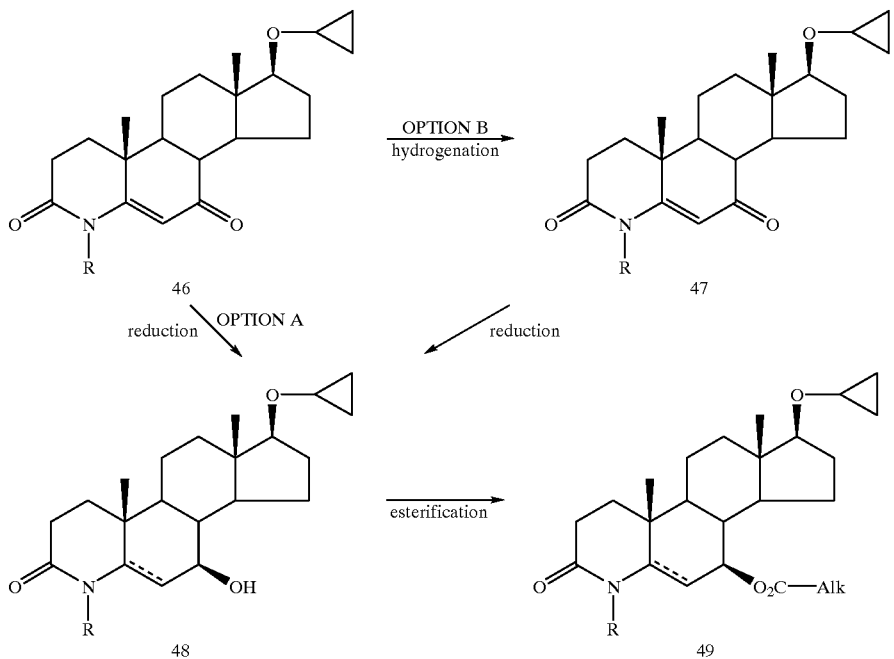

In Scheme J, there is illustrated the preparation of the 7-oxo-, 7-hydroxy- and 7-alkoxycarbonyl-17-cyclopropylamino compounds of the invention, starting from the 17β-hydroxy-3,7-dione [45], also an intermediate of Scheme I. Compound [45] is first deprotonated and then immediately silylated to create the protected ether [50]. Suitable conditions include, for example, reaction with lithium diisopropylamide followed by trimethylsilyl chloride at −78° C. The protected ether [50] can then be dehydrogenated and 7-silyated and acid hydrolyzed in the conventional manner. Suitable reaction conditions include, for example, treatment with lithium diisopropylamide in THF at −78° C. followed by addition of t-butyldimethylsilyl chloride. Once this reaction product is worked-up, it can be acid hydrolyzed with acetic acid in THF to give the 17-alcohol-7-protected ether [51]. Compound [51] can then be oxidized, cycloaminated and reduced as in Scheme C, Route B to give the protected cyclopropylamine [52].

Compound [52], when deprotected, affords the 3,7-dioxo cyclopropylamine [53]. Suitable conditions for this conversion, include for example, tetrabutylammonium fluoride in THF under an inert atmosphere. The remaining compounds in the Scheme [54], [55] and [56] may be made in a manner similar to that described under Scheme I.

Scheme J

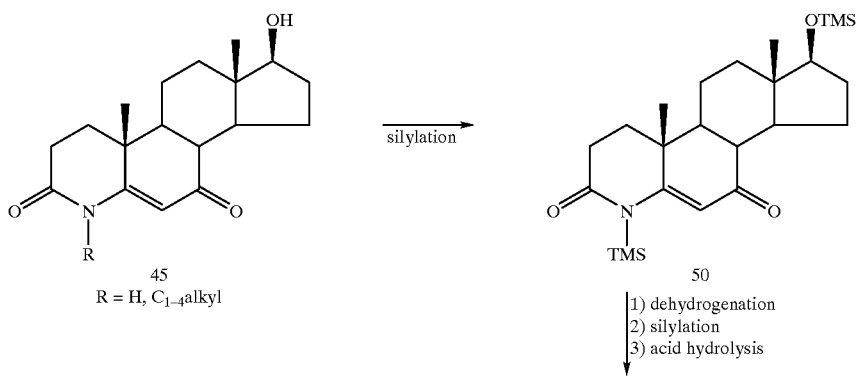

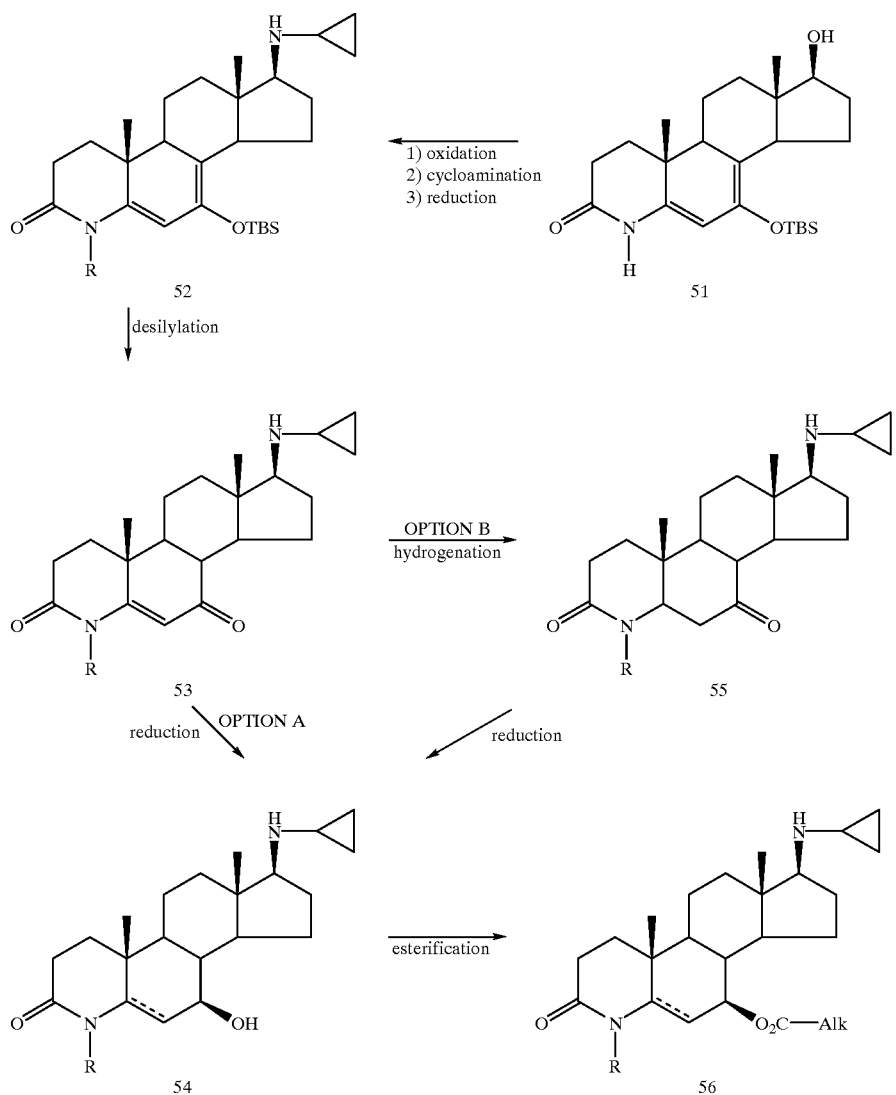

Scheme K graphically illustrates a potential preparation of the 7-alkoxycarbonylmethyl and 7-carboxymethyl compounds of the invention starting from compound [50], also an intermediate in Scheme J. The protected 7-ketone [50] is carboxylated to form the alkylcarbonyloxymethyl diene [57] depicted. For example, the 7-ethyl methylcarboxylate may be created by reaction with triethyl phosphonoacetate in THF and sodium hydride. The diene [57] can then be desilylated and hydrogenated to the 17-alcohol [58] in the typical manner, such as by treatment with tetrabutylammonium fluoride in THF. The 17-alcohol [58] can be converted to the cyclopropylether [59], depicted under Option A, similarly as described in Scheme A. Alternatively, the 17-alcohol [58] may be converted into the cyclopropylamine [59], depicted under Option B, similarly as described in Scheme B. Compound [59] then may be base hydrolyzed in the conventional manner (Scheme A) to give the 7-ethanoic acid [60].

Scheme K

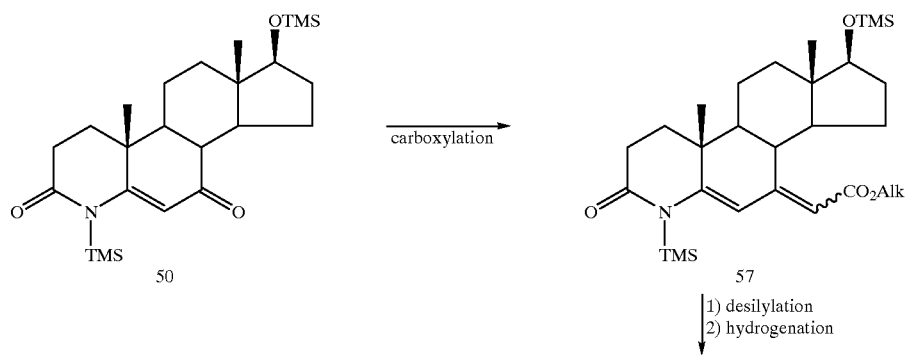

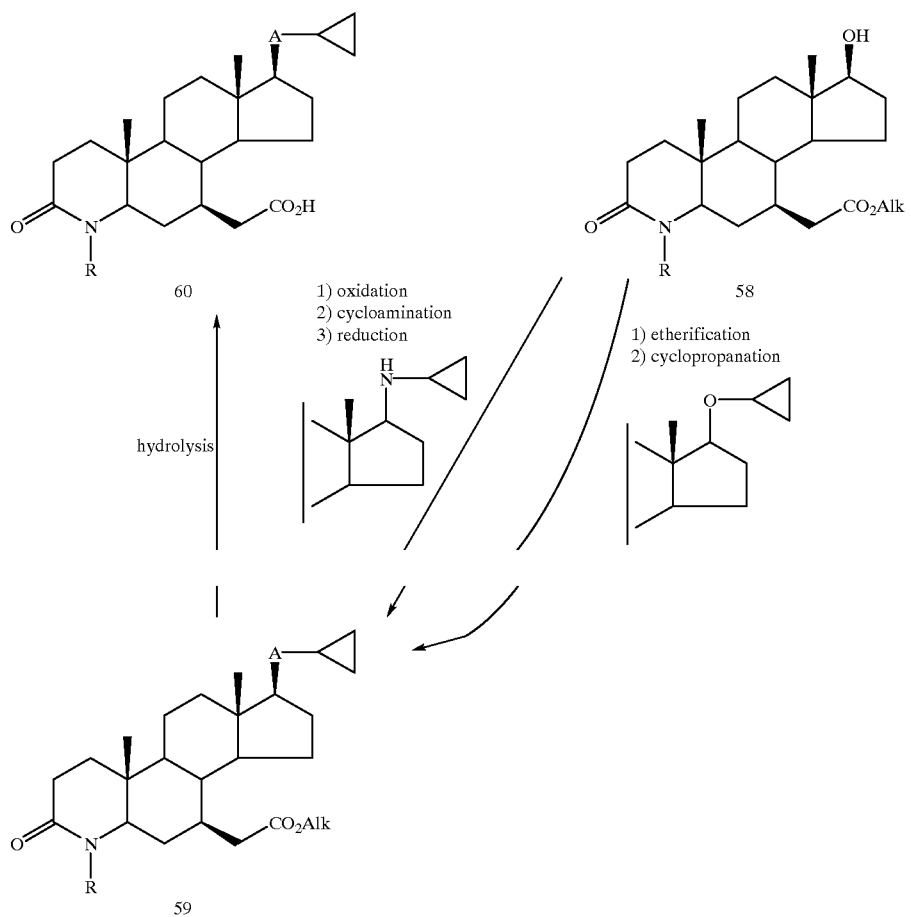

Scheme L graphically illustrates a synthesis of the 7-alkoxycarbonyl and 7-carboxylic acid compounds of the present invention starting from the 7-alkyl ethanoate [58], also an intermediate in Scheme K. The carbonyl is phenylated in the conventional manner, for example, by reaction with phenylmagnesium chloride (4 molar eq.) in THF to give the 7-diphenyl-methyl alcohol [61]. This compound [61] can then be dealkylated to the 7-acid [62], as is known. For example, reaction with chromium trioxide (chromic acid) in water, methylene chloride and acetic acid. Riegal, B. et al. *Org. Synth. Coll. Vol.* 3 1955, 234–236; Subramanium, C. S., et al. *Synthesis* 1978, 468–469. The 7-acid [62] may then be converted into the alkyl ester [63], as is known. For example, 4-(dimethylamino)-pyridine and 1,3-dicyclohexylcarbodiimide in methylene chloride and ethanol. Neises, B. and Steglich, W. *Org. Synth.* 1984, 63, 183–187. The ester [63] can then be converted into either the cyclopropylether [64A] (Scheme A) or the cyclopropylamine [64B] (Scheme C) as has been described previously. Compound [64] may subsequently be base hydrolyzed in the conventional manner (e.g. NaOH in water, ethanol and/or THF) to the 7-acid [65].

Scheme L

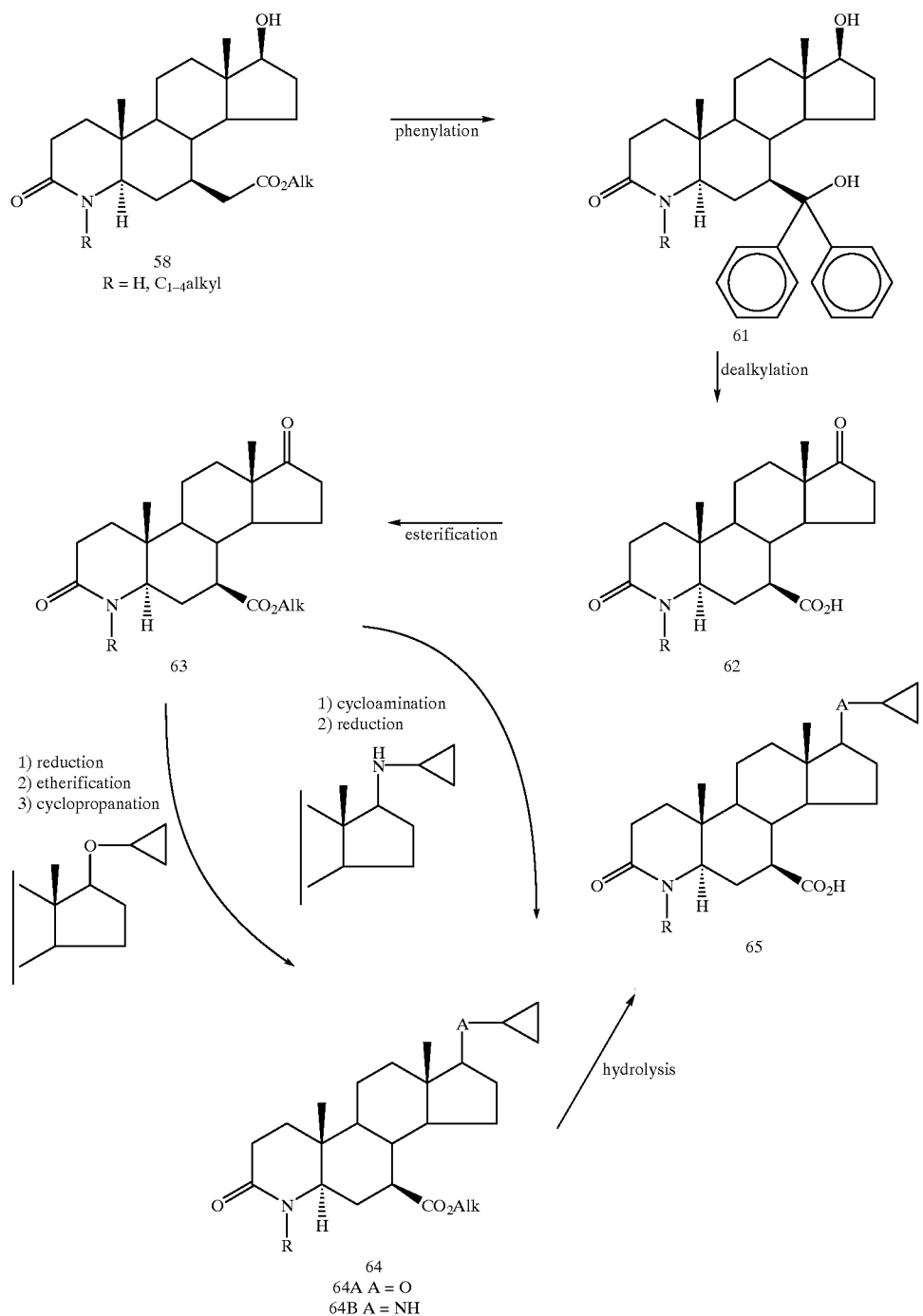

Scheme M illustrates the preparation of the 7α-ketone compounds of the invention starting from the 7-alkyl ester [63]. The ketone [63], is first reduced to the corresponding alcohol in the conventional manner (e.g., sodium hydride in ethanol), and silylated as in Scheme H₁ to give the protected ester [66]. The ester ([66] is then reduced to the 7-methyl alcohol [67]. Suitable reduction conditions include, for example, lithium borohydride in THF. Jeanloz, R. W. & Walker, E. Carbohydrate Res. 1967, 4, 504 and Walker, E. R. H. *Chem. Soc. Rev.* 1976, 5, 23–50. The alcohol is then oxidized into the 7-aldehyde [68]. Suitable oxidation conditions include, for example, 4-hydroxy-TEMPO benzoate in methylene chloride and sodium bicarbonate followed by sodium bromite. Inokuchi, T. et al., *J. Org. Chem.* 1990, 55, 462–466. The 7-aldehyde [68] is then alkylated to give the α-ketone alcohol, [69] which is then oxidized and desilylated in the conventional manner (Schemes C and J, respectively) to give the 17-hydroxy-7-alkanone [70]. For example, to create the 1-propanone, titanium tetrachloride and tetraethyl lead are sequentially added at −78° C. in methylene chloride. Yamamoto, T. and Tamada, J. I. *J. Am. Chem. Soc.* 1987, 109, 4395–4396. Compound [70] can then conditions taking care to minimize reaction with the acid-sensitive $C_{17}$-cyclopropylamine, as is known.

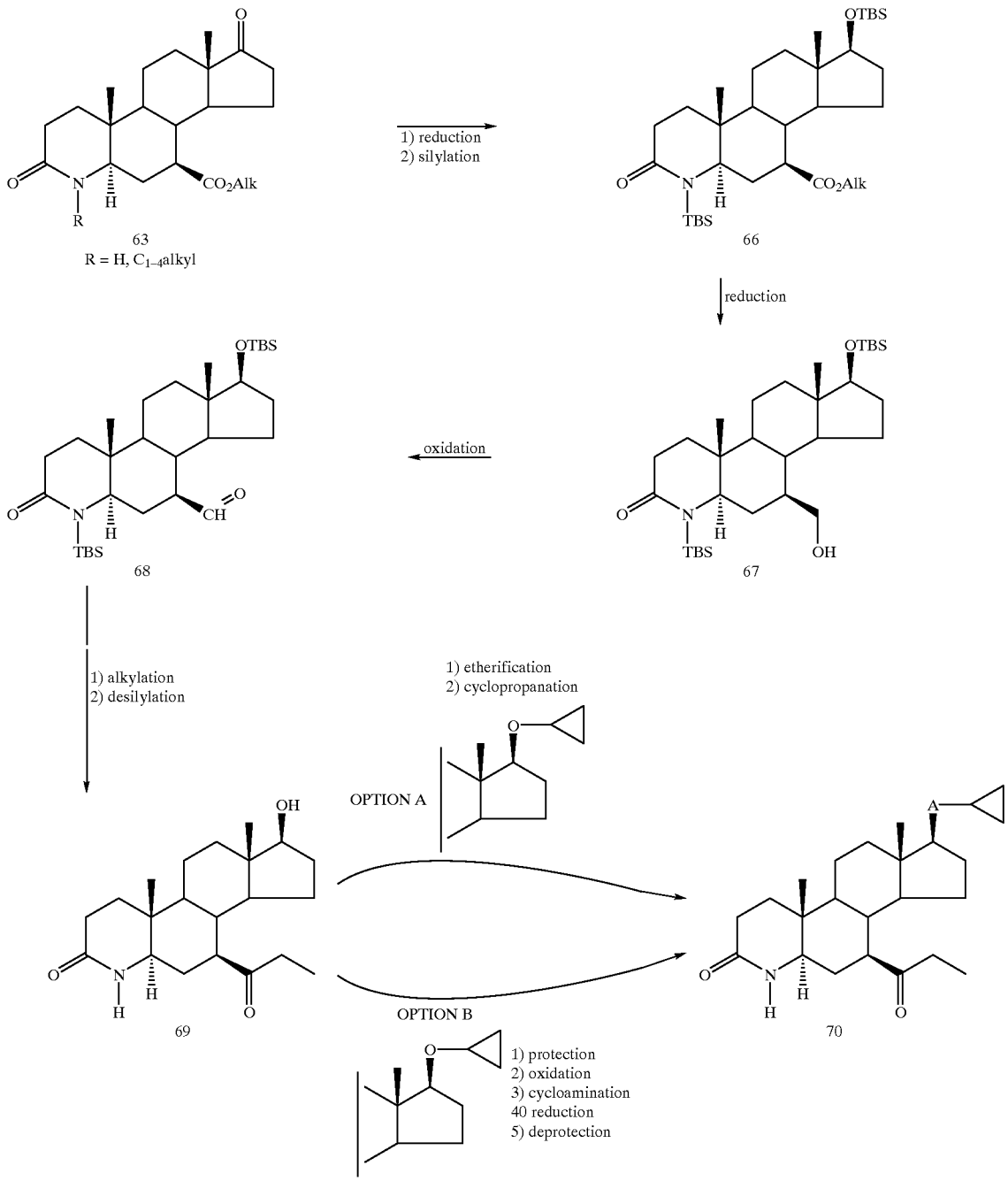

Scheme M be prepared as the cyclopropyl ether (Option A, Scheme A) or as the cyclopropylamine [70]. In the preparation of the cyclopropylamine, the 7-alkanoyl group must first be protected by suitable means, such as by formation of the ethylene or 2,2-dimethyl propane ketal, followed by the steps described in Option B, Scheme C, and subsequent deprotection. The protection may be effected, for example by ethylene glycol or 2,2-dimethyl-propan-1,3-diol, respectively, with acid catalysis and deprotected under acid Scheme N graphically illustrates a potential synthesis for the $C_{16}$-alkenyl and $C_{16}$-alkyl compounds of the invention, starting from androstenedione (androst-4-ene-3,17-dione) [72]. Compound [72] is treated in a manner similar to the procedure described in Scheme C to create the aza-androstenedione [11]. The dione can then be $C_{16}$-alkylated by known techniques to give the 16-alkenyl dione [73]. For example, to create the 16α-allyl dione, diethyl oxalate and sodium methoxide are sequentially added in methylene chloride solvent at 0° C., followed by reaction with methyl iodide at 55° C., and finally treatment with sodium methoxide. Carruthers, N. I. et al. *J. Org. Chem.* 1992, 57(3), 961–965. The alkenyl dione [73] can then be transformed into the cyclopropylether (Scheme A) or the cyclopropylamine (Scheme C) as previously described to give the 16-alkene [74]. The 16-alkene [74] may then be hydrogenated in the conventional manner, [Scheme B] to give the 16-alkane [75].

conventional manner (Scheme I) to give the 17-ketal [77]. The ketal [77] is α-brominated to give the 16-bromide [78]. Suitable bromination conditions include, for example, pyridinium perbromide in dry THF, followed by treatment with sodium iodide, then reaction with sodium thiosulfate in water and pyridine. The bromide [78] can then be dehydrogenated and 17-hydrolyzed into the 15-en-17-one. Typical dehydrogenation conditions include, for example, potassium t-butoxide in dimethylsulfoxide. Typical hydrolysis condi-

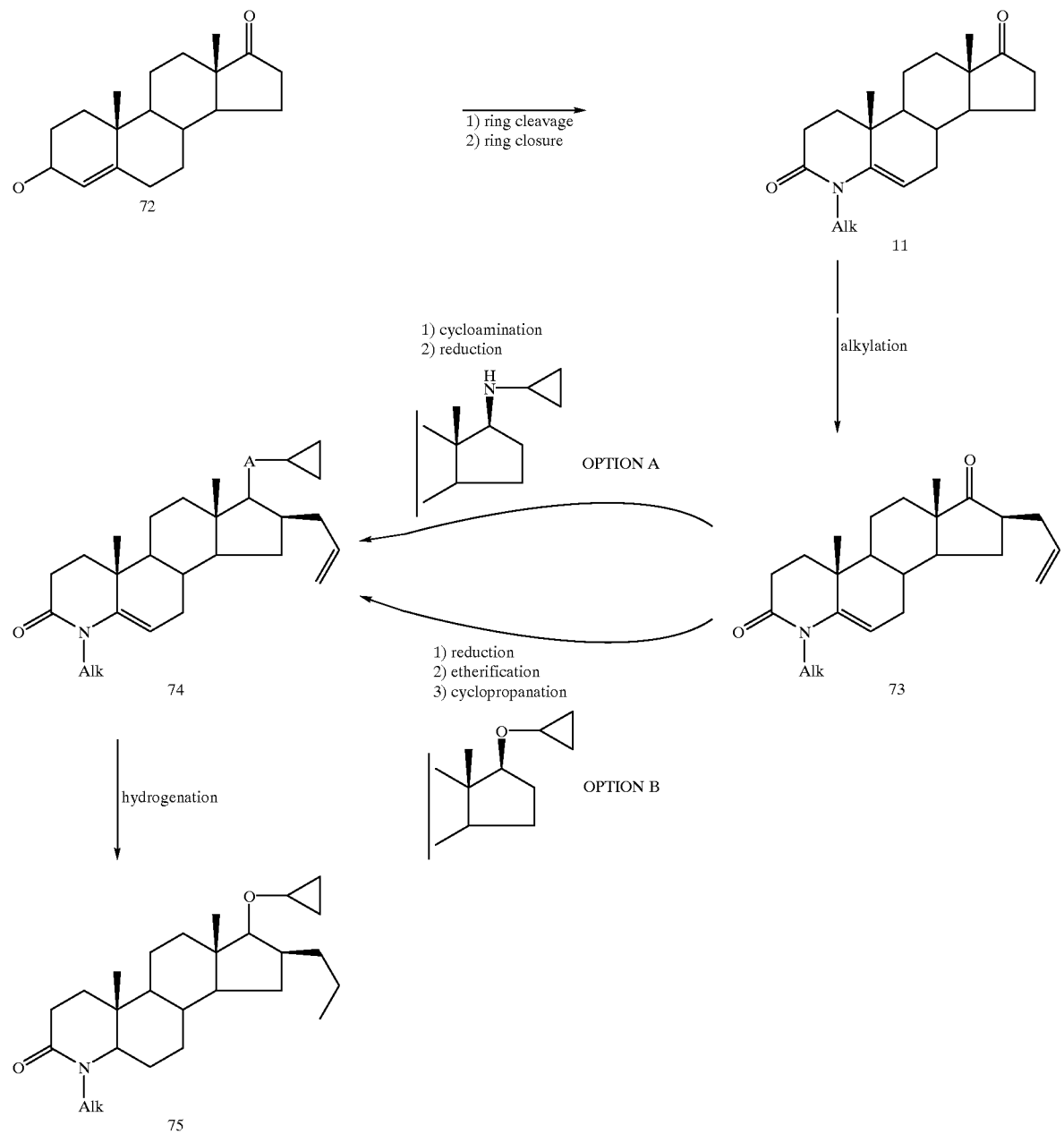

Scheme N

Scheme $O_1$ graphically represents the first part of a synthesis for the preparation of the 15-alkyl compounds of the invention starting from dehydroisoandrosterone 3-acetate (3β-acetoxy-5-androsten-17-one). The 3-acetoxy-17-one [76] can be ketalized at the $C_{17}$ position in the tions include, for example, p-toluenesulfonic acid monohydrate. The ketone, prepared by hydrolyzing the ketal, can then be silylated in the conventional manner (Scheme $H_1$) to give the silylated diene [79]. The silylated diene [79] can then be selectively alkylated at $C_{15}$ to give the 15-alkyl silylated 17-ketone [80], as is known in the art. For example, to create the 15-ethyl compound, compound [79] may be dropwise added to ethylmagnesium chloride in ether previously treated with cuprous chloride in THF. The silyated ketone [80] may then be deprotected and oxidized in the conventional manner (Scheme I, Scheme $H_1$ [35] to [36], respectively) to give the alkylated dione [81]. The alkylated dione [81] is then converted into the seco acid (ring cleaving) and ring closure in the typical manner, as described in Scheme C to give the aza-dione [82].

Scheme $O_2$ represents the second part of the synthesis of the 15-alkyl compounds of the invention. The aza-dione [82] can be directly converted (Route B) into the desired cyclopropyl ether [84A] (Option A) or cyclopropylamine (Option B) [84B] in the conventional manner (Scheme A and Scheme C, respectively). Alternatively, the aza-dione can be hydrogenated (Route A), under typical conditions (Scheme N) to give the 15-alkyl-aza-androstane [83], which can be converted into either the cyclopropylether [84] or cyclopropylamine [84] as described before.

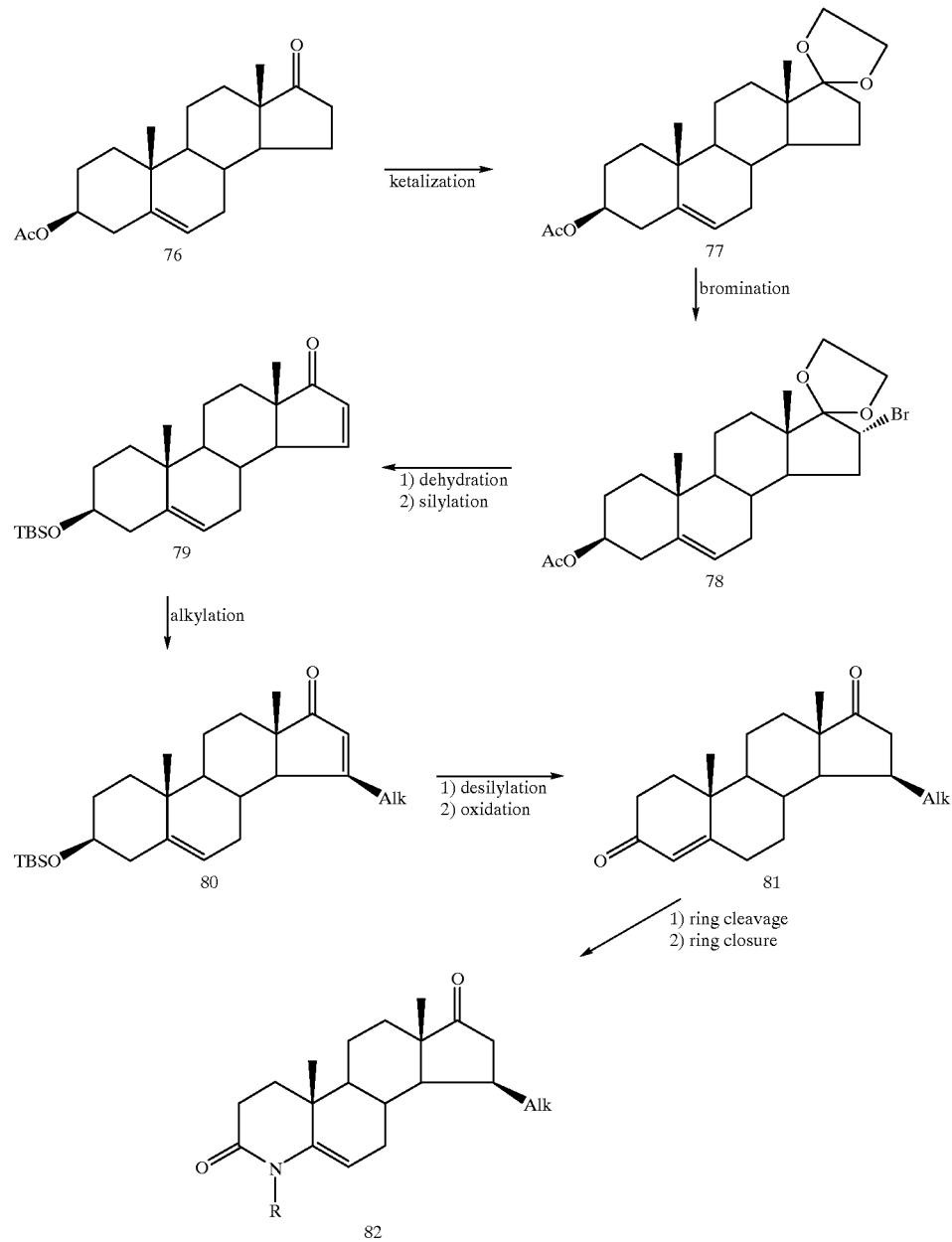

Scheme $O_1$

Scheme O₂

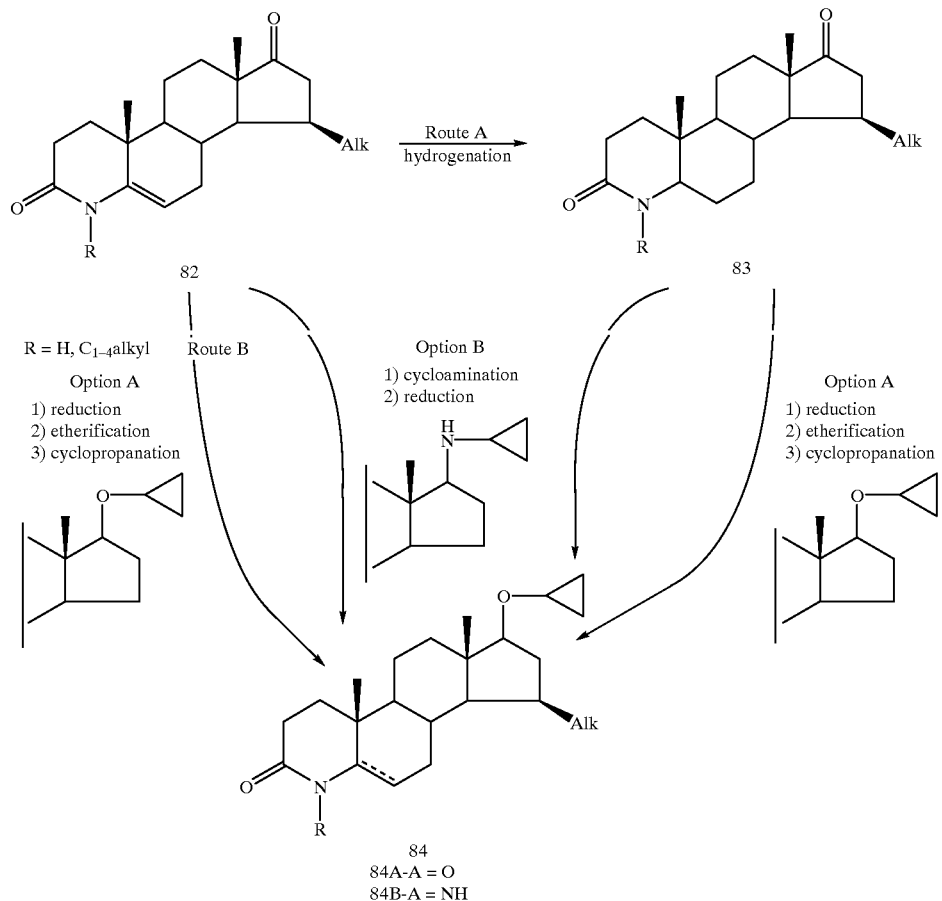

7-alkyl Compounds

The 7-alkyl compounds of the invention may be prepared in a manner analogous to that described in PCT applications PCT/US/04643 (WO 93/23420) and PCT/US/04734 (WO 93/23039) the disclosures of which are hereby incorporated by reference.

7-alkenyl, Carboxy and Methyl Carboxy

The compounds of the invention wherein there is an alkenyl, carboxy or methylcarboxy substitent at the 7-position may be prepared in a manner analogous to that presented in PCT applications PCT/US/04643 (WO 93/23420) and PCT/US/04734 (WO 93/23039) the disclosures of which are hereby incorporated by reference.

2-halogenated

The compounds of the invention wherein there is a halogen substituent at the 2-position may be prepared by the method described in European Patent Application 0473225 A2 (91-202135), the disclosure of which is herein incorporated by reference.

2-halo, R-thio, R-sulfinyl-, R-sulfonyl

The compounds of the invention wherein the above 2-substituents are present may be prepared in a manner analogous to that described in European patent application 0473226 A2 (91–202135), the disclosure of which are herein incorporated by reference.

$\Delta^1$ dehydrogenation $\Delta^1$ dehydrogenation by DDQ in the presence of a silyated agent bistrimethylsilyltrihaloacetamide, hexamethyldisilane or bistrimethylsilylurea are described in U.S. Pat. No. 5,116,983, the disclosure of which is herein incorporated by reference.

15-alkyl

The compounds of the invention wherein the there is a 15-alkyl substitution may be prepared in a manner analogous to that reported in PCT Application No. PCT/US94/02697 (WO 94/20114), the disclosure of which is herein incorporated by reference.

BIOLOGICAL METHODS & RESULTS

The following abbreviations are hereafter employed:

NADPH=hydrogenated nicotinamide adenine dinucleotide phosphate

DMSO=dimethylsulfoxide

EDTA=ethylenediaminetetraacetic acid

In vitro $C_{17,20}$ lyase assays: Compounds were tested for inhibition of cynomolgus monkey $C_{17,20}$ lyase in vitro using microsomal preparations of the enzyme from testicular tissue. Testes were removed from anesthetized animals and flash frozen in liquid nitrogen. Microsomes were isolated as described in Schatzman et al., *Anal. Biochem.* 175, 219–226 (1988). The compound to be tested was dissolved in dimethyl sulfoxide and diluted in 0.05 M potassium phosphate buffer, pH 7.4, to give the desired concentrations of test compound, in an amount which contributed 0.1% v/v DMSO to the total assay volume. Assays contained 0.05 M potassium phosphate buffer, pH 7.4, an NADPH regenerating system (1 mM NADPH, 5 mM glucose-6-phosphate, 1 IU/mL glucose-6-phosphate dehydrogenase), test compound, substrate and microsomal protein in a total volume of 0.2 mL. Control assays contained all components, including dimethyl sulfoxide, but not test compound. All assays were performed in duplicate. The test compound was incubated with 20 to 62 μg/mL microsomal protein, buffer, and the NADPH regenerating system described above at 34° C. for 0 or 40 minutes. Aliquots of 180 μL were then removed and assayed for enzyme activity by addition to 7-[$^3$H]-17α-hydroxypregnenolone (11.2 mCi/mmole; 0.2 μCi per assay) plus unlabeled 17α-hydroxypregnenolone dissolved in DMSO, contributing 2.5% v/v to the final assay mix, and phosphate buffer to give a total substrate concentration of 0.05 μM (=Km) per assay and subsequent incubation at 34° C. for 6 minutes. Each assay was terminated by addition of 5 mL of chloroform:methanol (2:1). Carrier steroids representing substrates and products (17α-hydroxypregnenolone, dehydroepiandrosterone, and androst-5-ene-3β, 17β-diol) and 0.8 mL of distilled, deionized water were also added at this time. The steroids were extracted by the method of Moore and Wilson (*Methods in Enzymol.*, eds. O. Malley, B. W. and Hardman, J. G. 36, 1975, pp. 466–474). The organic phase containing the steroids was evaporated using nitrogen gas, the residues dissolved in 18% tetrahydrofuran (v/V) in hexane, and the steroids were separated by HPLC on a Si60 (5 μm) column (250×4 mm) using a gradient of 18–22% tetrahydrofuran (v/v) in hexane. Radioactivity in the steroid peaks was measured using a Radiomatic® Model HS or Model A515 Flo-One® detector.

The enzyme activity for each assay was calculated from the percent conversion of substrate to products, and the results were expressed as percent inhibition of control. The following results were obtained, wherein the values indicated are the mean of duplicate determinations:

TABLE 1

In Vitro $C_{17,20}$ Lyase Inhibition

| Compound | Conc. (μM) | Preincubation time (min.) | % Inhibition |
|---|---|---|---|
| MDL 103,129 | 10 | 0 | 77.3 |
|  |  | 40 | 84.3 |
|  | 1 | 0 | 40.7 |
|  |  | 40 | 46.9 |
|  | 0.1 | 0 | 6.4 |
|  |  | 40 | 18.3 |
| MDL 103,432 | 10 | 0 | 68.3 |
|  |  | 40 | 80.2 |
|  | 1 | 0 | 33.0 |
|  |  | 40 | 54.2 |
|  | 0.1 | 0 | 23.4 |
|  |  | 40 | 20.2 |
| MDL 103,496 | 10 | 0 | 39.2 |
|  |  | 40 | 87.7 |
|  | 1 | 0 | 29.0 |
|  |  | 40 | 62.2 |
|  | 0.1 | 0 | 5.0 |
|  |  | 40 | 26.6 |
| MDL 104,313 | 10 | 0 | 63.6 |
|  |  | 40 | 70.2 |
|  | 1 | 0 | 23.8 |
|  |  | 40 | 39.9 |
|  | 0.1 | 0 | −18.4 |
|  |  | 40 | −8.7 |
| MDL 105,831 | 10 | 0 | 69.6 |
|  |  | 40 | 100 |
|  | 1 | 0 | 26.0 |

TABLE 1-continued

In Vitro $C_{17,20}$ Lyase Inhibition

| Compound | Conc. (μM) | Preincubation time (min.) | % Inhibition |
|---|---|---|---|
|  |  | 40 | 53.8 |
|  | 0.1 | 0 | 11.4 |
|  |  | 40 | 24.6 |

LEGEND:
MDL 103,129 = 17β-Cyclopropyloxy-4-aza-5α-androst-1-en-3-one
MDL 103,432 = 17β-Cyclopropyloxy-4-aza-5α-androstan-3-one
MDL 103,496 = 17β-Cyclopropyloxy-4-aza-androst-5-en-3-one
MDL 104,313 = 17β-Cyclopropyloxy-4-methyl-4-aza-androst-5-en-3-one
MDL 105,831 = 17β-Cyclopropylamino-4-aza-androst-5-en-3-one In vitro 5α-reductase assays: The activity of the present compounds as inhibitors of steroid 5α-reductase was determined using microsomal preparations of the 5α-reductase enzyme from laboratory animal prostate tissue. Specifically, microsomes were isolated from cynomolgus monkey prostate tissue. Protein concentration of the microsomal preparations was determined prior to use of the samples. Individual assays of cynomolgus monkey prostatic 5α-reductase activity contained 0.1 M potassium phosphate-sodium citrate buffer, pH 5.6 1.0% (w/v) bovine serum albumin, 1.0 mL sodium EDTA, 4 μg of microsomal protein, 1.0 mM NADPH, 5.0 mM glucose-6-phosphate, 1 IU/mL glucose-6-phosphate dehydrogenase, [1,2-$^3$H]-testosterone (0.15 μCi) plus unlabeled testosterone to yield 0.015 μM (Km= 0.015 μM to 0.09 μM in multiple determinations), and test compound which was dissolved in DMSO then diluted in 0.1 M potassium phosphate-sodium citrate buffer, pH 5.6, to yield a final assay concentration of 0.1% (v/v) DMSO. The same buffer and DMSO without test compound were used in control assays. Background radioactivity was determined from assays containing all components except enzyme. Assays were performed in duplicate. Microsomes, 0.1 M potassium phosphate-sodium citrate buffer, pH 5.6, and test compound were preincubated at 37° C. Aliquots of 180 μL were removed after 0 or 40 minutes of preincubation and added to 20 mL of testosterone substrate suspended in 0.1 M potassium phosphate-sodium citrate buffer, pH 5.6, containing 10% (v/v) DMSO. Remaining enzyme activity was assayed for 10 minutes at 37° C. in a Dubnoff shaker incubator.

The reactions were terminated by the addition of 5 mL CHCl$_3$:methanol (2:1) and 0.9 mL water. Carrier steroids were added in the form of 2.5 μg each of testosterone, dihydrotestosterone, and 3,17-androstanediol. Steroid metabolites were then extracted according to the procedure of Moore and Wilson (Methods in Enzymol., O'Malley, B. W. and Hardman, J. G. eds., 36, 1975, pp. 466–474), the organic phase containing the steroids was evaporated using nitrogen gas, the residues were dissolved in 3% (v/v) isopropanol in hexane. The steroids were then seperated by normal phase HPLC on a LiCrosorb® DIOL derivatized silica gel column (10 μm; 4×250 mm) with a 3% to 7% isopropanol in hexane gradient, followed by isocratic conditions of 75% (v/v) isopropanol in hexane. Radioactivity in the steroid peaks was measure using a Packard Radiomatic model HS Flo-One® detector. When the compound were tested using the above procedures with cynomolgus monkey 5α-reductase, the following results were obtained:

TABLE 2

In Vitro 5α-Reductase Inhibition Results

| Compound | Conc. (μM) | Preinc., time (min.) | % Inhibition |
|---|---|---|---|
| MDL 103,432 | 10 | 0 | 99.4 |
|  |  | 40 | 99.4 |
|  | 1 | 0 | 98.7 |
|  |  | 40 | 99.3 |
|  | 0.1 | 0 | 78.7 |
|  |  | 40 | 80.0 |
| MDL 103,496 | 10 | 0 | 99.6 |
|  |  | 40 | 99.4 |
|  | 1 | 0 | 86.2 |
|  |  | 40 | 86.7 |
|  | 0.1 | 0 | 24.6 |
|  |  | 40 | 29.5 |

*NOTE:
Values are the mean of duplicate determinations
See Table 1 for chemical names Ex vivo inhibition of $C_{17,20}$ lyase: MDL 103,432 was tested for ex vivo inhibition of rat and nude mouse testes layse. Male Copenhagen rats and male athymic nude mice obtained from Harlan Laboratories, Indianapolis, Ind., were divided into groups of 5 to 6 based on weight. Average weight was 100–140 g each for rats and 18–35 g each for the mice. Prior to oral dosing, animals were fasted overnight. Test compound was prepared by micronization in a lecithin vehicle using a glass Teflon® pestle-type homogenizer. The compound was brought to volume using lecithin so as to administer 0.5 mL per 100 g animal. Rats and nude mice were given vehicle only (controls) or vehicle plus test compounds per os. Rats were also given the compound in lecithin or lecithin alone subcutaneously. Each group consisted of 5–6 animals. At a specified time after dosing, the animals were anesthetized with $CO_2$ gas, sacrificed by cervical dislocation, testes were excised, capsules were removed, and the tissue was weighed. Two volumes (w/v) of 0.05 M potassium phosphate buffer, pH 7.2, was added to the rat testes tissue on ice, and 11 volumes (w/v) of the same buffer were added to the mouse testes. Tissue was then homogenized using 20 strokes with a Dounce homogenizer equipped with a tight pestle. Homogenized tissue was centrifuged at 800×G then at 10,000×G for 15 minutes each. Supernatant was decanted, reserved, and kept chilled on ice. Assays for lyase activity contained the same buffer and NADPH regenerating system described above and also contained 120 μL of 10,000×G supernatant which was diluted 3-fold resulting in a 5-fold dilution overall in the final assay volume. Substrate, 17α-hydroxyprogesterone plus 1,3-[$^3$H]-17α-hydroxyprogesterone (40–57 mCi/mmole; 0.18 μCi per assay) to yield a final concentration of 0.1 μM, (=Km) was added to the remaining assay components after a 5 minute equilibration a 20° C. of the latter. The total assay volume was 200 μL. Activity was assayed for 20 seconds at 20° C.

Nude mouse testes lyase was assayed by the same procedure described for the rat enzyme above except that the 10,000×g supernatant was diluted 12-fold in phosphate buffer, and 60 μL of this was used in the assay resulting in a 40-fold overall dilution of the supernatant. The substrate concentration was 0.04 μM (Km=0.03 μM), and the assays were incubated at 15° C. for 30 seconds.

Assays were terminated, extracted and analyzed as described above except that carrier steroids were 17α-hydroxyprogesterone, androst-4-ene-dione, and testosterone. The organic phase containing the steroids was evaporated using nitrogen gas, the residues dissolved in 18% tetrahydrofuran (v/V) in hexane, and the steroid substrate, 17α-hydroxyprogesterone, and products (AED, TEST) were separated by HPLC on a Si60 (5 μm) column (250×4 mm) using 20% (v/v) tetrahydrofuran (THF) in hexane for 20 minutes then ramping to 60% THF (v/v) for 11 minutes. Activity of test compound was expressed as percent inhibition relative to the control and was the mean of each group of treated animals.

Using the method described above, MDL 103,432 inhibited nude mouse testicular $C_{17,20}$ lyase activity by 88% at 30 mg/kg and 96% at 100 mg/kg 4 hours after oral dosing. Rat testicular $C_{17,20}$ lyase activity was inhibited by MDL 103,432 as shown below:

TABLE 3

Ex Vivo $C_{17,20}$ Lyase Inhibition Results

| Dose | Time (hr) | Route | % Inhibition |
|---|---|---|---|
| 50 mg/kg | 4 | p.o. | 66.4 |
| 50 mg/kg | 24 | p.o. | 52.7 |
| 50 mg/kg | 4 | s.c. | 32.9 |
| 50 mg/kg | 24 | s.c. | 40.7 |

In vivo data:
Dunning H Tumor

As described in J. T. Isaacs & D. S. Coffey, *Cancer Res.* 41:6070–5075 (1981); W. J. Ellis & J. T. Issacs, *Cancer Res.* 45:6041–6050 (1985); T. W. Redding & A. V. Schally, *The Prostate* 6;219–232 (1985) and P. E. Juniewicz et al. *The Prostate* 18:105–115 (1991), male Copenhagen rats were obtained from HARLAN-SPRAGUE-DAWLEY Inc. (Indianapolis, Ind.), and were individually housed in suspended wire cages and provided laboratory rodent chow (Purina 5001] pellets, Purina Mills, St. Louis, Mo.) and deionized water adlibum. The rats were anesthetized using sodium pentobarbital and the hair was clipped from the back dorsal area. Tumors from donor Copenhagen rats were cut into fragments of 10 mm$^3$ and implanted subcutaneously (one site per rat) into the prepared dorsal area.

Figure 6:
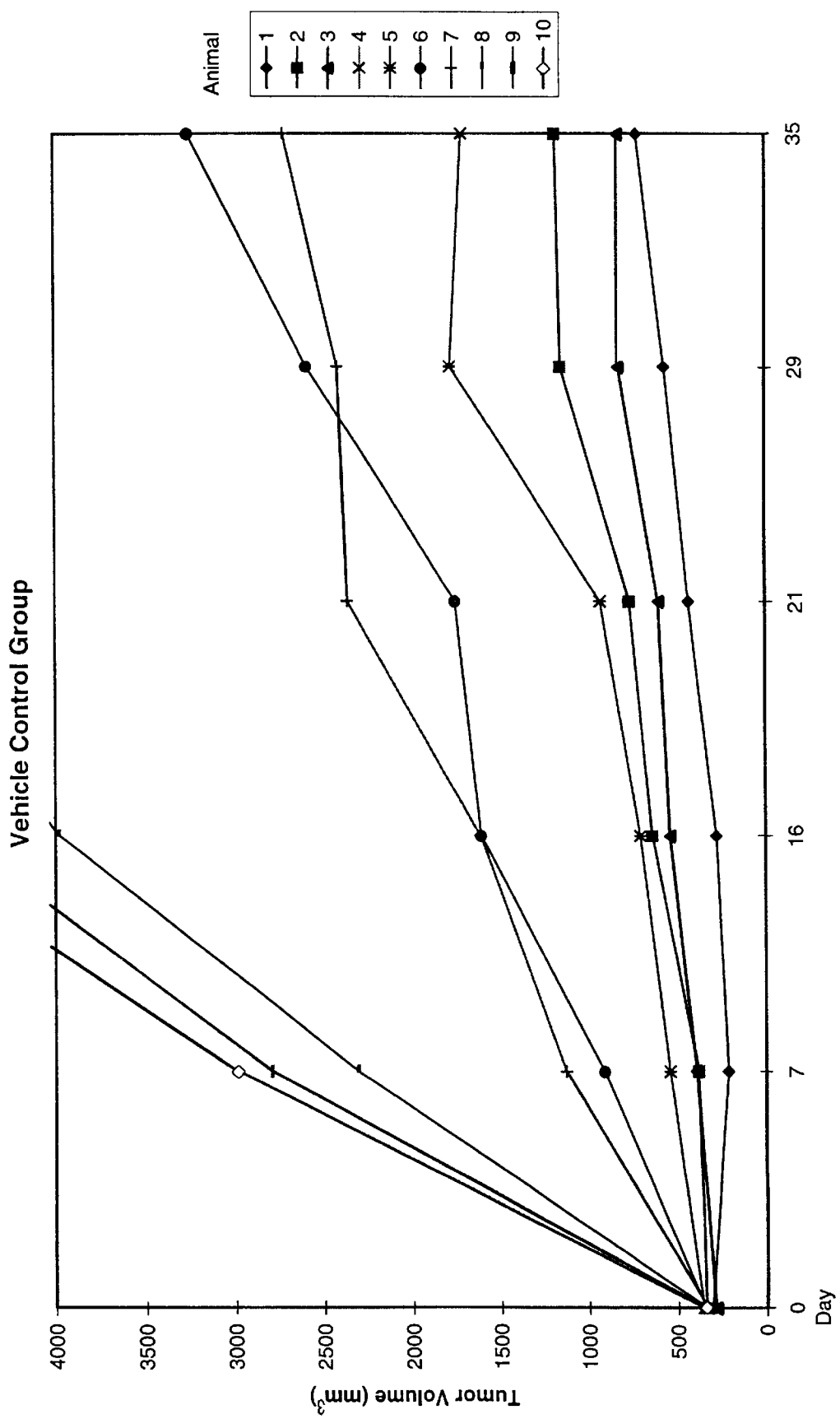
FIG. 6 Illustrates the tumor volume for individual animals over time of the vehicle control group in the Dunning H rat assay.
Figure 7:
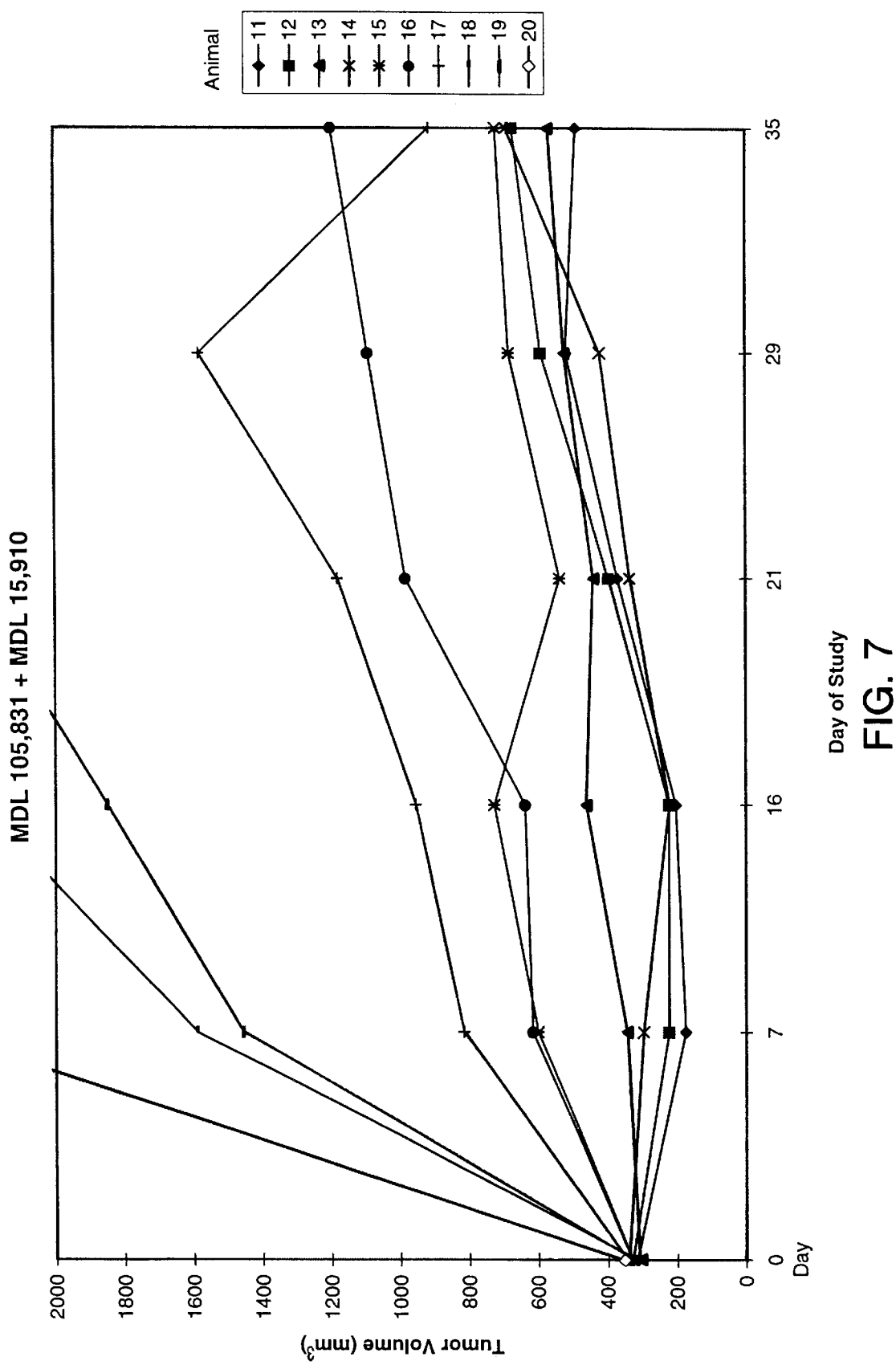
FIG. 7 Illustrates the tumor volume for individual animals over time of the group administered a combined therapy of MDL 105,831 and MDL 15,910 (flutamide) in the Dunning H rat assay.
Figure 8:
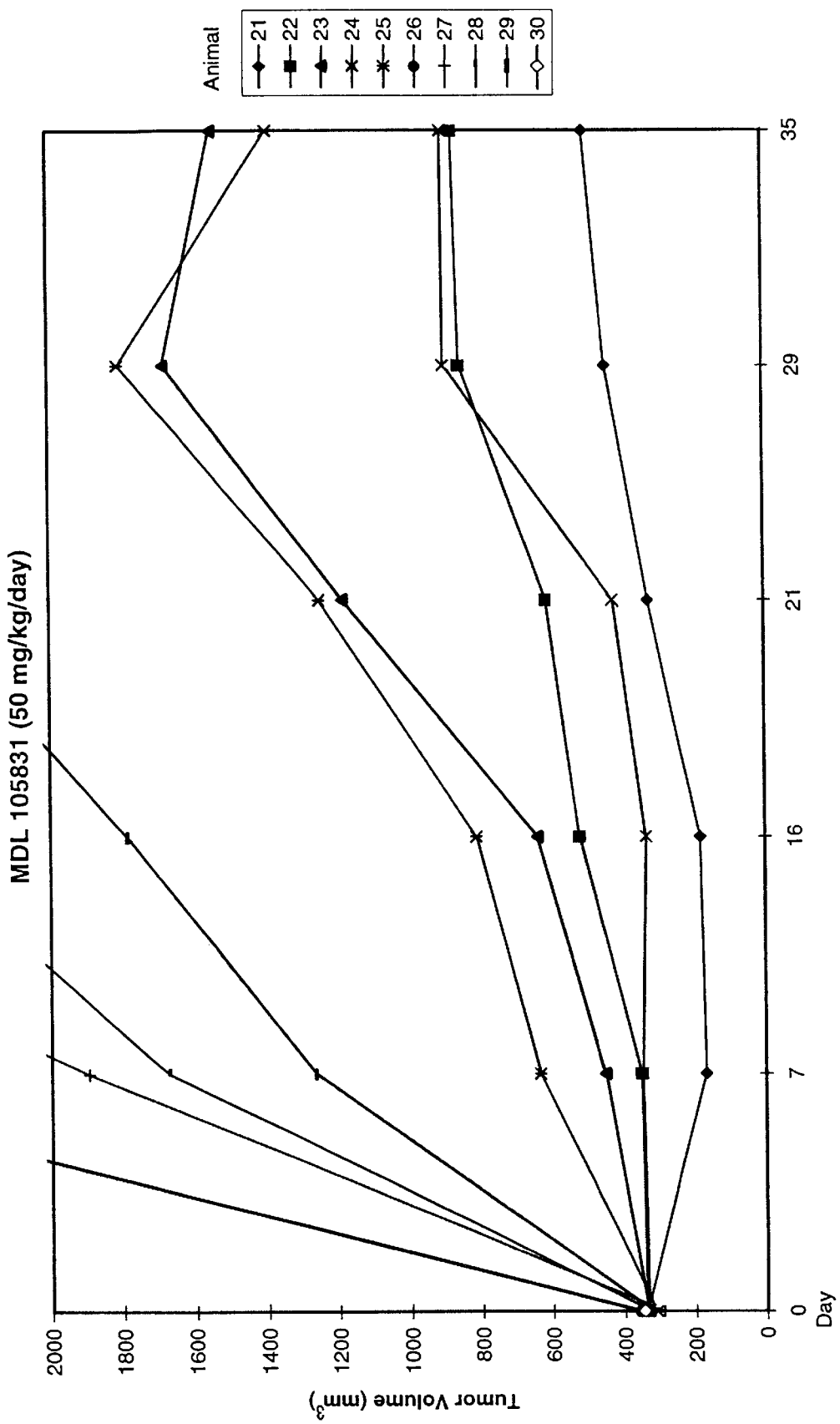
FIG. 8 Illustrates the tumor volume for individual animals over time of the group administered compound MDL 105, 831 in the Dunning H rat assay.
Figure 9:
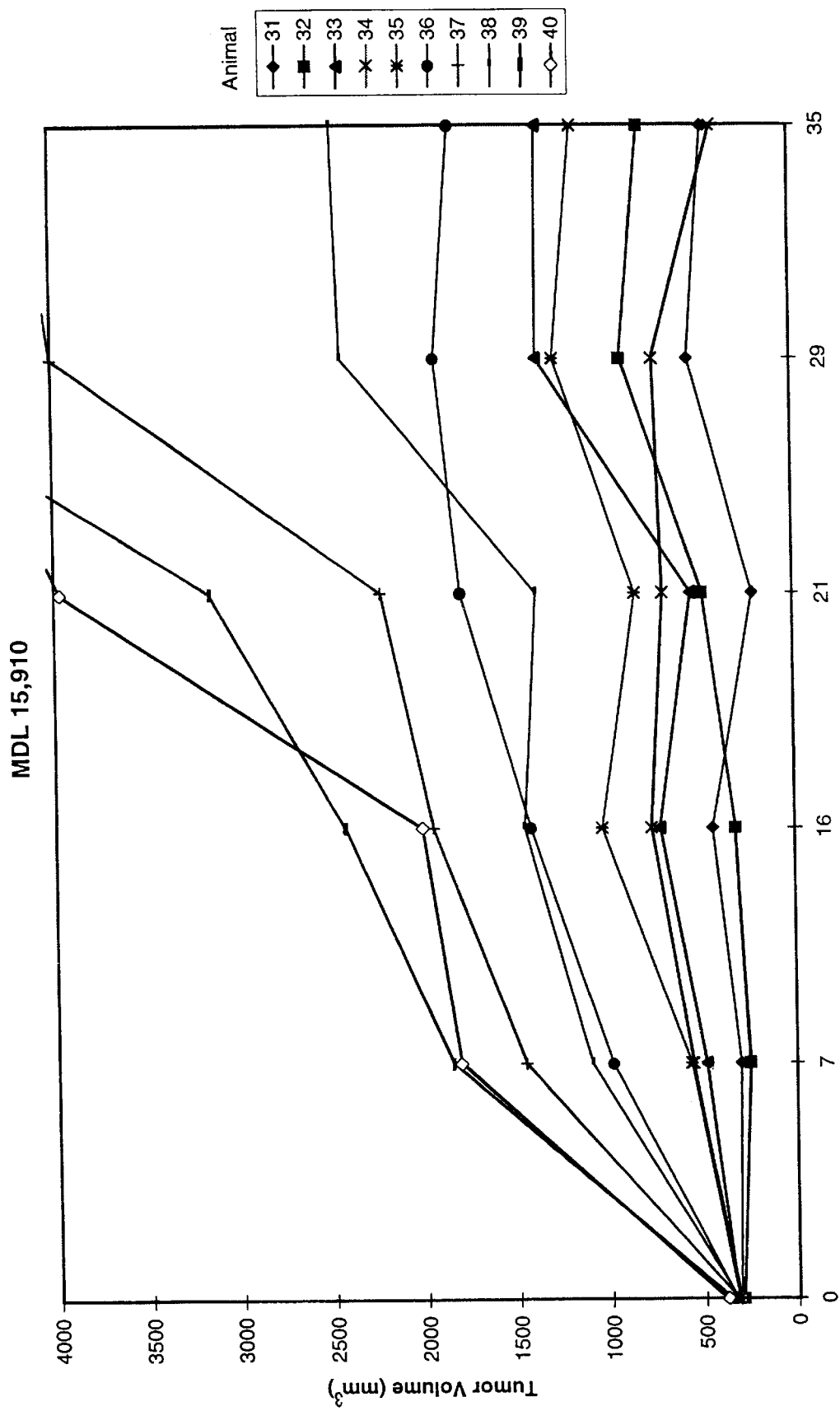
FIG. 9 Illustrates the tumor volume for individual animals over time of the group administered compound MDL 15,910 (flutamide) in the Dunning H rat assay.
Figure 10:
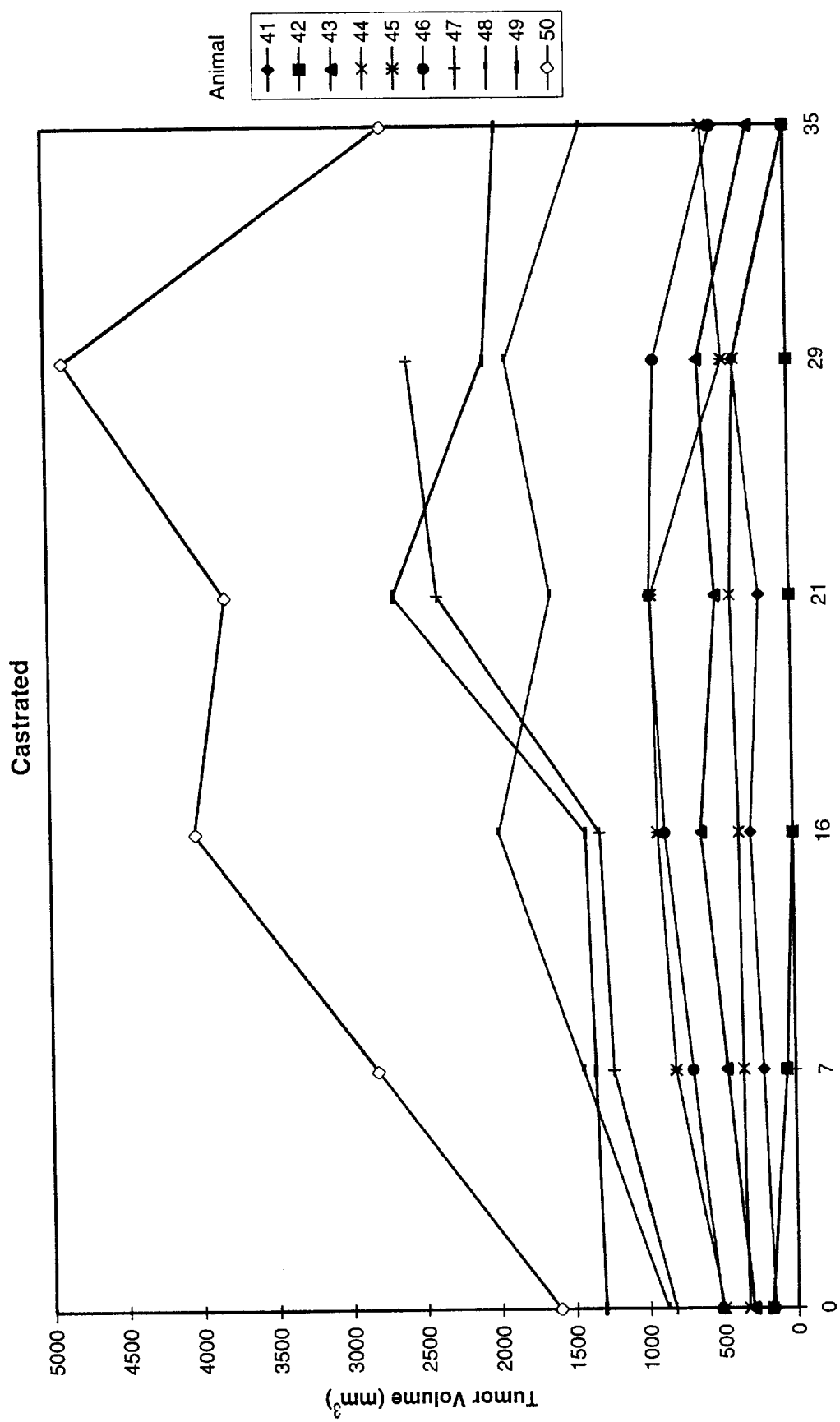
FIG. 10 Illustrates the tumor volume for individual animals over time of the castrated group in the Dunning H rat assay.

Animals were selected (105 days post implantation) for the treatment phase based on tumor size. Ten animals were anesthetized with sodium pentobarbital and bilaterally castrated. The remaining animals were assigned to treatment groups (ten per group) based on mean group tumor size. Animals were kept separate throughout the study. The tested compounds were prepared in solution or suspension in a lecithin vehicle (L-α-phosphatidycholine type XV-E) containing methylparaben and propylparaben. All treatments were performed by oral gavage (per os) at 2 cc/kg each day of study. Tumor size and rat body weights were recorded every seven days over a period of 35 days. Twenty-four hours after the last treatment animals were euthenized by $CO_2$ and the tumors, prostate, seminal vesicles and testes were removed and weighed. In Table 4, average tumor growth is determined from the corrected group means over a 35 day period after treatment was started. The correction was determined by first eliminating those animals from each data set which exhibited grossly disproportionate growth relative to the other animals in the treatment group. As these tumors were in-fact rat sarcomas, and the phenomenon was observed in all of the compound treated animals, such disproportionate growth is believed to be a limitation indemic to this model. The animals eliminated from the calculation of the corrected means were in FIG. 6, animals 8, 9, 10; in FIG. 7, animals 18, 19 and 20; in FIG. 8, animals 27, 28, 29 and 30; and in FIG. 9, animals 37, 39 and 40. The castrated controls in FIG. 10 present a different problem. Here it is believed that the different tumor volumes observed throughout the group is attributable to the different sizes at the beginning of the study. Since the mean variance here is clearly attributable to factors other than the effect of the castration itself, animals 47, 48, 49 and 50 were deleted from the corrected mean. Of these, animal 47 died during the treatment period.

Table 4 indicates the average daily growth rate, measured from the corrected mean tumor size on day 35 and day 0, comparing MDL 10583 and flutamide (MDL 15910), a known androgen receptor antagonist. MDL 10583 is shown to have similar tumor suppression properties as flutamide which is additive when combination therapy is employed.

Animals were selected for treatment groups based on tumor size. Each test compound was prepared as a solution or suspension in a lecithin vehicle (L-α-phospha-tidycholine type XV-E) containing methylparaben and propylparaben at a dose volume of 10 cc/kg. Animals were treated for 42 days by oral gavage (per os) seven days per week. Twenty-four hours after the last treatment the animals were euthenized by $CO_2$ and tumors were removed and weighed. During the study period, mice were weighed and palpated weekly for tumors. In Table 5, average tumor growth is determined from the corrected group means over a 28 day period after treatment was started. The correction was determined by first eliminating those animals from each data set which exhibited grossly disproportionate growth relative to the

TABLE 4

Tumor Growth in Dunning H Rat ($mm^3$)

| Treatment Group | Day | | | | | | Δv/Δt |
|---|---|---|---|---|---|---|---|
| | 0 | 7 | 16 | 21 | 29 | 35 | (day 35 ± day 0) |
| Vehicle control | 327.83 | 594.75 | 898.67 | 1143.17 | 1556.33 | 1735.67 | 40.22 $mm^3$/day |
| Castrated control | 330.17 | 429.58 | 508.50 | 501.00 | 450.83 | 220.33 | −3.14 $mm^3$/day |
| MDL 105831 & MDL 15910 | 326.57 | 439.38 | 489.00 | 606.43 | 773.00 | 750.43 | 12.11 $mm^3$/day |
| MDL 105831 | 328.40 | 389.90 | 497.20 | 759.40 | 1135.80 | 1041.60 | 20.38 $mm^3$/day |
| MDL 15910 | 317.00 | 604.64 | 877.86 | 851.29 | 1313.57 | 1214.57 | 25.64 $mm^3$/day |

LEGEND:
MDL 105831 = 17β-cyclopropylamino-4-aza-androst-5-en-3-one (15 mg/kg/day PO)
MDL 15910 = N-(3-Trifluoromethyl-4-nitro-phenyl)-isobutyramide (50 mg/kg/day PO)

Figure 2:
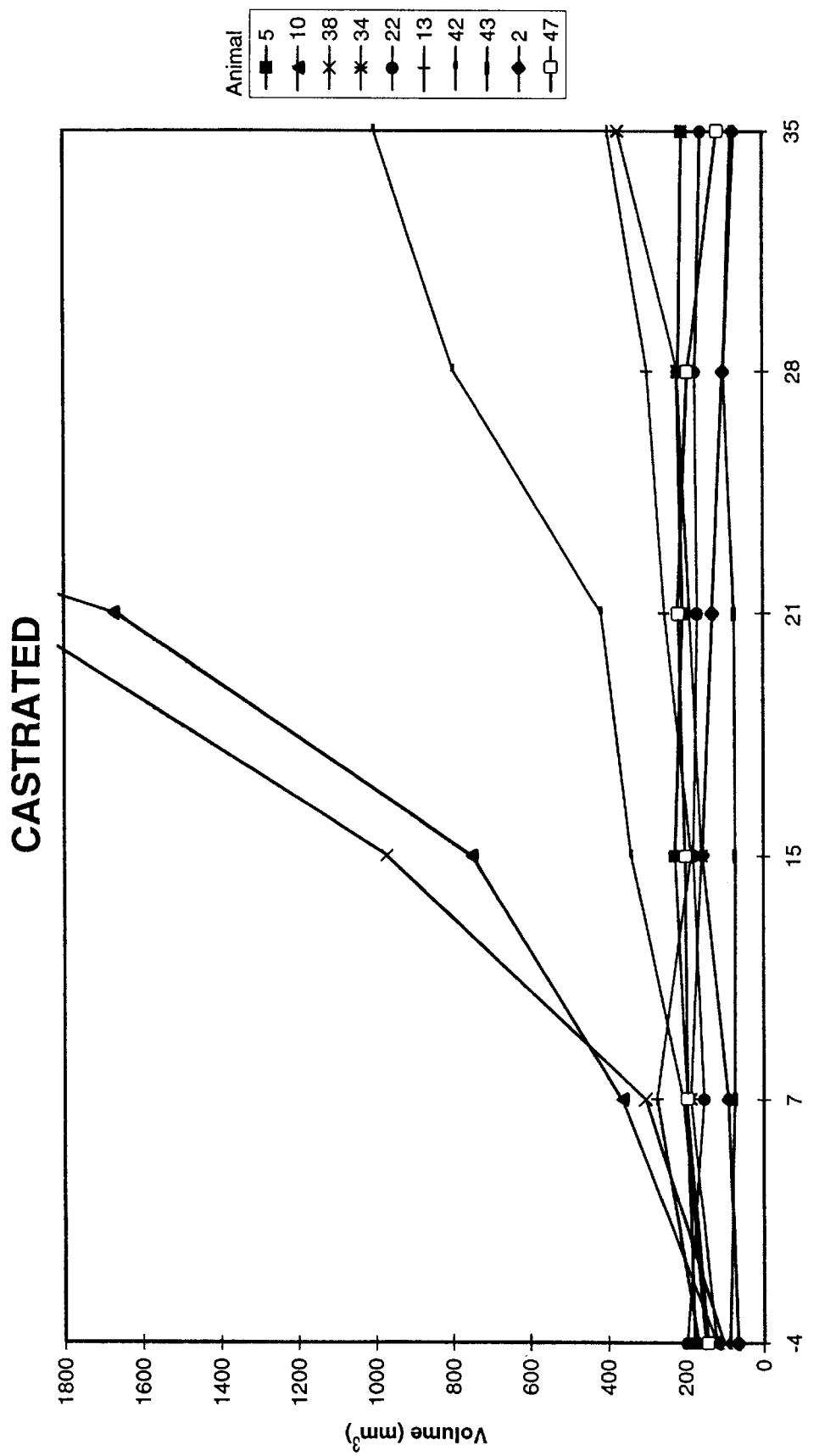
FIG. 2 Illustrates the tumor volume for individual animals over time of the castrated group in the PC-82 nude mouse assay.
Figure 3:
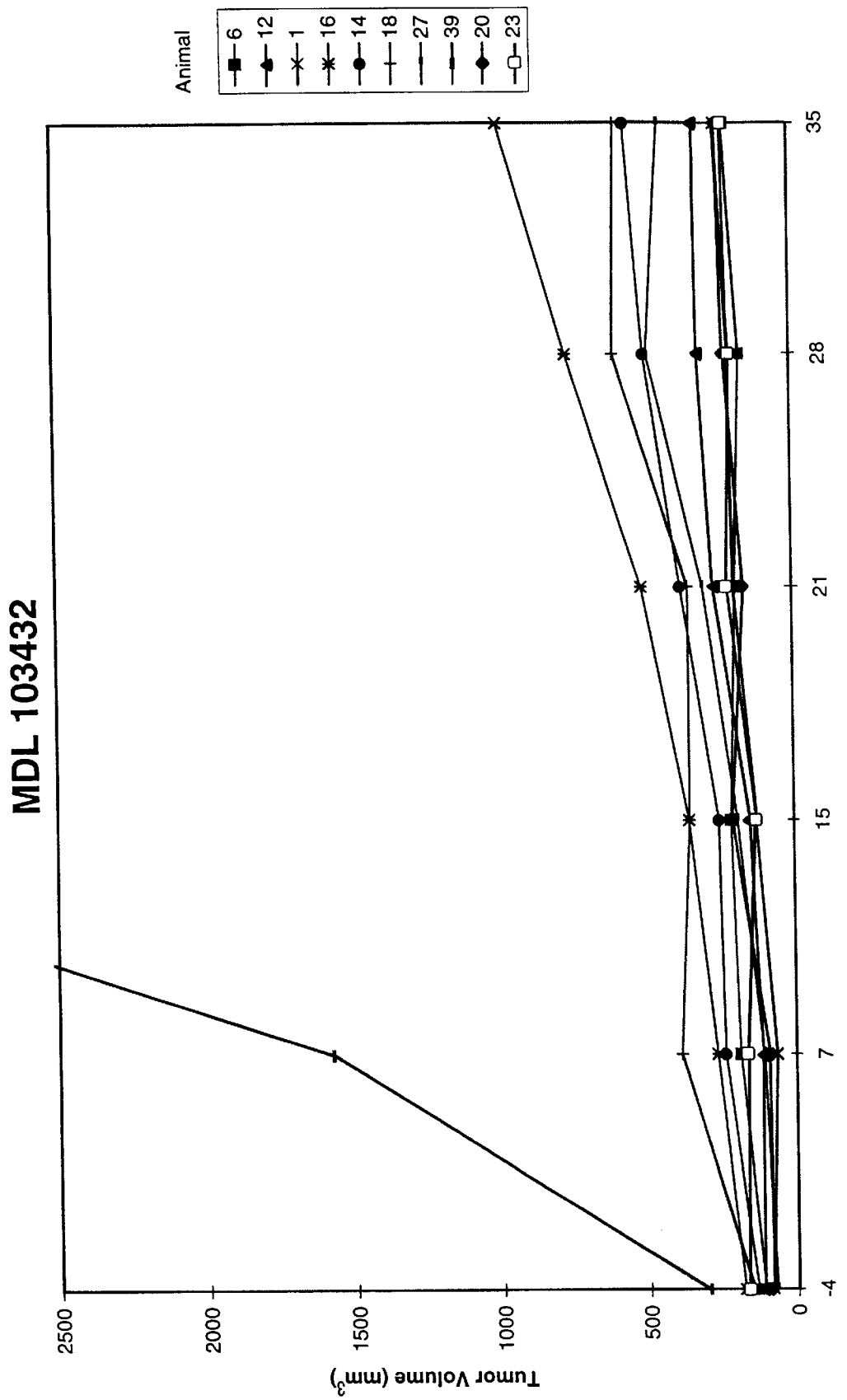
FIG. 3 Illustrates the tumor volume for individual animals over time of the group administered compound MDL 103432 in the PC-82 nude mouse assay.
Figure 4:
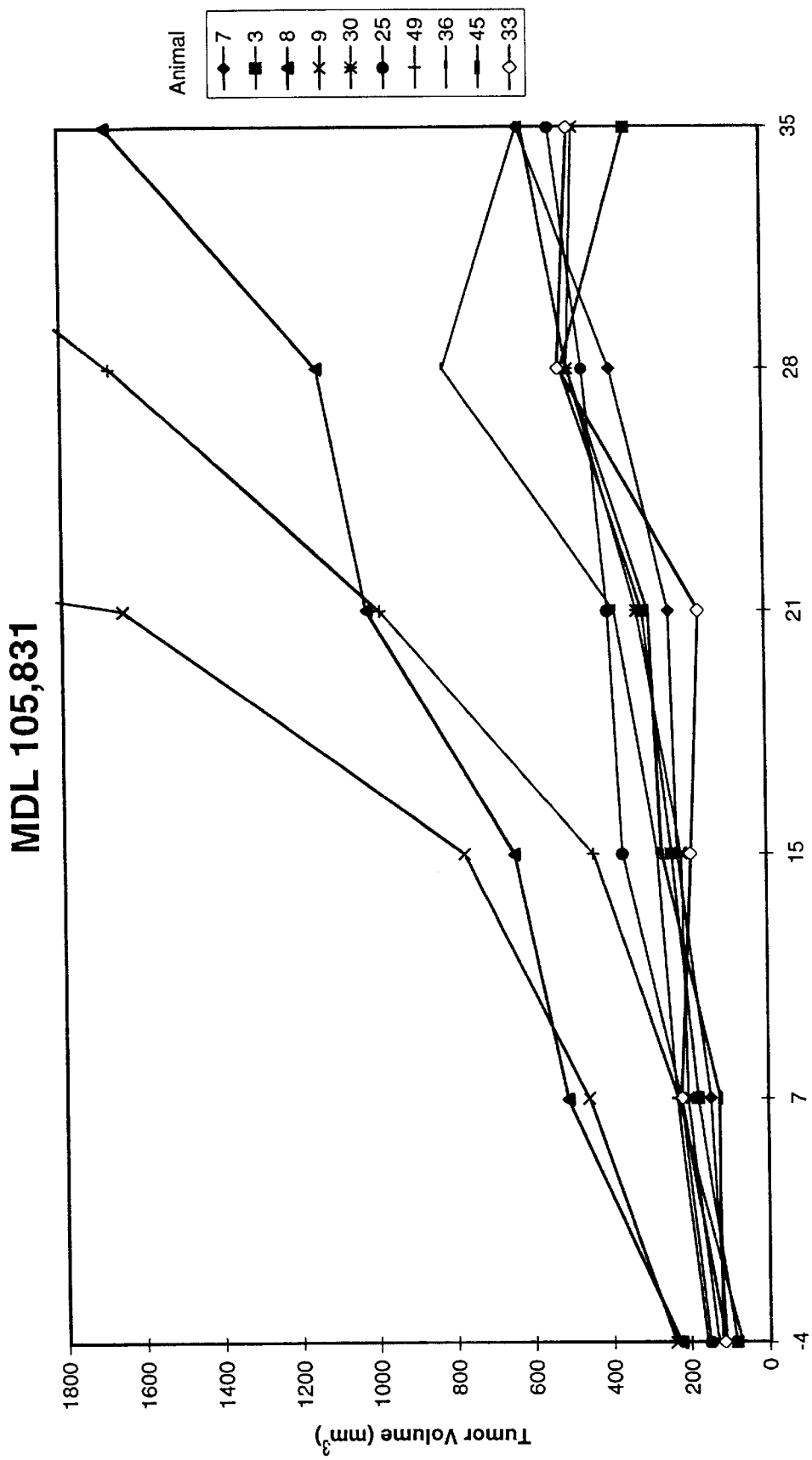
FIG. 4 Illustrates the tumor volume for individual animals over time of the group administered compound MDL 105,831 in the PC-82 nude mouse assay.
Figure 5:
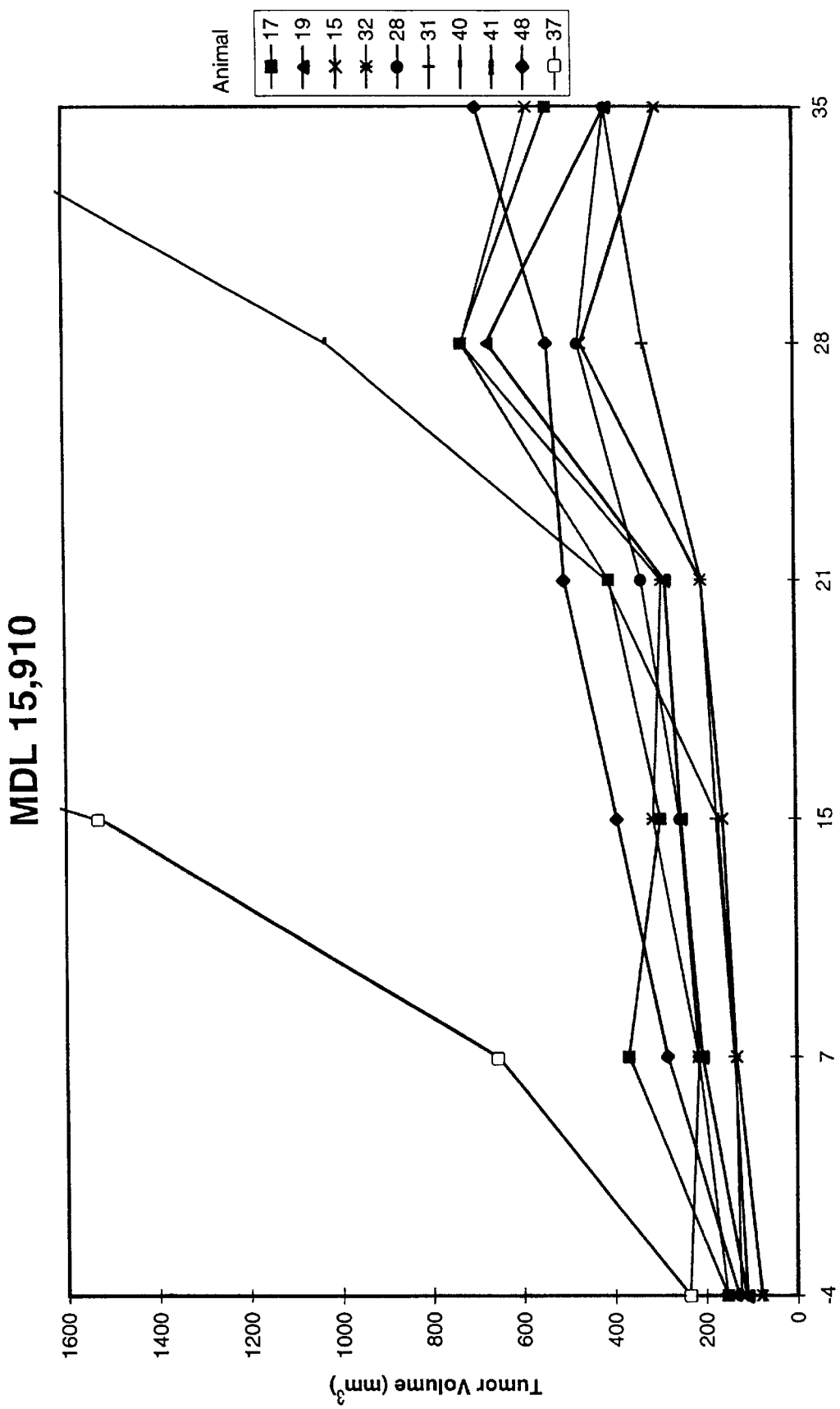
FIG. 5 Illustrates the tumor volume for individual animals over time of the group administered compound MDL 15,910 (flutamide) in the PC-82 nude mouse assay.

PC-82 Tumors in Nude Mice:

As described in van Steenbrugge, G. J. et al., *J. Urol* 131: 812–817 (1984) van Steenbrugge G. J. et al., *The Prostate* 11: 195–210 (1987) and Redding, T. W. et al., *Cancer Research* 52, 2538–2544 (1992), male nude mice (Hsd:athymic, Nude-nu) were obtained from Harlan Sprague Dawley. Mice were housed in sterilized micro-isolators and fed autoclaved ABLE® rodent chow (Purina Mills Inc., St. Louis, Mo.) and deionized water, ad libitum. Tumor-donating mice were first anesthetized using sodium pentobarbital and then sacrificed by cervical dislocation. The tumor was subsequently excised and placed in a petri dish containing ice-cold Hanks balanced salt solution. Tumors were cut into 2–3 mm cubes for implantation. Recipient animals were first anesthetized with 50 mg/kg pentobarbital, then implanted, by use of a trocar, with tumor fragments (one per mouse) in the dorsal area. Animals were separated into two control groups, one with vehicle alone and the other castrated, and the treatment groups, where n is the number of animals in each group.

other animals in the treatment group. Such tumor growth is believed to result from conversion of the tumor into a non-androgen dependent sarcoma and most often resulted in euthanasia of the subject before the end of the treatment period. The following animal data was deleted before computation of the corrected mean data in Table 5, FIG. 1: animals 4 and 44; FIG. 2: animals 10, 38 and 42; FIG. 3: Animal 39; FIG. 4: Animals 8, 9 and 49; FIG. 5: Animals 37 and 40 and 41.

Table 5 illustrates the average tumor growth in animals treated with 4-aza-17β-(cyclopropyloxy)-5α-androstan-3-one (MDL 103432; 50 mg/kg B.I.D.), 4-aza-17β-(cyclopropylamino)-5α-androst-5-ene-3-one (MDL 105831; 50 mg/kg B.I.D.) and flutamide (MDL 15,910; 15 mg/kg B.I.D.), a known androgen receptor antagonist. The average rate of each tested compound relative to the vehicle and castrated controls is consistent with the invivo inhibition of androgens.

TABLE 5

Tumor Growth in PC-82 Human Tumor in Male Nude Mice ($mm^3$)

| Treatment Group | Day | | | | | | Δv/Δt |
|---|---|---|---|---|---|---|---|
| | −4 | 7 | 15 | 21 | 28 | 35 | (day 35 − day 7) |
| Vehicle control | 142.0 | 245.2 | 281.9 | 413.4 | 505.9 | 604.1 | 12.82 $mm^3$/day |
| Castrated control | 135.9 | 164.7 | 165.9 | 174.9 | 165.5 | 199.9 | 1.26 $mm^3$/day |
| MDL 103432 | 122.2 | 180.2 | 220.2 | 288.2 | 385.9 | 427.4 | 8.83 $mm^3$/day |

TABLE 5-continued

Tumor Growth in PC-82 Human Tumor in Male Nude Mice (mm³)

| Treatment Group | Day | | | | | Δv/Δt |
|---|---|---|---|---|---|---|
| | -4 | 7 | 15 | 21 | 28 | 35 | (day 35 – day 7) |
| MDL 105831 | 124.9 | 188.3 | 254.3 | 304.3 | 530.7 | 531.1 | 12.24 mm³/day |
| MDL 15910 | 138.7 | 222.7 | 262.9 | 319.7 | 563.4 | 479.3 | 9.16 mm³/day |

EXAMPLES

The following examples are given to better illustrate the syntheses of particular compounds of the invention and should not be construed as limiting the invention in any way.

DEFINITIONS

In the following examples, unless otherwise noted: "room temperature" means 18° C.–23° C., any reference to "overnight" means 14–18 hours and soluted reagents are in aqueous solutions. The following formula abbreviations have also been employed:

brine = saturated aqueous of sodium chloride (NaCl)
THF = tetrahydrofuran          NaHCO$_3$ = sodium bicarbonate
EtOAc = ethyl acetate          CH$_2$Cl$_2$ = methylene chloride
MgSO$_4$ = magnesium sulfate   ether = diethyl ether (CH$_3$CH$_2$)$_2$O
HOAc = acetic acid             NH$_4$Cl = ammonium chloride
Na$_2$SO$_3$ = sodium sulfite

EXAMPLE 1

17β-cyclopropyloxy-4-aza-androst-5(6)-en-3-one

Example 1A

17β-hydroxy-5-oxo-4-nor-3,5-seco-androst-3-carboxylic acid

By a procedure analogous to that described by Milewich, L. & Axerrod, L., *Organic Synthesis, Collect. Vol. 6*, 1988, 690–91, testosterone (UPJOHN, 9.16297 g, 31.772 mmol) is dissolved into tert-butyl-alcohol (300 mL) in a 1000 mL 3-necked, round bottomed flask. Potassium carbonate (K$_2$CO$_3$) in water (75 mL) is added and the solution stirred until completely dissolved. The reaction flask is fitted with a 500 mL dropping funnel charged with sodium metaperiodate (NaIO$_4$, ALDRICH, 40.9249 g, 191.34 mmol) in water (350 mL). The reaction flask is also fitted with a separate 125 mL dropping funnel chared with a solution of potassium permanganate (FLUKA, KMnO$_4$, 0.80424 g, 5.089 mmol) in 50 mL water (50 mL).

About 50 mL of the metaperiodate solution and about 5 mL of the permanganate solution are added to the reaction mixture each in a single charge. The remainder of each solution are added dropwise over 30 minutes. After the completion of the additions, the reaction mixture is stirred an additional 90 minutes. The reaction is subsequently quenched by a slow addition of potassium bisulfite (K$_2$S$_2$O5, BAKER, 23.70107 g, 106.603 mmol) and stirring for 5 hours.

The reaction mixture is then filtered through through Celite® filter aid and stored overnight at room temperature. The filtrate is concentrated to about 250 mL under reduced pressure (45 mm Hg, 70° C.) and transferred to a 500 mL seperatory funnel. The concentrate is acidifed with 10% sulfuric acid (H$_2$SO$_4$, 26 mL) and extracted(3×200 mL) ether. The combined ethereal extracts are washed with 100 mL diethyl ether, then poured into 10% sulfuric acid (300 mL) in order to precipitate the product.

The precipitate is extracted (4×200 mL) with methylene chloride (CH$_2$Cl$_2$), the organic phases combined and washed with brine (100 mL), dried over MgSO$_4$, filtered and evaporated to dryness to give a white solid. The material was recrystallized overnight from about acetone (50 mL), collected by filtration, washed in hexane (30 mL) and dried under reduced pressure (0.3 mmHg, room temperature) for 4.5 hours to give 17β-hydroxy-5-oxo-4-nor-3,5-seco-androstane-3-arboxylic acid (6.1247 g). The compound has the following structure:

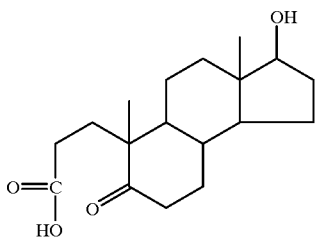

Alternatively, the 4-nor-3,5-seco-acid can be prepared in the following manner. Testosterone (9.1863 g) is dissolved in CH$_2$Cl$_2$ (70 mL) and diluted with methanol (100 mL). The solution is chilled to −78° C. under nitrogen. Ozone is then bubbled through the chilled solution for 25 minutes, after which the solution turns green. The atmosphere of the reaction vessel is purged with nitrogen, warmed to room temperature and the solvent evaporated. The residue in dissolved in ether (200 mL), extracted 3 times with 10% sodium hydroxide (NaOH, 50 mL), washed and the organic phases combined and washed again in ether (50 mL) and acidified with 10% sulfuric acid (H$_2$SO$_4$, 200 mL). The acidified solution is extracted in CH$_2$Cl$_2$, (4×50 mL) and the combined organic layers washed with brine dried over MgSO$_4$, filtered and evaporated to give the crude product as a white foam.

The crude product is taken-up in hot acetone (100 mL, ≈50° C.) and concentrated (~40 mL). The colorless crystals formed upon the cooling are collected and analyzed for purity to give 17β-hydroxy-5-oxo-4-nor-3,5-seco-androstane-3-carboxylic acid.

Example 1B

17β-acetoxy-4-aza-androst-5(6)-en-3-one

In a manner analogous to that disclosed in Kobyashi M. & Mitsuhashi, H., *Chem. Pharm. Bull.*, 1973, 21(5), 1069–1075, the seco-acid prepared above (4.0249 g, 13.051 mmol) and 10.26 g ammonium acetate (NH₄OAc, EM SCIENCE, 10.26 g, 133.1 mmol) are dissolved in HOAC (130 mL) and heated to relux temperature under nitrogen. After 5 days of refluxing, the reaction mixture is cooled to room temperature, then poured into water (800 mL). The resulting precipitate is collected by filtration and dried overnight at reduced pressure and room temperature (0.3 mm Hg).

The precipitate is recrystallized from ethanol by adding it to boiling ethanol (350 mL), concentrating (~180 mL) and drying (reduced pressure, room temperature) to give 17β-acetoxy-4-aza-androst-5(6)-en-3-one and corresponds to the chemical formula:

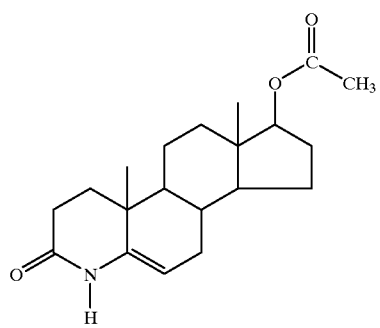

Example 1C

17β-hydroxy-4-aza-androst-5(6)-en-3-one

The 17β-ethyl carboxylate prepared in Example 1B (0.9259 g, 2.793 mmol) is dissolved in 60 mL warm ethanol/tetrahydrofuran (1:1), 6M sodium hydroxide is added (NaOH, 10.0 mL, 60 mmol) and the reaction is stirred at room temperature for 2 ½ hours. The reaction mixture is diluted with brine (100 mL) and extracted with EtOAc (3×50 mL). The combined organic phases are washed with brine (50 mL) and ammonium chloride (NH₄Cl), dried over magnesium sulfate, filtered and evaporated to give a crude reaction product. The crude product is recrystallized from ethanol to give colorless crystals (0.3132 g, 1.0822 mmol) of 17β-hydroxy-4-aza-androst-5(6)-en-3-one. The mother liquor is concentrated and the recrystallization procedure above repeated in order to give a second crop of crystals. (0.3945 g, 1.363 mmole).

Example 1D

17β-vinyloxy-4-aza-androst-5(6)-en-3-one

The 17β-alcohol prepared in Example 1C (2.20 g, 7.77 mmol) is prepared into a slurry with chloroform (CHCl₃, 30 mL) and ethyl vinyl ether (CH₂CHOC₂H₅, 40 mL). Mercuric acetate (ALDRICH, Hg(OOCCH₃)₂, 2.4869 g, 7.804 mmol) is added to the reaction vessel which is then purged with nitrogen and heating to reflux under a nitrogen atmosphere.

After 14 ½ hours of refluxing, when the reaction is dark brown and homogeneous, the reaction is quenched with acetic acid (HOAC₃, 0.20 mL, 0.21 g, 3.49 mmol) and stirred at room temperature for an additional 2 ½ hours. The reaction mixture is poured into 5% sodium hydroxide (50 mL) and hexane (150 mL), the layers are separated and the organic phase is washed with brine (2×50 mL), dried over potassium carbonate (K₂CO₃), filtered and evaporated to give 17β-vinyloxy-4-aza-androst-5(6)-en-3-one (5.033 g). The compound has the following structure:

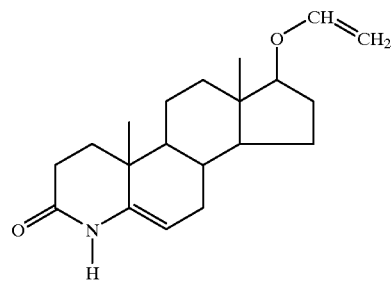

Example 1E

17β-cyclopropyloxy-4-aza-androst-5(6)-en-3-one

In a manner analogous to the procedure described in Charette et al., Tet. Let., 1994, 35(4), 513–16, the vinyl ether (7.77 mmol) is dissolved in chloroform (CHCl₃) under nitrogen. Tert-butyl methyl ether (CH₃OC(CH₃)₃, 20 mL) is added inducing the formation of an off-white precipitate. The solution is chilled to 0° C. under nitrogen. Diethyl zinc ((CH₃CH₂)₂Zn), ALDRICH, 24.0 mL, 26.4 mmol, 1.1 M in toluene) is added to the vinyl ether slurry partially dissolving the precipitate. The slurry is stirred at 0° C. for 10 minutes and methylene iodide (CH₂I₂, ALRICH, 2.20 mL, 7.32 g, 27.3 mmol) is added in small portions over 15 minutes and the slurry is stirred continuously at 0° C. under nitrogen. Another portion of chloroform (CHCl₃, 40 mL) is added, and stirring is continued at 0° for a total reaction time of 6 hours. The reaction mix is poured into 120 mL of a saturated solution of NH₄Cl and extracted with EtOAc (200 mL). The organic phase is extracted with brine (2×100 mL), dried over MgSO₄, filtered and evaporated to give the crude product, which when purified by flash chromatagraphy over silicon dioxide (SiO₂, R_F 0.29) and ethyl acetate/methylene chloride/hexane eluent (25% EtOAc/25% CH₂Cl₂/50% hexane) gave 17β-cyclopropyloxy-4-aza-androst-5(6)-en-3-one. (1.3002 mmol, 17% yield).

¹H NMR (300 MHz, CDCl₃) δ 8.78(br s, 1H), 4.93(dd, J=4.9, 2.0 Hz, 1H), 3.45(t, J=8.4 Hz, 1H), 3.26–3.35(m, 1H), 2.42–2.51(m, 2H), 1.85–2.21(m, 4H), 1.37–1.69(m, 7H), 1.10(s, partially obscured, 3H), 0.94–1.36(m, 4H), 0.79(s, 3H), 0.40–0.60(m, 4H); ¹³C NMR (75 Mz, CDCl₃) δ 169.9, 139.9, 103.3, 88.9, 52.3, 51.2, 48.0, 42.5, 37.1, 34.0, 31.5, 31.4, 29.2, 28.3, 27.8, 23.2, 20.5, 18.6, 11.6, 6.1, 5.8; IR (KBr) 3435 (br), 2967 (m), 1669 (s) cm⁻¹; MS (electron impact m/e calc'd for C₂₁H₃₂NO₂: (330.243305), found (330.242958); 329 (parent), 314, 288, 272 (base), 244, 230, 176, 162, 138, 135, 108.

The compound has the following structure:

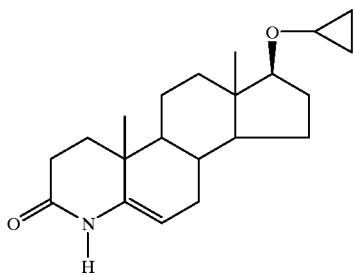

Example 2

17β-cyclopropyloxy-4-aza-5α-androstan-3-one

Example 2A

17β-acetoxy-4-aza-5α-androstan-3-one

17β-Acetoxy-4-aza-5α-androst-5(6)-en-3-one (10.0404 g, 30.2914 mmol) and palladium/carbon catalyst (ENGELHARD, 1.2642 g, 5% Pd on carbon) are placed into a 500 mL Parr bottle. The reaction container is purged with nitrogen and ethanol (250 mL) is added. The reaction container is then charged with hydrogen to 60 p.s.i. and heated to 60° C. with mechanical agitation. At the increased temperature, the pressure of the reaction vessel increases, but then upon reaction with the steroid it decreases. The hydrogen pressure is maintained at around 60 p.s.i. by periodic additions of gas through a ballast tank until the hydrogen pressure becomes constant (about 90–100 hours). Upon completion of the reaction, the reaction mixture is cooled to room temperature, washed through Celite® with acetic acid (70 mL), concentrated and filtered to dryness to give the crude product. The crude product is recrystallized from ethanol (150 mL) by dissolving in boiling solvent (400 mL) and concentrating. The colorless crystals are collected and dried overnight under reduced pressure (0.4 mm Hg) at room temperature and analyzed for purity to give 17β-acetoxy-4-aza-5α-androstan-3-one. Yield 25.08 mmol, 83%. The compound has the following structure:

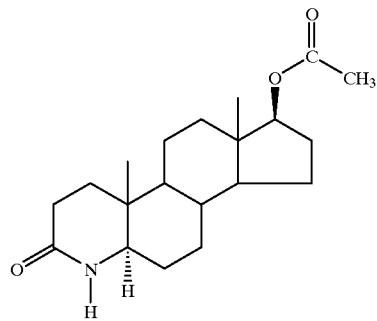

Example 2B

17β-hydroxy-4-aza-5α-androstan-3-one

17β-Acetoxy-4-aza-5α-androstan-3-one (2.6533 g, 7.9559 mmol) prepared in Example 2A is dissolved in warm ethanol (100 mL). Concentrated sodium hydroxide (6M, 50 mL) is added and the reaction is stirred at room temperature. After 90 minutes, the reaction is worked-up by first diluting the reaction mixture with brine (200 mL) and extracting with EtOAc (3×100 mL). The combined organic layers are washed with brine (100 mL), dried over $MgSO_4$, filtered and evaporated to give 17β-hydroxy-4-aza-5α-ndrostan-3-one.

Example 2C

17β-vinyloxy-4-aza-5α-androstan-3-one

In a manner analogous to that reported in Ireland et al., Org. Synth., Coll. Vol. VI, 1988, 298–301, 4-aza-17β-vinyloxy-androstan-3-one (0.5297 g, 1.817 mmol) is made into a slurry with $CH_2Cl_2$ (15 mL) and ethyl vinyl ether ($CH_3CH_2OCHCH_2$, ALDRICH, 11.31 g, 156.8 mmol). Mercuric acetate ($Hg(OOCCH_3)_2$, ALDRICH, 0.6030 g, 1.8922 mmol) is added and the slurry is heated to reflux under nitrogen for 39 hours. Glacial acetic acid ($HOOCCH_3$, EM, 0.050 mL, 0.053 g, 0.873 mmol) is added and the reaction mixture is cooled to room temperature while stirring overnight. The reaction is worked-up by pouring it into 5% aqueous sodium hydroxide (15 mL) and hexane (40 mL). The layers are separated and the organic phases washed with brine (2×24 mL). The combined organic phases are washed, filtered and evaporated to give 17β-vinyloxy-4-aza-5α-androstan-3-one (1.0581 g) which was immediately used in the following step without further characterization.

Example 2D

17β-cyclopropyloxy-4-aza-5α-androstan-3-one

4-Aza-17β-vinyloxy-5α-androstan-3-one (1.817 mmol) prepared in Example 2C is dissolved into a cosolvent system of $CH_2Cl_2$ (12 mL) and methyl tert-butyl ether (12 mL) and chilled to 0° C. under nitrogen. Diethyl zinc ($(CH_3CH_2)_2Zn$) is added, followed by methylene iodide ($CH_2I_2$, ALDRICH, 1.80 mL, 5.96 g, 22.3 mmol) which is added in small portions over 2 minutes. The mixture is stirred at 0° C. under nitrogen for 6 ¼ hours. The reaction is quenched with saturated aqueous $NH_4Cl$ (20 mL) and extracted with EtOAc (100 mL). The combined organic phases are washed with brine (2×50 mL), dried over $MgSO_4$, filtered and the solvents are evaporated to give a crude product of the title compound. The crude product is purified by flash chromatography ($SiO_2$, 50% EtOAc/50% $CH_2Cl_2$) and the product containing fraction collected to give pure 17β-cyclopropyloxy-4-aza-5α-androstan-3-one (0.4223 g, 1.2739 mmole, Yield: 70%). m.p. 237.5–238.5° C. (from acetone). $R_F$ 0.16 (50:50 $CH_2Cl_2$:EtOAc);

$^1$H NMR (300 MHz, $CDCl_3$) δ 6.70(br s, 1H), 3.43(t, J=8.4 Hz, 1H), 3.24–3.33(m, 1H), 3.04(dd, J=12.1, 3.6 Hz, 1H), 2.35–2.43 (m, 2H), 1.92–2.05(m, 1H), 1.82–1.90(m, 2H), 1.71(dd, J=12.9, 2.9 Hz, 1H), 1.10–1.59(m, 11H), 0.90(s, 3H), 0.85–1.03(m, partially obscured, 2H), 0.76 (s, 3H), 0.41–0.59(m, 4H); $^{13}$C NMR (75 MHz, DMSO-d$^6$) δ 170.1, 88.3, 59.7, 51.9, 50.7, 50.0, 42.3, 37.0, 35.0, 34.4, 32.9, 28.7, 28.4, 27.5, 26.2, 22.8, 20.3, 11.7, 11.1, 5.8, 5.6; IR (KBr) 3434 (br), 3194 (m), 1672(s) cm$^{-1}$; MS (electron impact m/e calc'd for $C_{21}H_{34}NO_2$: 332.258955, found 332.257883; 331 (parent), 315, 288, 274 (base), 191, 163, 124, 112.

The product has the following formula:

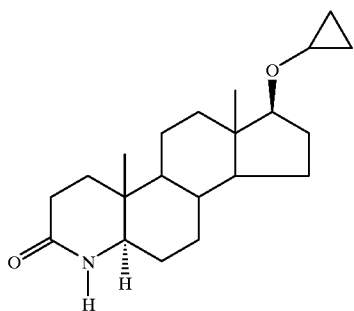

Example 3

17β-cyclopropyloxy-4-methyl-4-aza-androst-5(6)-en-3-one

Example 3A

17β-acetoxy-4-methyl-4-aza-androst-5(6)-en-3-one

17β-hydroxy-5-oxo-4-nor-3, 5-seco-androst-3-carboxylic acid (3.1856 g, 10.329) prepared in Example 1A or otherwise obtained is made into a slurry with methylamine hydrochloride ($CH_3NH_2 \cdot HCl$, ALDRICH, 7.4847 g, 110.9 mmol) and HOAC (80 mL) and heated to reflux under nitrogen. After six days, the reaction is cooled to room temperature and the reaction is concentrated (30 mm Hg, 55° C.) to give a thick slurry. The slurry is taken-up in EtOAc (100 mL), and the organics are washed with water (2×50 mL), with aqueous $NaHCO_3$, (50 mL), and with brine (50 mL). The product is dried over $MgSO_4$, filtered and the solvent evaporated to give the crude product, which is then purified by flash chromatography ($SiO_2$, 25% EtOAc/25% $CH_2Cl_2$/25% hexane) to give 17β-acetoxy-4-methyl-4-aza-androst-5(6)-en-3-one (3.3373 g, 9.763 mmol). Yield: 95%. The compound has the following structure:

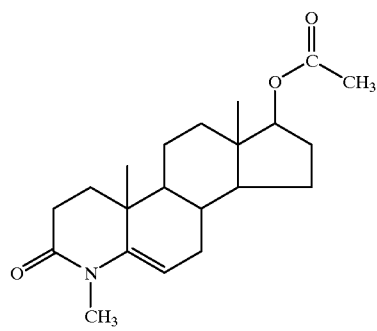

Example 3B

17β-hydroxy-4-methyl-4-aza-androst-5(6)-en-3-one

17β-Acetoxy-4-methyl-4-aza-androst-5(6)-en-3-one (3.373 g, 9.763 mmol) is dissolved in ethanol (50 mL). Concentrated sodium hydroxide (6M, 25.0 mL) is added and the reaction is stirred at room temperature for 4 ½ hours. The reaction is partitioned between brine (10.0 mL) and EtOAc (100 mL). The layers are separated and the organic layer washed with brine (2×100 mL), saturated $NH_4Cl$ (100 mL), dried over $MgSO_4$, filtered and evaporated to give a crude reaction product as a yellow solid. This is purified by dissolving in methanol and evaporating until the formation of large crystals is seen. The crystals are washed in acetone and dried overnight at reduced pressure (0.3 mm Hg) to give 17β-hydroxy-4-methyl-4-aza-androst-5(6)-en-3-one of very good purity (1.8119 g, 5.9712 mmol). Yield: 61%. m.p. 188° C.–192° C.

Example 3C 4-methyl-17β-vinyloxy-4-aza-androst-5(6)-en-3-one

17β-Hydroxy-4-methyl-4-aza-androst-5(6)-en-3-one (0.9278 g, 3.0576 mmol) is dissolved in $CH_2Cl_2$ to which is added ethyl vinyl ether ($CH_3CH_2CHCH_2$, ALDRICH, 20.0 mL, 15.08 g, 209.1 mmol) while stirring. Mercuric acetate ($Hg(OOCCH_3)_2$) is added and the reaction is heated to reflux under nitrogen. After 24 ½ hours, the reaction is cooled to room temperature, and HOAc (EM, 1.00 mL, 1.06 g, 17.46 mmol) is added. After 15 ½ hours, the reaction mixture is poured into a mixture of hexane (100 mL) and 10% sodium hydroxide. The container is well mixed then the phases are separated and the organics washed with brine (2×50 mL), dried over $MgSO_4$, filtered and the solvent evaporated to give 4-methyl-17β-vinyloxy-4-aza-5α-androst-5(6)-en-3-one 1.3829 g), which corresponds to the structure:

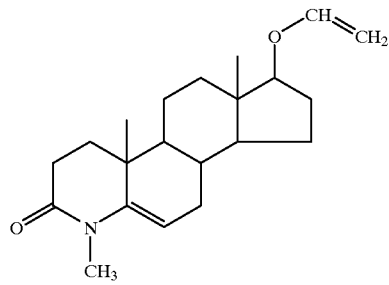

Example 3D

17β-cyclopropyloxy-4-methyl-4-aza-5α-androst-5(6)-en-3-one

The vinyl ether prepared in Example 3C (4-methyl-17β-vinyloxy-4-aza-5α-androst-5(6)-en-3-one, 3.05 mmol) is dissolved into a mixture of $CH_2Cl_2$ (20 mL) and t-butyl methyl ether (20 mL) and chilled to 0° C. under nitrogen. Diethyl zinc (($CH_3CH_2)_2Zn$, ALDRICH, 20.0 mL, 1.1 M in toluene, 22.0 mmol) is added followed by charging with, in small portions, methylene iodide ($CH_2I_2$, ALDRICH, 1.80 mL, 5.96 g, 22.3 mmol). After 6 ½ hours, the reaction is worked-up by first quenching with saturated $NH_4CO$ (50 mL) and extracting with EtOAc (100 mL). The organic phases are washed with brine (2×50 mL), dried over $MgSO_4$, filtered, and the solvent evaporated to give the crude reaction product. The crude product is purified by flash chromatography ($SiO_2$, 25% EtOAc/25% $CH_2Cl_2$/50% hexane) to give 4-methyl-17β-cyclopropyloxy-4-aza-5α-androst-5(6)-en-3-one (0.4095 g, 1.1921 mmol) which when analyzed further indicates the presence of some minor impurities.

$R_F$ 0.48 (50:25:25-hexane:$CH_2Cl_2$:EtOAc) $^1$H NMR (300 MHz, $CDCl_3$) δ 5.04 (br d, J=3.6 Hz, 1H), 3.46(t, J=8.4 Hz, 1H), 3.27–3.35(m, 1H), 3.12(s, 3H), 2.53(br AB q, J=3.6 Hz, 2H), 2.24(dt, J=16.8, 5.0 Hz, 1H), 1.87–2.09(m, 3H), 1.40–1.73(m, 6H), 1.06(s, 3H), 0.98–1.34(m, partially obscured, 5H), 0.79(s, 3H), 0.42–0.61(m, 4H); $^{13}$C NMR (75 MHz, CDCl$_3$) δ 168.1, 144.0, 104.1, 88.7, 52.2, 51.0, 48.8, 42.3, 37.1, 35.2, 31.5, 30.9, 30.6, 30.1, 28.7, 27.7, 23.1, 20.4, 18.6, 11.5, 6.0, 5.7; IR (KBr) 3437 (br), 1676 (s), 1647 (s) cm$^{-1}$; MS (electron impact) m/e 343 (parent), 328, 302, 286(base), 270, 244, 190, 176, 152, 135, 124.

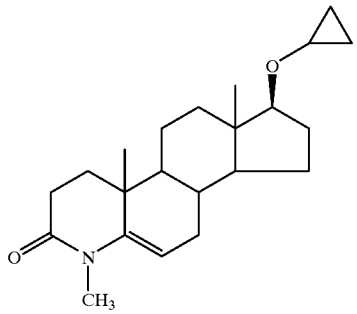

Example 4

17β-cyclopropyloxy-4-aza-5α-androst-1-en-3-one

Example 4A

17β-acetoxy-4-aza-5α-androst-1-en-3-one

In a manner analogous to the procedure described in Bhattacharya, A. et al., *J. Am. Chem. Soc.*, 1988, 110, 3318–3319, 17β-acetoxy-4-aza-5α-androstan-3-one (0.7687 g, 2.3049 mmol) and 2,3-dichloro-5,6-dicyano-1,4-benzoquinone (DDQ, ALDRICH, 0.5461 g, 2.4056 mmol) are dissolved into 1,4-dioxane (15.0 mL) under nitrogen. Bis(trimethylsilyl)-trifluoroacetamide (BSTFA, ALDRICH, 2.60 mL, 2.52 g, 9.79 mmol) is added and the reaction mixture is stirred at room temperature for 60 minutes. The reaction is heated to reflux for 18 hours, cooled to room temperature and the solvent is allowed to evaporate. The residue is dissolved in EtOAc (50 mL), washed with 5% sodium hydroxide (50 mL), and with brine (50 mL), dried over MgSO$_4$, filtered and the solvent evaporated to give the crude reaction product. The crude product is purified by flash chromatography (SiO$_2$, 50% EtOAc/50% CH$_2$Cl$_2$) to give 17β-acetoxy-4-aza-5α-androst-1-en-3-one (0.6102 g, 1.8409 mmol) of very good purity. Yield: 80%. The compound has the following formula:

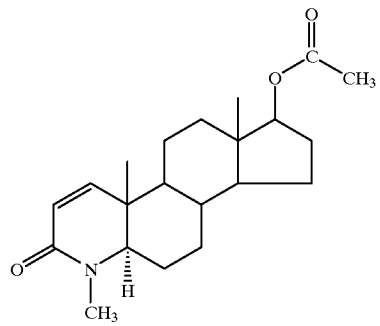

Example 4B

17β-hydroxy-4-aza-5α-androst-1-en-3-one

17β-Acetoxy-4-aza-5α-androst-1-en-3-one (0.500 g, 1.508 mmol) is dissolved in warm ethanol (20 mL). 6M sodium hydroxide (10 mL) is added and the reaction is stirred for 16 hours at room temperature. The reaction is diluted with EtOAc (50 mL) extracted with brine (3×100 mL), and dried over MgSO$_4$ to give 17β-hydroxy-4-aza-5α-androst-1-en-3-one (0.4570 g) and a minor impurity. The reaction product is carried onto the next synthesis without further purification.

Example 4C

17β-vinyloxy-4-aza-5α-androst-1-en-3-one

In a manner analogous to Examples 1D, 2C, 3C and as described in Ireland, R. E. et al., *Org. Synth., Coll. Vol. VI*, 1988, 298–301, 17β-hydroxy-4-aza-5α-androst-1-en-3-one (1.508 mmol), ethyl vinyl ether (CH$_3$CH$_2$OCHCH$_2$, ALDRICH, 9.80 g, 135.9 mmol) and mercuric acetate (Hg(OAc)$_2$, ALDRICH, 0.5101 g, 1.6007 mmol) are reacted in CH$_2$Cl$_2$, (15 mL) for 66 hours. The reaction is quenched with acetic acid (EM, 0.346 g, 5.76 mmol) and stirred for 1 hour. The reaction is diluted with 10% sodium hydroxide (25 mL), extracted with brine (2×25 mL) filtered and dried to give 17β-vinyloxy-4-aza-5α-androst-1-en-3-one (0.6906) in quantitative yield which is carried onto the next step without further purification.

Example 4D

17β-cyclopropyloxy-4-aza-5α-androst-1-en-3-one

In a manner analogous to Examples 1E, 2D and 3D, 17β-vinyloxy-4-aza-5α-androst-1-en-3-one (1.508 mmol), tert-butyl methyl ether (10 mL), diethyl zinc (ALDRICH, 1.1M in toluene, 10.00 mL, 11.00 mmol) and methylene iodide (CH$_2$I$_2$, ALRICH 0.900 mL, 2.99 g, 11.17 mmol) are reacted together wherein the CH$_2$I$_2$ additions occurs in small portions over 5 minutes. After 2 ½ hours, the reaction is brought to room temperature, and worked-up after 14 hours by quenching with saturated NH$_4$Cl (50 mL), extracting with EtOAc (75 mL) and washing with brine (70 mL). This product is purified with a 50% EtOAc/50% CH$_2$Cl$_2$ eluent to give in good purity 17β-cyclopropyloxy-4-aza-5α-androst-1-en-3-one (0.2246 g, 0.6816 mmol). Yield: 45%. R$_F$ 0.41 (50:50-CH$_2$Cl$_2$:EtOAc). $^1$H NMR (300 MHz, CDCl$_3$) δ 6.79(d, J=10.0 Hz, 1H), 6.62(br s, 1H), 5.80(dd, J=9.9, 2.2 Hz, 1H), 3.45(t, J=8.4 Hz, 1H), 3.25–3.34(m, 2H), 1.92–2.05 (m, 2H), 1.31–1.77(m, 8H), 1.13–1.30(m, 3H), 0.97(s, 3H), 0.90–1.07(m, partially obscured, 2H), 0.77(s, 3H), 0.41–0.59(m, 4H). $^{13}$C NMR (75 Mhz, CDCl$_3$) δ 166.8, 150.9, 122.8, 88.7, 59.5, 52.3, 50.5, 47.6, 42.8, 39.2, 37.2, 35.0, 28.9, 27.8, 25.6, 23.1, 20.8, 11.9, 11.8, 6.0, 5.8. IR (KBr) 3425 (br), 3200 (m), 1682 (s) cm$^{-1}$; MS (electron impact) m/e calc'd for C$_{21}$H$_{32}$NO$_2$: 330.243305, found 330.243780; 329 (parent), 314, 286, 272 (base), 256, 228, 190, 163, 148, 122, 110.

The compound has the following structure:

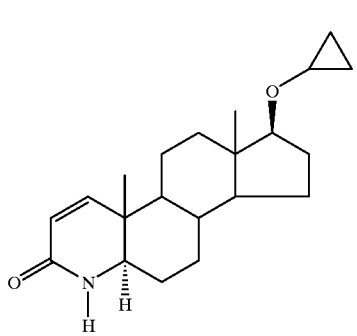

Example 5

17β-cyclopropylamino-4-aza-androst-5(6)-ene-3-one

Example 5A 5,17-oxo-4-nor-3,5-seco-androstane-3-carboxylic acid

Testosterone (8.7813 g, 30.45 mmol) is dissolved into a mixture of $CH_2Cl_2$ (50 mL) and methanol (10 mL) and the solution is chilled to −78° C. under nitrogen while stirring. Ozone is bubbled through the reaction while maintaining temperature and stirring for 3 hours. Note that after 30 minutes the reaction color turns blue. The reaction is slowly brought to room temperature, while replacing the ozone with nitrogen. The solvent is evaporated and the residue is taken-up in ether (200 mL) and extracted with 10% sodium hydroxide (3×50 mL), noting gas evolution. The combined alkaline phases are combined and washed again with ether (50 mL). The solution is acidified with 10% sulfuric acid ($H_2SO_4$, 200 mL) and extracted with $CH_2Cl_2$ (5×50 mL). The organic phases are combined and extracted with brine (50 mL), dried over $MgSO_4$, filtered and the solvent is evaporated to give crystals of 5,17-oxo-4-nor-3,5-seco-androstane-3-carboxylic acid (8.14 g).

Example 5B 4-aza-androst-5(6)-ene-3,17-dione

The seco acid prepared in Example 5A (8.14 g, 26.56 mmol) is dissolved into (HOAc (100 mL). Ammonium acetate ($NH_4OOCCH_3$, 15.6931 g, 203.6 mmol) is added and the reaction mix is heated to reflux under nitrogen. After 69 hours, the reaction is cooled to room temperature and is poured into ice water (700 mL), whereupon the product separates as a tarry mass. The solution is diluted with brine (200 mL) and extracted with EtOAc (3×200 mL). The organic phases are combined and washed with brine (2×200 mL), with water (3×200 mL) and with saturated $NaHCO_3$ (2×100 mL). The extract is dried over $MgSO_4$, filtered and the solvent evaporated to give the crude product of the title compound. The product is recrystallized from ethanol to give 4-aza-androst-5(6)-ene-3,17-dione with traces of the $C_{17}$-acetate (1.0859 g, 3.778 mmol). A second recrystallization of the mother liquor gives additional compound (0.5431 g). Total Yield: 21%. The desired product has the following structure:

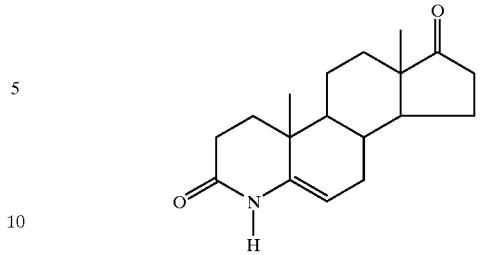

Example 5C

17β-cyclopropylamino-4-aza-androst-5(6)-en-3-one

4-Aza-androst-5(6)-ene-3,17-dione (0.53 g, 1.844 mmol) dissolved in chloroform ($CHCl_3$, 10.0 mL) and cyclopropylamine (($CH_2$)$_2$$CHNH_2$, ALDRICH, 4.12 g, 72.15 mmol) is added, and the reaction mixture is heated to reflux under nitrogen. After 15 hours, the reaction is cooled to room temperature and analysis indicates the stoichiometric conversion to the cyclopropylimine. Sodium borohydride ($NaBH_4$, ALPHA, 0.3574 g, 0.4475 mmol) in ethanol (21 mL) is added and the reaction is stirred at room temperature under nitrogen. After 21 hours, the reaction is worked-up by diluting with EtOAc (50 mL), washing in water (2×40 mL), in brine (40 mL) and drying over $MgSO_4$, filtering and evaporating the solvent to obtain the crude product of the title compound. The crude product is further purified by flash chromatography (10.5", 5.25 g, $SiO_2$; elute first with 25% EtOAc/×25% $CH_2Cl_2$/50% hexane then with 15% $^iPrOH$/×85%×$CH_2Cl_2$) to give 17β-cyclopropylamino-4-aza-androst-5(6)-en-3-one in excellent purity (0.4948 g, 1.5063 mmol). Yield: 82%.

$R_F$ 0.42 (15:85-$^i$PrOH:$CH_2Cl_2$); $^1$H NMR (300 MHz, $CDCl_3$) δ 9.22 (br s, 1H), 4.93–4.97 (m, 1H), 2.67 (t, J=8.5 Hz, 1H), 2.42–2.51 (m, 2H), 1.86–2.22 (m, 5H), 1.40–1.70 (m, 7H), 1.04–1.40 (m partially obscured, 5H), 0.73 (s, 3H), 0.28–0.44 (m, 7H), 1.09 (s, 3H), 1.04–1.40 (m partially obscured, 5H), 0.73 (s, 3H), 0.28–0.44 (m, 4H). $^{13}$C NMR (75 MHz, DMSO-d$^6$) δ 167.7, 140.7, 101.0, 68.7, 52.8, 47.8, 42.1, 37.2, 33.5, 31.2, 31.1, 29.6, 29.0, 28.9, 28.2, 23.3, 20.2, 18.4, 11.6, 6.9, 6.3. IR (KBr) 3429 (br), 3202 (m), 1669 (s) cm$^{-1}$. MS (electron impact) m/e 328 (parent), 313, 299 (base), 271, 256, 243, 228, 204, 162, 137, 108.

The compound has the following structure:

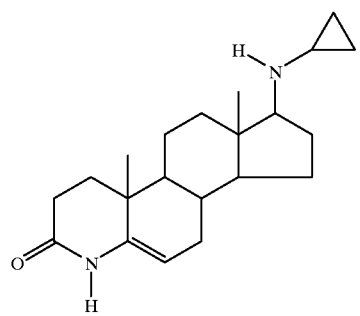

Example 6

17β-cyclopropylamino-4-aza-5α-androstan-3-one

Example 6A 5,17-dioxo-4-nor-3,5-seco-androstane-3-carboxylic acid

Androst-4-ene-3,17-dione (10.000 g, 34.914 mmol) is dissolved in a mixture of $CH_2Cl_2$ (100 mL) and EtOAc (100 mL), and the solution is chilled to −78° C. under nitrogen. Ozone is bubbled below the surface of the solution through a coarse glass frit until the reaction mixture turns deep blue. The −78° C. reaction mixture is then sparged with dry nitrogen until the blue color dissipates. The solution is allowed to warm to ambient temperature and the solvent removed under reduced pressure. The residue is taken up in ether (250 mL) and the product extracted with 10% sodium hydroxide (3×25 mL). The combined basic extracts are washed with fresh ether (100 mL), then acidified with 10% sulfuric acid ($H_2SO_4$; 100 mL). The acidic aqueous solution is then extracted with $CH_2Cl_2$ (4×50 mL). The combined $CH_2Cl_2$ extracts are washed once with brine (50 mL), dried over $MgSO_4$, filtered and the solvent is evaporated under reduced pressure to give the title compound.

Example 6B

4-Aza-androst-5(6)-ene-3,17-dione 5,17-Oxo-4-nor-3,5-seco-androstane-3-carboxylic acid prepared in Example 6A (9.000 g, 29.373 mmol) and ammonium acetate ($NH_4OAc$; 22.58 g, 292.9 mmol) are slurried in HOAc (75 mL) heated to reflux under an inert atmosphere. After 3 days, the reaction mixture is allowed to cool to room temperature and then is poured into ice cold water (700 mL). The resulting precipitate is collected by filtration, air dried, and recrystallized from ethanol to afford the title compound.

Example 6C

17β-hydroxy-4-aza-5α-androstan-3-one

4-Aza-androst-5(6)-ene-3,17-dione (7.000 g, 24.356 mmol) (see Example 6B) and 5% palladium on carbon catalyst (0.750 g, 0.352 mmol Pd) are placed into a 500 mL Parr bottle under an inert atmosphere. Acetic acid (100 mL) is added to the reaction vessel which is then charged with hydrogen to 60 p.s.i. The hydrogenation reaction is heated to 60° C. and agitated with a Parr shaker. After three days, the reaction mixture is allowed to cool to ambient temperature and filtered through Celite®. The filtrate is concentrated to approximately 25 mL under reduced pressure, then poured into ice cold water (300 mL). The precipitate is then collected by filtration and recrystallized from ethanol to give the title compound.

Example 6D 4-aza-5α-androstan-3,17-dione

17β-Hydroxy-4-aza-5α-androst-3-one (6.000 g, 20.590 mmol) prepared in Example 6C or otherwise obtained is dissolved in $CH_2Cl_2$ (200 mL) and prepared for oxidation by addition of powdered 4 Å molecular seives (ALDRICH 23,366-8, 12.00 g). 4-Methylmorpholine N-oxide (5.000 g, 42.680 mmol) and tetrapropylammonium perruthenate (VII) (0.400 g, 1.138 mmol) are then sequentially added. The reaction is stirred under an inert atmosphere at ambient temperature. After about 3 days, the reaction solution is filtered through silica gel (1:1 $EtOAc/CH_2Cl_2$), and carefully purified by flash chromatography (1:1 $EtOAc/CH_2Cl_2$) to give 4-aza-5α-androst-3,17-dione.

Example 6E

17β-cyclopropylamino-4-aza-5α-androstan-3-one

4-Aza-5α-androstan-3,17-dione (3.000 g, 10.366 mmol) from Example 6D is dissolved in chloroform ($CHCl_3$) (50 mL), cyclopropylamine (25.00 mL, 360.8 mmol) is added and the reaction is heated to reflux with stirring under a nitrogen atmosphere. After 20 hours, the reaction mixture is allowed to cool to room temperature and a solution of sodium borohydride ($NaBH_4$; 4.000 g, 105.7 mmol) in ethanol (100 mL) is added. The reaction mixture is stirred an additional five hours, then diluted with EtOAc (200 mL). The diluted solution is washed with water (2×200 mL) and brine (150 mL). The organic solution is dried over $MgSO_4$, filtered and concentrated under reduced pressure. The residue is purified by flash chromatography (elute first with 1:1:2 $EtOAc/CH_2Cl_2$/hexane, then with 15:85 $^i$PrOH/$CH_2Cl_2$) to give the title compound in excellent purity.

Example 7

1-fluoro-17β-cyclopropyloxy-4-methyl-4-aza-5α-androstan-3-one

Example 7A

17β-acetoxy-4-methyl-4-aza-5α-androstan-3-one

17β-Acetoxy-4-methyl-4-aza-androst-5(6)-en-3-one (20.000 g, 57.890 mmol) prepared in Example 3A or otherwise obtained and 5% palladium on carbon catalyst (2.000 g, 0.940 mmol) are placed into a 500 mL Parr bottle under an inert atmosphere. Acetic acid (150 mL) is added to the reaction vessel, which is then charged to 60 p.s.i. with hydrogen gas. The hydrogenation reaction takes place at 60° C., with shaking. After 3 days, the reaction mixture is filtered through Celite®, filtered and concentrated to approximately 50 mL under reduced pressure. The concentrated product solution is poured into ice cold water (800 mL) with stirring. The resulting precipitate is collected by filtration and recrystallized from ethanol to give the title compound.

Example 7B

17β-acetoxy-4-methyl-4-aza-5α-androst-1(2)-en-3-one

17β-Acetoxy-4-methyl-4-aza-5α-androstan-3-one (18.000 g, 52.098 mmol) prepared in Example 7A or otherwise obtained and 2,3-dichloro-5,6-dicyano-1,4-benzoquinone are dissolved in 1,4-dioxane (200 mL). Bis (trimethylsilyl)trifluoroacetamide (136.0 mL, 512.0 mmol) is carefully added to the dioxane solution while maintaining an inert atmosphere. After stirring for 60 minutes at room temperature, the reaction mixture is heated to reflux. The reflux is continued for eighteen hours, at which time the reaction is allowed to cool to ambient temperature. The reaction solvent is removed under reduced pressure and the residue is redissolved in EtOAc (500 mL). The organic solution is washed with 5% sodium hydroxide (400 mL) and brine (400 mL), then dried over $MgSO_4$, filtered and concentrated under reduced pressure. The reaction product is further purified by flash chromatography (1:1 $EtOAc/CH_2Cl_2$) to give the title compound.

Example 7C

17β-hydroxy-4-methyl-4-aza-5α-androst-1(2)-en-3-one

17β-Acetoxy-4-methyl-4-aza-5α-androst-1(2)-en-3-one prepared in Example 7B (15.000 g, 43.673 mmol) is dissolved in a mixture of ethanol (100 mL) and THF (100 mL). To the ethanolic solution is added 6M sodium hydroxide (100 mL), then the reaction mixture is stirred at room temperature for seven hours. At the end of this time, the reaction mixture is diluted with EtOAc (600 mL) and extracted with brine (3×400 mL). The organic layer is dried over MgSO$_4$, filtered, and evaporated to dryness to afford a crude product of sufficient purity for subsequent syntheses.

Example 7D

17β-cyclopropyloxy-4-methyl-4-aza-5α-androst-1 (2)-en-3-one

17β-Hydroxy-4-aza-4-methyl-androst-1-en-3-one (12.000 g, 39.552 mmol) from Example 7C is dissolved into a mixture of CH$_2$CH$_2$ (200 mL) and ethyl vinyl ether (200 mL, 2.091 mol). Mercury (II) acetate (Hg(OAc)$_2$; 13.500 g, 42.362 mmol) is added to the reaction mixture, which is then heated to reflux under an inert atmosphere. After three days, the reaction solution is cooled to room temperature and acetic acid (8.00 mL, 139.7 mmol) is added. The acidified reaction mixture is stirred at room temperature for 2 hours, then diluted with hexane (500 mL). The organic solution is extracted with 10% sodium hydroxide (300 mL) and brine (2×200 mL), dried over MgSO$_4$, filtered, and evaporated to dryness to obtain 17β-vinyloxy-4-methyl-4-aza-androst-1-en-3-one which is used without further purification in the following synthesis.

17β-vinyloxy-4-methyl-4-aza-androst-1-en-3-one (8.000 g, 24.279 mmol) prepared in the previous paragraph is dissolved into a mixture of CH$_2$Cl$_2$ (100 mL) and methyl t-butyl ether (100 mL), and then chilled to 0° C. under a nitrogen atmosphere. Diethylzinc solution (1.1 M in toluene; 145 mL, 159.5 mmol) is added to the steroid solution with stirring, followed by cautious, dropwise addition of CH$_2$I$_2$ (13.00 mL, 161.4 mmol). The 0° C. reaction mixture was stirred for 2.5 hours, then allowed to warm to room temperature over 14 hours. The reaction is then quenched with saturated aqueous NH$_4$Cl (300 mL) and extracted with EtOAc (500 mL). The organic extract is washed with brine (2×300 mL), dried over MgSO$_4$, filtered, and evaporated to dryness. The crude product is purified by flash chromatography (1:1 EtOAc/CH$_2$Cl$_2$ to give the title compound.

Example 7E

17β-cyclopropyloxy-4-methyl-1-phenylthio-4-aza-5α-androstan-3-one

Sodium hydride (50% dispersion in mineral oil, 0.580 g, 12.08 mmol) is washed with hexane (3×25 mL) under an inert atmosphere to remove the mineral oil. Anhydrous tetahydrofuran (THF, 50 mL) is cautiously added while maintaining the inert atmosphere. A solution of thiophenol (1.230 mL, 11.98 mmol) in THF (50 mL) is slowly added dropwise over 30 minutes, while stirring, as gas is given off. At the end of the addition, the THF solution is heated to reflux for 30 minutes and then allowed to cool to room temperature. To the stirring thiophenoxide slurry is added a solution of 17β-cyclopropyloxy-4-methyl-4-aza-5α-androstan-1-en-3-one (4.000 g, 11.645 mmol) in THF (50 mL) in small portions over 20 minutes. Under an inert atmosphere, the reaction mixture is stirred for 40 minutes at ambient temperature after the addition, then it is heated to reflux. After refluxing 2 hours, the reaction is cooled to room temperature and carefully poured into ice water (500 mL). The reaction mixture is then extracted with EtOAc (3×500 mL), the combined organic phases with brine (2×250 mL), dried over MgSO$_4$, filtered and evaporated to dryness.

Purification by flash chromatography (1:1:2 EtOAc/CH$_2$Cl$_2$/hexane) gives the title compound. The compound has has the following structure:

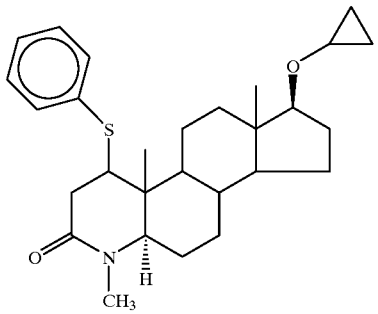

Example 7F

2-Bromo-17β-cyclopropyloxy-1-fluoro-4-methyl-4-aza-5α-androst-1-en-3-one

In a manner similar to that disclosed in Bohlman, R. *Tet. Lett.* 1994, 35(1), 85–88, a solution of 17β-cyclopropyloxy-4-methyl-1-phenylthio-4-aza-5α-androstan-3-one (3.000 g, 6.613 mmol) in CH$_2$Cl$_2$ (100 mL) at 0° C. is prepared. N-bromosuccinimide 2.360 g, 13.259 mmol) and diethylaminosulfur trifluoride (0.880 mL, 6.661 mmol) under an inert atmosphere are sequentially added and the reaction mixture is stirred at 0° C. for 4.5 hours, then poured into saturated aqueous NaHCO$_3$ (50 mL) and extracted with CH$_2$CH$_2$ (3×50 mL). The combined organic extracts are washed with brine (100 mL), dried over MgSO$_4$), filtered and evaporated to dryness. The product is purified by flash chromatography (1:1 EtOAc/CH$_2$Cl$_2$) to give 2-bromo-17β-cyclopropyloxy-1-fluoro-4-methyl-4-aza-5α-androst-1-en-3-one.

Example 7G

17β-Cyclopropyloxy-1-fluoro-4-methyl-4-aza-5α-androst-1-en-3-one

In a manner similar to that disclosed in Bohlman, R. *Tet. Lett.* 1994, 35(1), 85–88, 2-bromo-17β-cyclopropyloxy-1-fluoro-4-methyl-4-aza-5α-androst-1-en-3-one (1.000 g, 2.270 mmol) is slurried in toluene (40 mL). Under nitrogen, tributyltin hydride (0.680 mL, 2.528 mmol) and azobisisobutyronitrile (0.0750 g, 0.457 mmol) are added to the toluene slurry, and the reaction is heated to 80° C. while stirring. After 3 hours, the reaction is cooled to room temperature and passed through silica gel (1:1 EtOAc/CH$_2$Cl$_2$). The eluant is concentrated and purified by flash chromatography (1:1 EtOAc/CH$_2$Cl$_2$) to give the title compound.

Example 7H

17β-cyclopropyloxy-1-fluoro-4-methyl-4-aza-5α-androstan-3-one

In a manner similar to that disclosed in Kitazume T., et al., *J. Org. Chem.* 1989, 54(23), 5630–5632, 17β-cyclopropyloxy-1-fluoro-4-methyl-4-aza-5α-androst-1-en-3-one (0.250 g, 0.692 mmol) and 10% Pd/C catalyst (0.0250 g, 0.0235 mmol Pd) are placed into a flask which is subsequently flushed with nitrogen. Ethanol (10 mL) is added and the vessel is charged with hydrogen (1 atmosphere). After 30 hours of ultrasonic radiation (32 KHz, 35 W), the reaction mixture is filtered through Celite®, and evaporated to dryness. The residue is purified by flash chromatography (1:1 EtOAc/CH$_2$Cl$_2$) to give the title compound:

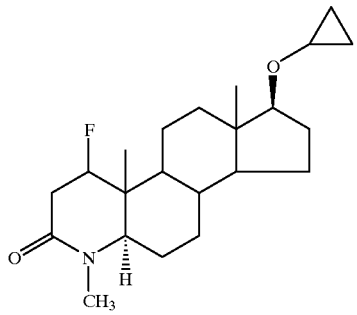

Example 8

1-phenylsulfinyl/phenylsulfonyl-17β-cyclopropyloxy-4-methyl-4-aza-5α-androstan-3-one

Example 8A

17β-cyclopropyloxy-1-phenylsulfinyl-4-methyl-4-aza-5α-androstan-3-one

17β-Cyclopropyloxy-4-methyl-1-phenylthio-4-aza-5α-androstan-3-one (3.000 g, 6.613 mmol), prepared as in Example 7E or otherwise obtained, is dissolved in CH$_2$Cl$_2$ (100 mL) and chilled to −78° C. under an inert atmosphere of nitrogen. 3-Chloroperoxy-benzoic acid (55% in water and 3-chlorobenzoic acid; 2.250 g, 7.171 mmol) is added and the reaction is stirred for 3 hours at −78° C. while maintaining the nitrogen atmosphere, after which the reaction is quenched with saturated aqueous Na$_2$SO$_3$ (100 mL). The organic phase is separated and washed 1 M NaOH (3×25 mL) and with brine (50 mL), dried over MgSO$_4$, filtered, and evaporated to dryness. Purification of the residue by flash chromatography (1:1 EtOAc/CH$_2$Cl$_2$) gives the title compound.

Example 8B

17β-cyclopropyloxy-1-phenylsulfonyl-4-methyl-4-aza-5α-androstan-3-one

Under nitrogen, 17β-cyclopropyloxy-1-phenylsulfinyl-4-methyl-4-aza-5α-androstan-3-one (2.000 g, 4.260 mmol) is dissolved in CH$_2$Cl$_2$ (70 mL). 3-Chloroperoxy-benzoic acid (55% in water and 3-chlorobenzoic acid; 1.500 g, 4.781 mmol) is added to the solution. After stirring 16 hours under nitrogen, the reaction is quenched with saturated aqueous Na$_2$SO$_3$ (70 mL). The organic phases are separated and washed with 1 M NaOH (3×25 mL) and brine (50 mL), dries over MgSO$_4$, filtered, and evaporated to dryness. Purification of the residue by flash chromatography gives the title compound, which has the following formula:

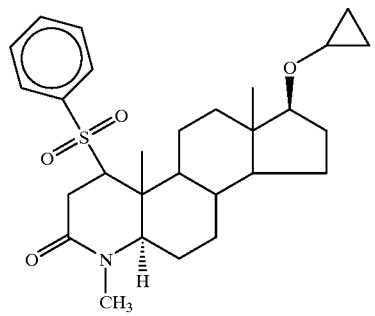

Example 9

1-fluoro-cyclopropylamino-4-methyl-4-aza-5α-androstan-3-one

Example 9A

17β-cyclopropylamino-4-methyl-4-aza-5α-androst-1(2)-en-3-one

17β-Hydroxy-4-methyl-4-aza-5α-androst-1(2)-en-3-one (from Example 7C or otherwise obtained) is C$_{17}$ oxidized as in Example 6D (17-one). The C$_{17}$ is then cyclomaminated into the title compound in a manner similar as described in Example 6E.

EXAMPLES 9B, 9C, 9D, 9E

17β-cyclopropylamino-4-methyl-1-phenylthio-4-aza-5α-androstan-3-one 2-bromo-17β-cyclopropylamino-1-fluoro-4-methyl-4-aza-5α-androst-1(2)-en-3-one 17β-cyclopropylamino-1-fluoro-4-methyl-4-aza-5α-androst-1(2)-en-3-one 17β-cyclopropylamino-1-fluoro-4-methyl-4-aza-5α-androstan-3-one 17β-Cyclopropylamino-4-methyl-4-aza-5α-androst-1(2)-en-3-one is reacted in a manner similar to that described in Examples 7E–H, respectively, to obtain the corresponding title compounds.

Example 10

1-phenylthio/phenylsulfinyl/phenylsulfonyl-4-methyl-cyclopropylamino-4-methyl-4-aza-5α-androstan-3-one

Example 10A, 10B

17β-cyclopropylamino-4-methyl-1-phenylsulfinyl-4-aza-5α-androstan-3-one

17β-cyclopropylamino-4-methyl-1-phenylsulfonyl-4-aza-5α-androstan-3-one

17β-Cyclopropylamino-4-methyl-1-phenylthio-4-aza-5α-androstan-3-one from Example 9B or otherwise obtained is reacted in a manner similar to the procedures described in Examples 8A and 8B, respectively, to obtain the corresponding title compounds.

Example 11

2-halo/methylthio/methylsulfinyl/methylsulfonyl-17β-cyclopropyloxy-4-aza-5α-androst-3-one

Example 11A

17β-trimethylsilyloxy-4-aza-5α-androstan-3-one

17β-Hydroxy-4-aza-5α-androstan-3-one prepared in Example 2B or otherwise obtained (20.000 g, 68.634 mmol)

in CH$_2$Cl$_2$ (500 mL) is added to trimethylsilyl chloride (TMSCL) (18.00 mL, 141.83 mmol) with stirring, under nitrogen. Triethylamine (20.00 mL, 143.49 mmol) is added in small portions over 30 minutes. After stirring vigorously for 48 hours under nitrogen, the reaction mixture is filtered through Celite®. The filtrate is evaporated to dryness and re-dissolved in ether (500 mL). The ether solution is filtered through Celite® and concentrated under reduced pressure to give the title compound.

Example 11B

17β-hydroxy-2α-bromo-4-aza-5α-androstan-3-one

17β-Trimethylsilyloxy-4-aza-5α-androstan-3-one from Example 11A (10.000 g, 27.517 mmol) is prepared in solution with toluene (100 mL). N,N,N',N'-tetramethylethylene-diamine ((CH$_3$)$_2$NCH$_2$CH$_2$N(CH$_3$)$_2$, TMEDA, 12.50 mL, 82.824 mmol) is added under nitrogen. The solution is chilled to −37° C. and tetramethylsilyl iodide (TMSI, 3.95 mL, 27.76 mmol) is added dropwise. The resulting slurry is stirred for 5 minutes and then bromine (7.00 mL, 135.87 mmol) is added dropwise. The stirring reaction mixture is allowed to warm to 20° C., after which it is poured into saturated aqueous sodium sulfite (Na$_2$SO$_3$, 100 mL). The biphasic mixture is extracted with EtOAc (100 mL), and the organic phases are combined and washed twice with Na$_2$SO$_3$ (100 mL) and then with brine (2×100 mL). The material is then dried over MgSO$_4$, filtered and evaporated to dryness. The residue is redissolved in THF (100 mL), and a tetrabutylammonium fluoride solution (1M in THF; 28.00 mL, 28.00 mmol) is added to the THF solution, and the mixture is then stirred at room temperature for 15 minutes. After this time period, the reaction mixture is poured into saturated aqueous NH$_4$Cl (100 mL) and extracted with EtOAc (3×200 mL). The organic extractions are combined, washed twice with brine (150 mL), dried over MgSO$_4$, filtered and concentrated under reduced pressure. The crude product is purified by flash chromatography (1:1 EtOAc/CH$_2$Cl$_2$) to give the title compound in sufficient purity for the next synthesis.

Example 11C

17β-cyclopropyloxy-3α-bromo-4-aza-5α-androstan-3-one

17β-Hydroxy-2α-bromo-4-aza-5α-androstan-3-one is etherified and cyclopropanated into the title compound in a manner similar to that reported in Examples 7D.

Example 11D

17β-hydroxy-2-iodo-4-aza-5α-androstan-3-one

17β-Trimethylsilyloxy-4-aza-5α-androstan-3-one (10.000 g, 27.517 mmol) prepared in Example 11A or otherwise obtained is dissolved into toluene (100 mL) and N,N,N',N'-tetramethylethylenediamine (TMEDA) (12.50 mL, 82.824 mmol) is added under nitrogen. The solution is chilled to −37° C. and tetramethylsilylchloride (7.35 mL, 57.91 mmol) is added rapidly dropwise. The resulting slurry is stirred for 5 minutes and then iodine (10.00 g, 39.40 mmol) is added in one continuous portion. The mixture is allowed to warm to 20° C. at which time it is poured into saturated aqueous sodium sulfite (Na$_2$SO$_3$, 100 mL). The resulting biphasic mixture is extracted with EtOAc (100 mL), the organic phases are combined and washed with saturated aqueous sodium sulfite (Na$_2$SO$_3$, 100 mL) and brine (100 mL), dried over MgSO$_4$, filtered, and evaporated to dryness. The residue is redissolved in THF (100 mL), tetrabutylammonium fluoride (1M in THF; 28.00 mL, 28.00 mmol) is added, and the mixture is stirred at room temperature for 15 minutes. At the end of this time period, the reaction is poured into saturated aqueous NH$_4$Cl (100 mL) and extracted with EtOAc (3×200 mL). The combined organic extracts are washed with brine (2×150 mL), dried over MgSO$_4$, filtered and concentrated under reduced pressure. The crude product is purified by flash chromatography to give the title compound of purity sufficient for subsequent syntheses (1:1 EtOAc/CH$_2$Cl$_2$).

Example 11E

17β-cyclopropyloxy-2α-iodo-4-aza-5α-androstan-3-one

17β-Hydroxy-2-iodo-4-aza-5α-androstan-3-one is treated in a manner similar to the procedures described in Example 7D give the title compound.

Example 11F

17β-cyclopropyloxy-2α-methylthio-4-aza-5α-androstan-3-one

17β-Cyclopropyloxy-2α-iodo-4-aza-5α-androstan-3-one (2.500 g, 5.470 mmol) from Example 11E or otherwise obtained is slurried in ethanol (50 mL), and the mixture is heated to reflux under an inert atmosphere. After 20 hours, the reaction solution is allowed to cool to room temperature and is poured into saturated aqueous NH$_4$Cl (200 mL). The solution is extracted with EtOAc (200 mL), the organic extracts combined, washed with brine (2×150 mL), dried over MgSO$_4$, filtered and evaporated to dryness. The residue is purified by flash chromatography (1:1 EtOAc/CH$_2$Cl$_2$) to give the title compound of purity sufficient for subsequent syntheses. The compound has the following structure:

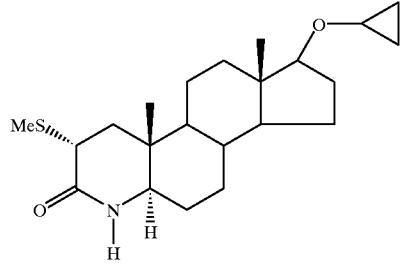

EXAMPLES 11G–11H

17β-cyclopropyloxy-2α-methylsulfinyl-4-aza-5α-androstan-3-one

17β-cyclopropyloxy-2α-methylsulfonyl-4-aza-5α-androstan-3-one

17β-Cyclopropyloxy-2α-methylthio-4-aza-5α-androstan-3-one is reacted in a manner similar to that described in Examples 8A and 8B, respectively, to obtain the corresponding title compounds.

Example 12

2α-halo/methylthio/methylsulfinyl/methylsulfonyl-17β-cyclopropylamino-4-aza-5α-androstan-3-one Example 12A 17β-cyclopropylamino-2α-iodo-4-aza-5α-androstan-3-one 17β-Hydroxy-2α-iodo-4-aza-5α-androstan-3-one prepared in Example 11D or otherwise obtained is oxidized in a manner similar to the procedure described in Example 6D to give to give 2α-iodo-4-aza-5α-androstan-3,17-dione (the dione). The dione is then converted to the 17-cyclopropylimine and subsequently to the title compound in a similar manner as described in Example 6E.

Example 12B

17β-cyclopropylamino-2α-methylthio-4-aza-5α-androstan-3-one

17β-cyclopropylamino-2α-methylsulfinyl-4-aza-5α-androstan-3-one

17β-cyclopropylamino-2α-methylsulfonyl-4-aza-5α-androstan-3-one

The above title compounds are created from 17β-cyclopropylamino-2α-iodo-4-aza-5α-androstan-3-one prepared in Example 12A or otherwise obtained is converted into the corresponding title compounds in a manner similar to that described in Example 11F, 11G and 11H, respectively, to obtain the corresponding title compound.

Example 12C

17β-cyclopropylamino-2α-bromo-4-aza-5α-androstan-3-one

17β-Cyclopropylamino-2α-bromo-4-aza-5α-androstan-3-one prepared in Example 11B or otherwise obtained is oxidized in a manner similar to that described in Example 6D to give 2α-bromo-4-aza-5α-androstan-3,17-dione (the dione). The dione is then converted to the 17-cyclopropylimine and subsequently to the title compound in a similar manner as described in Example 5E.

Example 13

4-methy-4-aza-5α-androstan-3-one

Example 13A

17β-hydroxy-4-methyl-4-aza-5α-androstan-3-one

17β-Hydroxy-4-methyl-4-aza-androst-5(6)-ene-3-one prepared in Example 3B or otherwise obtained is hydrogenated under conditions similar to those described in Example 6C to give the title compound.

Example 13B

17β-cyclopropyloxy-4-methyl-4-aza-5α-androstan-3-one

4-Methyl-17β-hydroxy-4-aza-5α-androstan-3-one prepared in Example 13A or otherwise obtained is etherified and cyclopropanated as described in Example 7D to give the title compound.

Example 13C

17β-cyclopropylamino-4-methyl-4-aza-5α-androstan-3-one

17β-Hydroxy-4-methyl-4-aza-5α-androstan-3-one prepared in Example 13A or otherwise obtained is oxidized into 4-methyl-4-aza-5α-androst-3,17-dione (the dione) as described in Example 6D. The dione is then cycloaminated as described in Example 6E to give the title compound.

Example 14

2α-halo/methylthio/methylsulfinyl/methylsulfonyl-4-methyl-17β-cyclopropyloxy-4-aza-5α-androstan-3-one

Example 14A 4-methyl-17β-trimethylsilyloxy-4-aza-5α-androstan-3-one

17β-Hydroxy-4-methyl-4-aza-5α-androstan-3-one prepared in Example 13A or otherwise obtained is silylated as described in Example 11A to give the title compound, to afford the title compound.

Example 14B

2α-bromo-17β-cyclopropyloxy-4-methyl-4-aza-5α-androstan-3-one

4-Methyl-17β-trimethylsilyloxy-4-aza-5α-androstan-3-one from Example 14A or otherwise obtained is brominated and cyclopropanated in a manner similar to the procedure described in Examples 11B and 11C, respectively, to obtain the title compound.

Example 14C

2α-iodo-17β-cyclopropyloxy-4-methyl-4-aza-5α-androstan-3-one

4-Methyl-17β-trimethylsilyloxy-4-aza-5α-androstan-3-one from Example 14A or otherwise obtained is iodated and cyclopropanated in a manner similar as in Examples 11D and 11E, respectively, to give the title compound.

Examples 14D, 14E AND 14F

17β-cyclopropyloxy-4-methyl-2α-methylthio-4-aza-5α-androstan-3-one

17β-cyclopropyloxy-4-methyl-2α-methylsulfinyl-4-aza-5α-androstan-3-one

17β-cyclopropyloxy-4-methyl-2α-methylsulfonyl-4-aza-5α-androstan-3-one

2α-Iodo-17β-cyclopropyloxy-4-methyl-4-aza-5α-androstan-3-one from Example 14C or otherwise obtained is reacted as described in Examples 11F, 11G and 11H, respectively, to obtain the above corresponding title compounds.

Example 15

2α-halo/methylthio/methylsulfinyl/methylsulfonyl-4-methyl-17β-cyclopropylamino-4-aza-5α-androstan-3-one

Example 15A

2α-iodo-17β-cyclopropylamino-4-methyl-4-aza-5α-androstan-3-one

2α-Iodo-17β-hydroxy-4-methyl-4-aza-5α-androstan-3-one is oxidized and cycloaminated as in Examples 6D-6E, respectively, to give the title compound.

Examples 15B, 15C AND 15D

17β-cyclopropylamino-4-methyl-2α-methylthio-4-aza-5α-androstan-3-one

17β-cyclopropylamino-4-methyl-2α-methylsulfinyl-4-aza-5α-androstan-3-one

17β-cyclopropylamino-4-methyl-2α-methylsulfonyl-4-aza-5α-androstan-3-one

2α-Iodo-17β-cyclopropylamino-4-methyl-4-aza-5α-androstan-3-one is reacted in a manner similar to the procedures described in Examples 11F, 11G and 11H, respectively, to give the above corresponding title compounds.

Example 15E

2α-bromo-17β-cyclopropylamino-4-methyl-4-aza-5α-androstant-3-one

2α-Bromo-17β-trimethylsilyloxy-4-methyl-4-aza-5α-androstant-3-one prepared in Example 14A is hydrolyzed as in Example 11B to give 2α-bromo-17β-hydroxy-4-methyl-4-aza-5α-androstan-3-one (17-alcohol). The 17-alcohol is then oxidized and cycloaminated as in Examples 6D–6E, respectively, to give the title compound.

Example 16

7β-ethyl-17β-cyclopropyloxy-4-aza-androst-5(6)-en-3-one

Example 16A

3β-hydroxy-17β-tributyldimethylsilyloxy-androst-5(6)-ene 3β-acetate

3β17β-Dihydroxy-androst-5(6)-en-3-acetate (50.000 g, 150.38 mmol) obtained by treating 3β-acetoxy-androst-5(6)-ene-17-one (available from ALDRICH, 39,008–9) with sodium borohydride, is dissolved in $CH_2Cl_2$ (225 mL) with t-butyldimethylsilyl chloride (30.000 g, 199.0 mmol) under nitrogen. Diazabicyclo[5.4.0]undec-7-ene (DBU, 33.00 mL, 220.7 mmol) is added dropwise to the $CH_2CH_2$ solution, while keeping the temperature below reflux with an ice bath. After stirring for 72 hours at room temperature, the reaction solution is diluted with EtOAc, (800 mL) and extracted with saturated aqueous $NH_4Cl$ (3×200 mL), brine (200 mL), saturated aqueous $NaHCO_3$ (200 mL) and once again with brine (200 mL). The combined organic phases are dried over $MgSO_4$, filtered and concentrated under reduced pressure to give the title compound of purity sufficient for subsequent synthesis.

Example 16B

3β-acetoxy-17β-tert-butyldimethylsilyloxy-androst-5(6)-en-7-one

In a manner similar to the procedure described in Pinto et al., Chem. Pharm. Bull., 1988 36(12) 4689–4692, and Kutney T., Gletus, C., Steroids 1966, 7(1), 67–78, 3β-Hydroxy-17β-tert-butyldimethylsilyloxy-androst-5(6)-ene 3-acetate (60.000 g, 134.3 mmol) is dissolved in carbon tetrachloride ($CCl_4$), 250 mL). Acetic anhydride (38.00 mL, 402.7 mmol), acetic acid (100.0 mL, 1746.8 mmol), and t-butylchromate are sequentially added to the $CCl_4$ solution, which is then heated to reflux temperature under an inert atmosphere. After 29 hours, the reaction is cooled to 0° C. and poured into a stirring solution of oxalic acid (70.000 g, 777.4 mmol) in water (700 mL). An additional portion of oxalic acid (54.000 g, 599.7 mmol) is added to the biphasic mixture and stirring was continued for 4 hours while the solution is allowed to warm to room temperature. Water (750 mL) is added and the biphasic mixture is extracted three times with $CH_2Cl_2$ (800 mL). The combined organic phases are washed with water (2×1000 mL), dried over $MgSO_4$, filtered and evaporated to dryness. The crude product is recrystallized from ethanol to give the title compound in sufficient purity for subsequent synthesis.

Example 16C

17β-t-butyldimethylsilyloxy-7-ethyl-androst-5-en-3β-7-ol

3β-Acetoxy-17β-t-butyldimethylsilyloxy-androst-5(6)-en-7-one (40.000 g, 86.821 mmol) is dissolved in THF (500 mL) under an inert atmosphere. A solution of ethylmagnesium chloride (2.0 M in THF; 90.0 mL, 180.0 mmol) is added in portions over 60 minutes to the steroid solution. At the end of the addition, the reaction mixture is stirred six hours at room temperature and then heated to reflux. After 16 hours at reflux, the Grignard reaction mixture is allowed to cool to room temperature and then poured into saturated aqueous $NH_4Cl$ (500 mL). The reaction product is extracted into EtOAc (3×500 mL) and the combined extracts are washed with saturated aqueous $NaHCO_3$ (3×500 mL) brine (500 mL) dried over $MgSO_4$, filtered and concentrated to afford the crude product as a mixture of diastereomers which is carried onto the next step without further purification.

Example 16D 7-ethyl-17β-tert-butyldimethylsilyloxy-androst-4, 6-dien-3-one

In a manner similar to the procedure described in Eastham, J. & Teranishi, R., Org. Synth. Cell Vol. IV, 1963, 192–195 and Dierassi C., Org. React., 1951, 6, 207–272 17β-t-butyldimethylsilyloxy-7-ethyl-androst-5-en-3β,7-ol (35.000 g, 71.324 mmol) prepared in Example 16C, is dissolved in a mixture of toluene (700 mL) and cyclohexanone (200 mL). To the toluene solution is added dropwise a solution of aluminum isopropoxide (10.000 g, 48.960 mmol) in toluene (150 mL). The reaction mixture is heated to reflux under an inert atmosphere. After about thirty minutes, or when the reaction volume is condensed to about one-half the original volume, saturated aqueous potassium sodium tartrate tetrahydrate [$KNa(CHO—)_2(CH_2H)_2$-$4H_2O$, 150 mL] is added, and the reaction is brought to reflux for 30 minutes with vigorous stirring. At the end of this time, the biphasic solution is allowed to cool to room temperature and the layers separated. The aqueous phase is extracted three times with $CH_2Cl_2$ and the combined organic phases are washed with brine (2×100 mL), dried with $MgSO_4$, filtered and concentrated under reduced pressure. The residue is recrystallized from ethanol to give the title compound.

Example 16E

7β-ethyl-17β-tert-butyl-dimethylsilyloxy-androst-5-en-3-one

In a manner similar to the procedures described in Crabtree, S. et al., Org. Synth. 1991, 70, 256–264; Caine, D. et al. Org. Synth. Cell. Vol. Vi__1988, 51–55 and Caine D., Org. React__1976, 23, 1–258, to dry liquid ammonia (3.00 mL) at −78° C. under an inert atmosphere is added small pieces of lithium metal (0.950 g, 136.9 mmol). After stirring 20 minutes at −78° C. or until the lithium is dissolved, a solution of 7-ethyl-17β-tert-butyldimethylsilyloxy-androst-4,6-dien-3-one from Example 16D or otherwise obtained in a mixture of t-butanol (5.70 mL, 60.45 mmol) and toluene (50 mL), is added dropwise to the blue ammonia solution over 60 minutes while maintaining the temperature at −78° C. After the addition, the ammonia solution is stirred an additional 15 minutes after which is applied a quench of solid $NH_4Cl$, 15.00 g, 280.4 mmol). The ammonia is allowed to evaporate from the reaction mixture under a stream of dry nitrogen while the reaction vessel is allowed to warm to room temperature. The remaining toluene slurry is diluted with EtOAc (300 mL), washed with water (200 mL), washed again with brine (2×200 mL), dried over $MgSO_4$, filtered and evaporated to dryness. The residue is recrystalized from ethanol to give the title compound.

Example 16F

7β-ethyl-17β-hydroxy-androst-4-en-3-one

7β-Ethyl-17β-tert-butyl-dimethylsilyloxy-androst-5-en-3-one (15.000 g, 34.824 mmol) from Example 16E or otherwise obtained is dissolved in THF (100 mL). To the solution is added 1,8-diazabicyclo[5.4.0]undec-7-ene (1.20 mL, 8.024 mmol) and the reaction mixture is heated to reflux under nitrogen. After 1 hour, the reaction mixture is cooled to room temperature and tetrabutylammonium fluoride (1.0 M in THF; 36.0 mL, 36.00 mmol) is added. The desilylation reaction is allowed to occur over 90 minutes at room temperature with stirring. At the end of this time, the reaction mixture is diluted with EtOAc (500 mL) and washed with saturated aqueous NH$_4$Cl (3×200 mL) and brine (200 mL), then dried over MgSO$_4$, filtered, and evaporated to dryness. The residue is recrystalized from ethanol to give the title compound.

Example 16G

7β-ethyl-17β-hydroxy-4-aza-androst-5-en-3-one

7β-Ethyl-17β-hydroxy-androst-4-en-3-one (10.000 g, 34.914 mmol) is converted into 17β-hydroxy-7β-ethyl-5-oxo-4-nor-3,5-seco-androstane-3-carboxylic acid (seco acid) as in Example 6A. The seco acid is then converted into the β-lactam similar to the procedure reported in Example 6B. The β-lactam is then hydrolyzed to 17β-hydroxy-androst-4-en-3-one in a manner similar as reported in Example 7C.

Example 16H

17β-cyclopropyloxy-7β-ethyl-4-aza-5α-androst-5-en-3-one

17β-Hydroxy-4-aza-androst-5-en-3-one prepared in Example 16G, above is etherified and cyclopropanated as described in Examples 7D to give the title compound.

Example 17

17β-cyclopropyl(oxy/amino)-7β-ethyl-4-aza-5α-androst-[1(2)-en/an]-3-one

Example 17A

17β-acetoxy-7β-ethyl-4-aza-5α-androstan-3-one

17β-Acetoxy-7β-ethyl-4-aza-androst-5-en-3-one prepared in Example 16G, second paragraph is hydrogenated in a manner similar as in Example 6C to give the title compound.

Example 17B

17β-cyclopropyloxy-7β-ethyl-4-aza-androstan-3-one

17β-Acetoxy-7β-ethyl-4-aza-5α-androstan-3-one from Example 17A is hydrolyzed as reported in Example 7C, then etherified and cyclopropanated as described in Example 7D to give the title compound.

Example 17C

17β-hydroxy-7β-ethyl-4-aza-5α-androst-1(2)-en-3-one

17β-Acetoxy-7β-ethyl-5α-androstan-3-one from Example 17A is dehydrogenated as in Example 7B to give 17β-acetoxy-7β-ethyl-4-aza-5α-androst-1(2)-en-3-one, which is then hydrolyzed as in Example 7C to give the title compound.

Example 17D

17β-cyclopropyloxy-7β-ethyl-4-aza-5α-androst-1(2)-en-3-one

17β-Hydroxy-7β-ethyl-4-aza-5α-androst-1(2)-en-3-one from Example 17C is etherified and cyclopropanated as described in Example 7D to give the title compound.

Example 17E

17β-cyclopropylamino-7β-ethyl-4-aza-5α-androstan-3-one

17β-Hydroxy-7β-ethyl-4-aza-5α-androst-1(2)-en-3-one from Example 17C is C$_{17}$-oxidized as described in Example 6D, then cycloaminated as described in Example 6E to give the title compound.

Example 17F

17β-cyclopropylamino-7α-ethyl-4-aza-5α-androstan-3-one

17β-Acetoxy-7β-ethyl-5α-androstan-3-one from Example 17A is hydrolyzed as in Example 7B, then C$_{17}$-oxidized as in Example 6D, then cycloaminated as in Example 6E to give the title compound.

Example 18

17β-Cyclopropyloxy-4-aza-androst-3,7-dione

Example 18A

7,7-ethylenedioxy-17β-t-butyldimethylsilylyoxy-androst-5-en-3-ol 3-acetate

In a manner similar to that described in Tsunoda T., et al., *Tet. Lett.*, 1980, 21(14), 1357–1358, Hwa et al., *J. Org. Chem.*, 1987, 52(2), 188–191. A solution of 3β-acetoxy-17β-t-butyldimethylsilyloxy-androst-5-en-7-one (40.000 g, 86.821 mmol) from Example 16B or otherwise obtained and 1,2-bis(trimethylsiloxy)ethane (23.00 mL, 93.81 mmole) in CH$_2$Cl$_2$ (300 mL) is prepared at −78° C. Trimethylsilyl trifluoromethanesulfonate (0.20 mL, 1.035 mmol) is added under an inert atmosphere, the reaction is stirred for three hours, pyridine (2.00 mL, 24.73 mmol) is added and the stirred mixture is allowed to warm to room temperature. The organic solution is poured into saturated aqueous NaHCO$_3$ (300 mL) and the resultant biphasic solution is extracted with EtOAc (3×300 mL). The combined organic extracts are washed with brine (200 mL), dried over MgSO$_4$, filtered and evaporated to dryness. The residue is purified by flash chromatography (1:4 EtOAc/hexane) to give 7,7-ethylenedioxy-17β-t-butyldimethylsilylyoxy-androst-5-en-3-ol 3-acetate.

Example 18B

17β-hydroxy-4-aza-androst-5-ene-3,7-dione 7,7-Ethylenedioxy-17β-t-butyldimethylsilylyoxy-androst-5-en-3-ol 3-acetate from from Example 18A is hydrolyzed in a manner similar as described in Example 7C to 7,7-ethylenedioxy-17β-t-butyldimethylsilylyoxy-androst-5-en-3-ol, which is oxidized into 7,7-ethylenedioxy-17β-t-butyldimethyl-silylyoxy-androst-5-en-3-one by the procedure described in Example 7D which is then isomerized and desilylated in the manner described in Example 16F to obtain 7,7-ethylenedioxy-17β-hydroxy-androst-4-en-3-one.

7,7-Ethylenedioxy-17β-hydroxy-androst-4-en-3-one is oxidized into 7,7-ethylenedioxy-17β-hydroxy-5-oxo-4-nor-3,5-seco-androstane 3-carboxylic acid (seco-acid) as described in Example 6A. The seco-acid is converted into 17β-hydroxy-4-aza-androst-5-ene-3,17-dione (β-lactam) in a manner similar to that described in Example 6B. The β-lactam is hydrolyzed under conditions similar to those described under Example 7C to give 17β-Hydroxy-4-aza-androst-5-ene-3,7-dione.

Example 18C

17β-cyclopropyloxy-4-aza-androst-5-en-3,17-dione

17β-Hydroxy-4-aza-androst-5-en-3,17-dione from Example 18A or otherwise obtained is cyclopropanated in a manner similar to that described in Example 7D to give the title compound.

Example 18D

17β-cyclopropyloxy-4-aza-5α-androstan-3,17-dione

17β-Cyclopropyloxy-4-aza-androst-5-en-3,17-dione from Example 18C or otherwise obtained is hydrogenated under similar conditions as reported in Example 7H to give the title compound.

Example 19

17β-Cyclopropylamino-4-aza-androst-5-diene-3,7-dione

Example 19A

17β-trimethylsilyloxy-4-trimethylsilyl-4-aza-androst-5-ene-3,7-dione

17β-Hydroxy-4-aza-androst-5-ene-3,7-dione (40.000 g, 131.84 mmol) prepared in Example 18A or otherwise obtained is prepared in solution at −78° C. in dry THF (300 mL). Lithium diisopropylamide solution (2.0 M in heptane/THF/ethylbenzene; 135.0 mL, 270.0 mmol) is added under an inert atmosphere and the deprotonation reaction occurs while stirring at −78° C. over 60 minutes. Trimethylsilyl chloride (35.00 mL, 275.8 mmol) is added, and stirring is continued for an additional 15 minutes and then the solution is allowed to warm to room temperature. After stirring an additional 2 hours, the reaction mixture is filtered through Celite® and the filtrate is evaporated to dryness. The residue is redissolved in ether (500 mL) and the resultant slurry is filtered again through Celite®. The solvent is evaporated to give the title compound.

Example 19B 7-t-butyldimethylsilyloxy-17β-cyclopropylamino-4-aza-androst-5,7-dien-3-one By the procedure described in Hart, J. W. et al., *J. Chem. Soc. Chem. Commun.* 1979, 156–157 17β-trimethylsilyloxy-4-trimethylsilyl-4-aza-androst-5-ene-3,7-dione prepared in Example 19A (40.000 g, 92.644 mmol) is prepared in a −78° C. solution in a mixture of THF, (300 mL) and hexamethylphosphoramide (30.0 mL, 172.4 mmol) and is reacted with lithium diisopropylamide (2.0 M in heptane/THF/ethylbenzene; 50.0 mL, 100.0 mmol) under an inert atmosphere. Deprotonation is allowed to occur over 60 minutes with stirring at −78° C. t-Butyldimethylsilyl chloride (17.00 g, 112.8 mmol) in THF (50 mL) solution is added to the steroid solution via cannula, and the reaction is stirred an additional 30 minutes, and then allowed to warm to room temperature. After stirring for 20 hours at ambient temperature, the reaction is quenched by carefully adding saturated aqueous NH$_4$Cl (300 mL). The biphasic mixture is extracted with EtOAc (3×400 mL) and the combined organic layers are washed with water (3×300 mL) and brine (300 mL), dried over MgSO$_4$, filtered and concentrated to give 7-(t-butyldimethylsilyloxy)-4-trimethylsilyloxy-17β-trimethylsilyloxy-4-aza-androst-5,7-dien-3-one (the residue).

The residue is taken up in THF (200 mL) and treated with a mixture of acetic acid (200 mL) and water (25 mL). The reaction is stirred for 60 minutes at ambient temperature, then diluted with EtOAc (800 mL) and washed with brine (2×300 mL), water (4×300 mL), saturated NaHCO$_3$ (2×300 mL) and brine (300 mL). The organic solution is dried over MgSO$_4$, filtered and concentrated. The residue is purified by flash chromatography (1:1:2 EtOAc/CH$_2$Cl$_2$/hexane) to afford 7-(t-butyldimethylsilyloxy)-17β-hydroxy-4-aza-androst-5,7-en-3-one (17-alcohol).

The 17-alcohol is oxidized by application of the conditions described under Example 6D into 7-(t-butyldimethylsilyloxy)-4-aza-androst-5,7-diene-3,17-dione, which is then converted into 17β-cyclopropylamino-7-(t-butyldimethylsilyloxy)-4-aza-androst-5,7-diene-3-one under conditions similar to those described under Example 6E.

Example 19C

17β-cyclopropylamino-4-aza-androst-5-ene-3,7-dione

17β-Cyclopropylamino-7-(t-butyldimethylsilyloxy)-4-aza-androst-5,7-dien-3-one (5.000 g, 10.947 mmol) prepared in Example 19B or otherwise obtained is dissolved into THF (50 mL) under nitrogen, and added to this solution is tetrabutylammonium fluoride (1.0 M in THF; 12.00 mL, 12.00 mmol). The reaction mixture is stirred for 90 minutes at ambient temperature, then quenched with water (200 mL). The crude product solution is extracted with EtOAc (2×200 mL), and the combined organic extracts are washed with brine (3×200 mL). The organic solution is dried over MgSO$_4$, filtered and concentrated. The residue is purified by flash chromatography (1:1 EtOAc/CH$_2$Cl$_2$) to give the title compound.

Example 19D

17β-cyclopropylamino-4-aza-5α-androstan-3,7-dione

17β-Cyclopropylamino-4-aza-androst-5-ene-3,7-dione from Example 19C or otherwise obtained is hydrogenated in a manner similar to that described in Example 7H to afford the title compound.

Example 20

4-aza-7-hydroxy/7-oxo-androstene

Example 20A

17β-cyclopropyloxy-7β-hydroxy-4-aza-androst-5-en-3-one

17β-Cyclopropyloxy-4-aza-androst-5-en-3,7-dione (1.000 g, 2.9115 mmol) prepared in Example 18B or otherwise obtained, dissolved in a mixture of THF (25 mL) and ethanol (25 mL) is added to a solution of sodium borohydride (NaBH$_4$; 1.000 g, 26.43 mmol) in ethanol (50 mL). The reaction mixture is stirred 5 hours at ambient temperature. At the end of this time, the reaction solution is diluted with EtOAc (100 mL) and washed with brine (NaCl; 3×100 mL). The organic solution is dried over MgSO$_4$, filtered, concentrated and purified by flash chromatography (1:1 EtOAc/CH$_2$Cl$_2$) to give the title compound.

Examples 20B, 20C AND 20D

17β-cyclopropyloxy-7β-hydroxy-4-aza-5α-androstan-3-one

17β-cyclopropylamino-7β-hydroxy-4-aza-androst-5-en-3-one

17β-cyclopropylamino-7β-hydroxy-4-aza-5α-androstan-3-one

The above 7-hydroxy steroids are obtained from selectively oxidizing the C$_7$-carbon of the corresponding 7-oxo compounds, 17β-cyclopropyloxy-4-aza-5α-androstan-3,7-dione, 17β-cyclopropylamino-4-aza-androst-5-ene-3,7-dione and 17β-cyclopropylamino-4-aza-5α-androstan-3,7-dione, obtained in Examples 18C, 19C and 19D, respectively, by the procedure described in Example 20A.

Example 21

4-Aza-7β-carboxy-androstane

Example 21A

7β-ethoxycarbonylmethyl-17β-hydroxy-4-aza-5α-androstan-3-one

A solution of sodium hydride (50% in mineral oil; 7.000 g, 145.8 mmol) is prepared in THF, (200 mL), and the solution is washed with hexane (3×30 mL). Triethyl phosphonoacetate (28.7 mL, 144.7 mmol) is cautiously added dropwise under nitrogen, allowing the anion to form for over 60 minutes. A solution of 17β-trimethylsilyloxy-4-trimethylsilyl-androst-5-ene-3,7-dione (32.406 g, 72.374 mmol) in THF is added, followed by stirring at room temperature for 6 hours under nitrogen. After this time, EtOAc (500 mL) is added and the reaction is washed with brine (3×400 mL), dried over MgSO$_4$, filtered and concentrated under reduced pressure to form 17β-trimethylsilyloxy-4-trimethylsilyl-7-ethoxycarbonylmethylene-4-aza-androst-5-en-3-one (diene disilane).

The diene disilane prepared above is redissolved in THF (300 mL) and treated with tetrabutylammonium fluoride (1.0 M in THF; 35.0 mL, 35.0 mmole). The desilylation reaction occurs over 20 minutes with stirring at ambient temperature. The reaction mixture is then diluted with EtOAc (500 mL) and washed with brine (3×400 mL). The crude product solution is dried over MgSO$_4$, filtered and evaporated to dryness. The crude product is purified by flash chromatography (1:1 EtOAc/CH$_2$Cl$_2$) to afford 17β-hydroxy-4-trimethylsilyl-7-ethyloxycarbonylmethylene-4-aza-androst-5-en-3-one as a mixture of the E and Z isomers (diolefin). The diolefin is then hydrogenated in a manner similar to that described in Example 7H to give 7β-ethoxycarbonylmethyl-17β-hydroxy-4-aza-5α-androstan-3-one. The compound has the following structure:

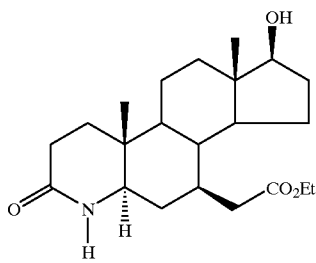

Example 21B

17β-cyclopropyloxy-7-ethoxycarbonylmethyl-4-aza-5α-androstan-3-one

7β-Ethoxycarbonylmethyl-17β-hydroxy-4-aza-5α-androstan-3-one from Example 21A is etherified and cyclopropanated in a manner similar to that described in Example 7D to give the title compound.

Example 21C

17β-cyclopropyloxy-4-aza-3-oxo-5α-androstane 7β-ethanoic acid

In a manner similar to that reported in Example 7C, 17β-cyclopropyloxy-7-ethoxycarbonylmethyl-4-aza-5α-androstan-3-one is selectively hydrolyzed at the C$_7$ position to afford the title compound.

Example 22

17β-cyclopropyloxy-7β-ethoxycarbonyl/carboxy-4-aza-5α-androstan-3-one

Example 22A

17β-hydroxy-7β-(diphenylhydroxymethyl)-4-aza-5α-androstan-3-one

17β-Hydroxy-7β-ethoxycarbonyl-4-aza-5α-androstan-3-one (10.000 g, 26.489 mmol) prepared in Example 21A is dissolved in dry THF (200 mL) and to this solution is cautiously added phenylmagnesium chloride (2.0 M in THF; 55.0 mL, 110.0 mmol) with vigorous stirring under nitrogen while keeping the reaction solution below the reflux temperature by an ice bath. The reaction mixture is stirred for 3 hours at room temperature after addition of the Grignard reagent, then heated to reflux for 16 hours with vigorous stirring under nitrogen. The reaction mixture is allowed to cool to ambient temperature and then is quenched by careful addition of saturated aqueous NH$_4$Cl (300 mL). The crude product slurry is extracted with EtOAc, (3×300 mL). The combined organic extracts are washed with brine (200 mL), dried over MgSO$_4$, filtered and evaporated to dryness. The residue is purified by flash chromatography (15:85 isopropyl alcohol/CH$_2$Cl$_2$) to give the title compound.

Example 22B 3,17-dioxo-4-aza-5α-androstane 7β-carboxylic acid

In a manner analogous to that reported in Riegel, B. et al, Org. Synth., Coll. Vol. 3, 1955, 234–236 and Subramaniam, C. S., et al., Synthesis, 1978, 468–469, 17β-hydroxy-7β-(diphenylhydroxymethyl)-4-aza-5α-androstan-3-one (8.000 g, 16.890 mmol) prepared in Example 22A is dissolved in a mixture of CH$_2$Cl$_2$ (60 mL) and acetic acid (60 mL), then is treated with a solution of chromium trioxide (chromic acid, CrO$_3$; 8.500 g, 85.01 mmol) in a mixture of water (6.0 mL) and acetic acid (40 mL) at room temperature. The reaction mixture is stirred 20 minutes and then acetic anhydride (34.0 mL, 360.3 mmol) is added. The reaction solution is heated to a gentle reflux with stirring. After 20 minutes at reflux, the reaction is quenched by the cautious addition of methanol (50 mL) then cooled to room temperature and concentrated to approximately 75 mL. The concentrated solution is poured into ice water (500 mL), and the resultant precipitate is collected by filtration. The solid is recrystallized from ethanol to afford the title compound.

Example 22C

7β-ethoxycarbonyl-4-aza-5α-androstane-3,17-dione

In a manner analogous to the procedure reported by Neises, B. and Steglich, W., *Org. Synth.* 1984, 63, 183–187, 3,17-dioxo-4-aza-5α-androstane 7β-carboxylic acid (3.000 g, 8.998 mmol) prepared in Example 22C (3.000 g, 8.998 mmol) and 4-(dimethylamino)-pyridine (1.100 g, 9.004 mmol) were dissolved in a mixture of CH$_2$Cl$_2$ (50 mL) and ethanol (50 mL) under nitrogen. 1,3-Dicyclohexylcarbodiimide (2.000 g, 9.693 mmol) is added to the steroid solution and the reaction mixture is stirred at room temperature for 3 hours. The reaction solution is then filtered through Celite® to remove any dicyclohexylurea which might precipitate. The filtrate is evaporated to dryness and purified by flash chromatography (1:1 EtOAc/CH$_2$Cl$_2$) to give the title compound. The compound has the following formula:

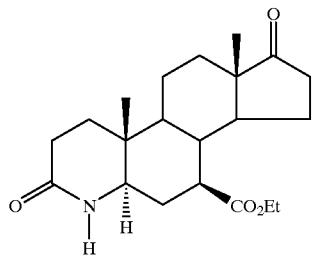

Example 22D

17β-cyclopropyloxy-7β-ethoxycarbonyl-4-aza-5α-androstan-3-one

In a manner analogous to the procedure reported in Example 20A, 7β-ethoxycarbonyl-4-aza-5α-androstane-3,17-dione from Example 22C or otherwise obtained is reduced into 17β-hydroxy-7β-ethoxycarbonyl-4-aza-5α-androstan-3-one, which is then etherified and cyclopropanated by the procedure of Example 7D to give the title compound.

Example 22E

17β-cyclopropyloxy-3-oxo-4-aza-5α-androstane 7β-carboxylic acid

17β-Cyclopropyloxy-7β-ethoxycarbonyl-4-aza-5α-androstan-3-one from Example 22D or otherwise obtained is hydrolyzed by the procedure of Example 7C to give the title compound.

Example 23A

17β-cyclopropyloxy-7β-propyloxycarbonyl-4-aza-androst-5-en-3-one

In a manner analogous to the procedure reported in Baer, H. et al., *Can. J. Chem* 1991, 69, 1563–1574, 17β-cyclopropyloxy-7β-hydroxy-4-aza-androst-5-en-3-one (1.000 g, 2.895 mmol) from Example 20A or otherwise obtained is dissolved in pyridine (20 mL). Proprionic anhydride (20.0 mL, 156.0 mmol) is added, and the mixture is stirred at room temperature under nitrogen for 12 hours. At the end of the reaction time, the solution is diluted with CH$_2$Cl$_2$ (150 mL) and washed with water (2×100 mL), saturated aqueous NaHCO$_3$ (2×100 mL), water (100 mL) and brine (100 mL). The organic phase is then dried over MgSO$_4$, filtered and evaporated to dryness. The residue is purified by flash chromatography (1:1 EtOAc/CH$_2$Cl$_2$) to give the title compound.

Example 23B

17β-cyclopropyloxy-7β-propyloxycarbonyl-4-aza-5α-androstan-3-one

In a manner analogous to the procedure described in Example 23A, 17β-cyclopropyloxy-7β-hydroxy-4-aza-5α-androst-5-en-3-one, from Example 20B or otherwise obtained is transesterified into the title compound.

Example 24A

17β-tert-butyldimethylsilyloxy-7β-hydroxymethyl-4-tert-butyldimethylsilyl-4-aza-5α-androstan-3-one 7β-Ethoxycarbonyl-4-aza-5α-androstane-3,17-dione prepared in Example 22C or otherwise obtained is reduced similarly as in Example 20A to obtain 7β-ethoxycarbonyl-17β-hydroxy-4-aza-5α-androstan-3-one (17-alcohol). The 17-alcohol is then silylated as in Example 16A to give 17β-tert-butyldimethylsilyloxy-7β-ethoxycarbonyl-4-tert-butyldimethylsilyl-4-aza-5α-androstan-3-one (protected alcohol).

In a manner analogous to the procedure described in Jeanloz, R. W. & Walker, E., CarbohydrateRes. 1967, 4, 504, and Walker, E. *Chem. Soc. Rev.*, 1976, 5, 23–50, The protected alcohol synthesized above (3.000 g, 5.0674 mmol) is dissolved in THF (50 mL) and a lithium borohydride solution (2.0 M in THF; 5.50 mL, 11.0 mmol) is added under an inert atmosphere. After stirring 3 hours at room temperature, the reaction mixture is diluted with EtOAc (200 mL) and washed with brine (3×100 mL). The organic solution is dried over MgSO$_4$, filtered and evaporated to dryness. The residue is purified by flash chromatography (1:1:2 EtOAc/CH$_2$Cl$_2$/hexane) to give 17β-tert-butyldimethylsilyloxy-7β-hydroxymethyl-4-tert-butyldimethylsilyl-4-aza-5α-androstan-3-one.

Example 24B

17β-t-butyldimethylsilyloxy-4-t-butyldimethylsilyl-3-oxo-4-aza-5α-androstan-7β-carbaldehyde In a manner analogous to the procedure described in Inokuchi, T. et al., *J. Org. Chem.* 1990, 55, 462–466, 17β-tert-butyldimethylsilyloxy-7β-hydroxymethyl-4-tert-butyldimethylsilyl-4-aza-5α-androstan-3-one (2.000 g, 3.6365 mmol) prepared in Example 24A and 4-hydroxy-2,2,6,6-tetramethylpiperidinyloxy benzoate (4-Hydroxy-TEMPO benzoate; 0.0250 g, 0.0905 mmol) are dissolved in CH$_2$Cl$_2$ (70 mL) and combined with saturated NaHCO$_3$ (120 mL). The biphasic solution is chilled to 0° C. and sodium bromite (NaBrO$_2$, 1.700 g, 12.602 mmol) is added with vigorous stirring. After the bromite addition, the reaction mixture is allowed to warm to room temperature, and is stirred an additional 3 hours. The reaction is quenched with the dropwise addition of ethanol (1.00 mL, 17.04 mmol) and then the phases are separated. The aqueous phase is extracted with $CH_2Cl_2$ (2×50 mL) and the combined organic layers are washed with brine (2×75 mL). The organic solution is dried over $MgSO_4$, filtered, and evaporated to dryness. The reissue is purified by flash chromatography (1:1:2 EtOAc/$CH_2Cl_2$/hexane) to afford the title compound.

Example 24C

7β-(1-hydroxypropyl)-17β-t-butyldimethylsilyloxy-4-t-butyldimethylsilyl-4-aza-5α-androstan-3-one In a manner analogous to the procedure described in Yamamoto, Y & Tamada, J., *J. Am. Chem. Soc.* 1987, 109, 4395–4396, 17β-t-butyldimethylsilyloxy-4-t-butyldimethylsilyl-3-oxo-4-aza-5α-androstan-7β-carbaldehyde (1.000 g, 1.8250 mmol) prepared in Example 24B or otherwise obtained is dissolved in $CH_2Cl_2$ and cooled to −78° C. A solution of titanium tetrachloride ($TiCl_4$; 1.0 M in $CH_2Cl_2$; 2.20 mL, 2.20 mmol) and tetraethyl lead ($Et_4Pb$; 0.700 mL, 3.5775 mmol) are sequentially added. The reaction mixture is then allowed to gradually warm to to −30° C. over 30 minutes. The reaction is quenched, when the temperature reaches −30° C., with methanol (10 mL) and saturated aqueous $NaHCO_3$ (10 mL). The crude product solution is diluted with ethyl acetate (100 mL) and washed with saturated aqueous $NaHCO_3$ (2×50 mL) and brine (2×50 mL). The organic solution is dried over $MgSO_4$, filtered, and concentrated. Purification of the residue by flash chromatography (1:1:2 EtOAc/$CH_2Cl_2$/hexane) affords the title compound as a mixture of the $C_7$-a-diastereomers.

Example 24D

7β-(1-oxopropyl)-17β-t-butyldimethylsilyloxy-4-t-butyldimethylsilyl-4-aza-5α-androstan-3-one 7β-(1-Hydroxypropyl)-17β-t-butyldimethylsilyloxy-4-t-butyldimethylsilyl-4-aza-5α-androstan-3-one from Example 24C is oxidized in a manner as in Example 6D to obtain the title compound.

Example 24E

17β-cyclopropyloxy-7β-(1-oxopropyl)-4-aza-5α-androstan-3-one

7β-(1-Oxopropyl)-17β-t-butyldimethylsilyloxy-4-t-butyldimethylsilyl-4-aza-5α-androstan-3-one from Example 24D is desilylated as in Example 19C and etherified and cyclopropanated as in Example 7D to give the title compound. The compound has the following structural formula:

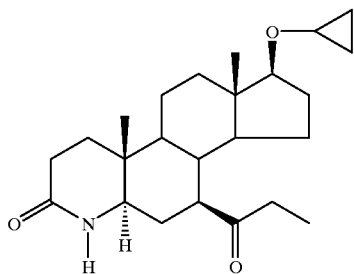

Example 25A

17β-acetoxy-7β-p-tolyl-4-aza-androst-5-en-3-one

Under an inert atmosphere, a slurry is made of magnesium turnings (2.500 g, 102.8 mmol) in THF (50 mL), followed by the addition of 4-bromotoluene (0.50 mL, 4.063 mmol). After the initiation of the Grignard reaction, a solution of 4-bromotoluene (10.75 mL, 87.363 mmol) in THF (100 mL) is added dropwise over 60 minutes while keeping the reaction temperature below the reflux temperature with a water bath. The Grignard solution is stirred an additional 14 hours at room temperature after adding the bromide solution, after which is added a solution of 3β-acetoxy-17β-tert-butyldimethylsilyloxy-androst-5-en-7-one (40.000 g, 86.821 mmol) prepared in Example 16B or otherwise obtained in THF (500 mL) while maintaining an inert atmosphere. The addition is allowed to occur over 24 hours at room temperature. The reaction is then poured into saturated aqueous $NH_4Cl$ (500 mL), the product extracted into EtOAc 3(×500 mL), washed with saturated aqueous $NaHCO_3$ (3×500 mL), brine (500 mL), dried over $MgSO_4$, filtered and concentrated to afford a crude mixture of 17β-tert-butyldimethylsilyloxy-7-p-tolyl-androst-5-ene-7,3β-diol diastereomers (diastereomers).

The diastereomer mixture prepared above is oxidized as in Example 16D to give 17β-tert-butyldimethylsilyloxy-7β-p-tolyl-androsta-4,6-dien-3β-one, which is then reduced (hydrogenated) as in Example 16E to give 17β-tert-butyldimethylsilyloxy-7β-p-tolyl-androst-5-en-3-one ($C_5$-olefin). The $C_5$-olefin is isomerized and desilylated as in Example 16F to give 17β-hydroxy-7β-p-tolyl-androst-4-en-3-one, which is converted into 17β-hydroxy-5-oxo-7β-p-tolyl-$^4$-nor-3,5-seco-androst-3-carboxylic acid as in Example 6A (seco-acid). The seco-acid is then converted into 17β-acetoxy-7β-p-tolyl-4-aza-androst-5-en-3-one.

Example 25B

17β-cyclopropyloxy-7β-p-tolyl-4-aza-androst-5-en-3-one

17β-Acetoxy-7β-p-tolyl-4-aza-androst-5-en-3-one from Example 26A is hydrolyzed as in Example 7C to give the corresponding 17-alcohol and this compound is etherified and cyclopropanated as in Example 7D to give the title compound.

Example 26A

17β-hydroxy-7β-p-tolyl-4-aza-5α-androstan-3-one

17β-Acetoxy-7β-p-tolyl-4-aza-androst-5-en-3-one is hydrogenated as in Example 6C to give 7β-acetoxy- 7β-p-tolyl-4-aza-5α-androstan-3-one, then hydrolyzed as in Example 7C to give the title compound.

Example 26B

17β-cyclopropyloxy-7β-p-tolyl-4-AZa-5α-androstan-3-one

17β-Hydroxy-7β-p-tolyl-4-aza-5α-androstan-3-one prepared in Example 26A is etherified and cyclopropanated as in Example 7D to give the title compound.

Example 26C

17β-cyclopropylamino-7β-p-tolyl-4-aza-5α-androstan-3-one 17β-Hydroxy-7β-p-tolyl-4-aza-5α-androstan-3-one prepared in Example 26A is $C_{17}$-oxidized and cycloaminated as in Examples 6D and 6E, respectively, to give the title compound.

Example 27

16β-propyl-4-aza-androstenes

Example 27A

16β-(2-propen-1-yl)-4-aza-androst-5-en-3,17-dione

Androst-4-ene-3,17-dione is oxidized into 5-oxo-4-nor-3, 5-seco-androstane-5,17-dione as in Example 16A (seco-acid). The seco-acid (9.000 g, 31.423 mmol) is slurried with methylammonium chloride (19.5000 g, 288.80 mmol) into acetic acid (75 mL) and heated to reflux under an inert atmosphere. After 3 days, the reaction mixture is allowed to cool to room temperature and diluted with ethyl acetate (EtOAc, 500 mL). The organic solution is washed with water (3×200 mL), saturated aqueous NaHCO$_3$ (2×200 mL) and brine (200 mL), then dried over magnesium sulfate (MgSO$_4$), filtered, concentrated and purified by flash chromatography (1:1:2 EtOAc/CH$_2$Cl$_2$) to afford 4-methyl-4-aza-androst-5-ene-3,17-dione (aza-dione).

By the procedure described in Carruthers, N. I. et al., *J. Org. Chem.* 1992, 57(3), 961–965, the aza-dione prepared above (3.000 g, 9.9529 mmol) is dissolved in CH$_2$Cl$_2$ (50 mL) and diethyl oxalate (1.50 mL, 11.04 mmol) and sodium methoxide (0.750 g, 13.88 mmol) are sequentially added. The reaction mixture is stirred for 60 minutes at 0° C. under nitrogen and a second charge of sodium methoxide (0.100 g, 1.851 mmol) is added. The reaction mixture is stirred another 30 minutes and a third charge of sodium methoxide (0.100 g, 1.851 mmol) and another portion of diethyl oxalate (0.30 mL, 2.209 mmol) are added. The reaction solution is allowed to warm to room temperature and is stirred under nitrogen for 16 hours. The solution is then evaporated to dryness and taken up in acetone (50 mL). The acetone solution is transferred to a 100 mL Ace Glass® pressure tube and treated with methyl iodide (3.50 mL, 56.22 mmol). The pressure tube is sealed and heated to 55° C. for 22 hours. At the end of this time, the pressure tube is cooled to 0° C. and carefully vented. The solvent and reagent are evaporated and the residue is slurried in methanol (50 mL) at 0° C., and sodium methoxide solution (25% in methanol; 2.25 mL, 10.14 mmol) is added to the cold methanolic steroid slurry. After stirring 90 minutes at 0°, the basic methanol slurry is poured into a 0° 0.5 M acetic acid solution (25.0 mL) with stirring, and the resultant precipitate is collected by filtration. The product is purified by flash chromatography to give 4-methyl-16β-(2-propen-1-yl)-4-aza-androst-5-ene-3,17-dione.

Example 27B

17β-cyclopropylamino-4-methyl-16β-(2-propen-1-yl)-4-aza-androst-5-en-3-one

4-Methyl-16β-(2-propenyl)-4-aza-androst-5-ene-3,17-dione prepared in Example 27A or otherwise obtained is cycloaminated as in Example 6E to give the title compound. The compound has the following formula:

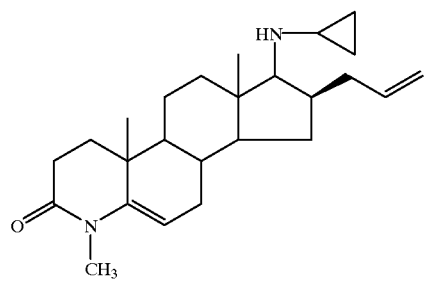

Example 27C

17β-cyclopropylamino-4-methyl-16β-(2-propen-1-yl)-4-aza-5α-androstan-3-one

17β-Cyclopropylamino-4-methyl-16β-(2-propen-1-yl)-4-aza-androst-5-en-3-one (0.500 g, 1.293 mmol) from Example 27B or otherwise obtained and palladium catalyst (5% Pd on C; 0.100 g, 0.940 mmol) are placed into a 500 mL Parr bottle under nitrogen. Ethanol (100 mL) is added to the reaction vessel, and the bottle is charged to 60 p.s.i. with H$_2$. The hydrogenation reaction is conducted at 60° C. with shaking in a Parr apparatus. After 5 days, the reaction mixture is filtered through Celite®, and the filtrate was evaporated to dryness. Purification by flash chromatography (1:1:2 EtOAc/CH$_2$Cl$_2$/hexane) gives the title compound.

Example 27D

17β-cyclopropyloxy-4-methyl-16β-(2-propen-1-yl)-4-aza-androst-5-en-3-one

4-Methyl-16β-(2-propen-1-yl)-4-aza-5α-androst-5-ene-3,17-dione prepared in Example 27A or otherwise obtained is reduced to give the C$_{17}$-alcohol as in Example 20A, and then etherified and cyclopropanated as in Example 7D to obtain the title compound.

Example 27E

17β-cyclopropyloxy-4-methyl-16β-(1-propyl)-4-aza-androst-5-en-3-one

17β-Cyclopropyloxy-4-methyl-16β-(2-propen-1-yl)-4-aza-androst-5-en-3-one prepared in Example 27D or otherwise obtained is reduced as in Example 27C to give the title compound.

Example 28

15β-ethyl-17β-cyclopropylamino-4-methyl-4-aza-androst-5en-3-one

Example 28A

16α-bromo-17,17-ethylenedioxy-androst-5-en-3β-ol 3-acetate

3β-Acetoxy-androst-5-en-17-one (dehydroisoandrosterone 3-acetate, ALDRICH 39,008-9) is ketalized as described in Example 18A to give 17,17-ethylenedioxy-androst-5-en-3β-ol 3-acetate (Cl$_7$-ketal). The C$_{17}$ ketal is dissolved into solution with dry THF (150 mL), and a solution of pyridinium bromide perbromide (ALDRICH 21,469-8, C$_5$H$_5$NH$^\oplus$Br$_3^{63}$; 88.000 g, 275.138 mmol) in dry THF (150 mL) is added under an inert atmosphere. The reaction mixture is stirred at ambient temperature for 2 hours, then treated with NaI (70.000 g, 467.01 mmol). The reaction solution is stirred for an additional 30 minutes, then treated with a mixture of sodium thiosulfate (Na$_2$S$_2$O$_3$, 95.000 g, 600.85 mmol) in a mixture of water (150 mL) and pyridine (35.0 mL, 432.7 mmol). The resulting solution is stirred at room temperature for another 3 hours. The reaction mixture is then diluted with water (300 mL) and THF is evaporated under reduced pressure. The precipitate which forms is collected by filtration and is recrystallized from ethanol to afford the title compound.

Example 28B 17,17-ethylenedioxy-androst-5,15(16)-dien-3β-ol

16α-Bromo-17,17-ethylenedioxy-androst-5-en-3β-ol 3-acetate from Example 28A (50.000 g, 110.28 mmol) is dissolved in dimethyl sulfoxide (DMSO; 500 mL) and the solution is warmed to 45° C. under an inert atmosphere. After 22 hours, the reaction is partitioned between ether

Example 28C

3β-t-butyldimethylsilyloxy-androst-5,15(16)-dien-17-one 17,17-Ethylenedioxy-androst-5,15(16)-dien-3β-ol from Example 28B or otherwise obtained is dissolved in acetone (500 mL) and water (60 mL) and the solution is cooled to 0° C. To the 0° C. solution is added p-toluenesulfonic acid monohydrate (1.000 g, 5.257 mmol). The 0° reaction mixture is stirred for 5 hours and then stored at 40° for 16 hours. The chilled reaction solution is diluted with water (300 mL) and acetone is evaporated under reduced pressure. The aqueous slurry remaining is extracted with EtOAc (2×300 mL) and the combined organic phases are washed with saturated aqueous NaHCO$_3$ (200 mL) and brine (200 mL), dried over MgSO$_4$, filtered and concentrated. The residue is purified by flash chromatography (1:1 EtOAc/CH$_2$Cl$_2$) to afford 3-hydroxy-androst-5,15(16)-dien-17-one (C$_3$-alcohol).

The C$_3$-alcohol prepared above is silylated as in Example 16A to give the title compound.

Example 28D

15β-ethyl-androst-4-ene-3,17-dione

Cuprous chloride (CuCl, 0.7611 g, 7.689 mmol) is slurried in THF (40 mL) under nitrogen and then chilled to −22° C. with a dry ice/tetrachloroethylene bath. Ethylmagnesium chloride solution (2.00 M in ether; 22.0 mL, 44.0 mmol) is added to the cold cuprous chloride slurry and the dark solution is stirred for 90 minutes. A solution of 3β-t-butyldimethylsilyloxy-androst-5,15-dien-17-one (from Example 28C;) in THF (50 mL) is added dropwise via polyethylene cannula to the organometallic solution over 10 minutes, followed by a THF rinse (20 mL). The reaction mixture is stirred for 2 hours at −22° C. and then allowed to warm to ambient temperature over 30 minutes, followed by addition of saturated aqueous NH$_4$Cl (50 mL). The biphasic mixture is extracted with EtOAc (2×40 mL) and the combined organic layers are washed with brine (50 mL), dried over MgSO$_4$, filtered and evaporated to dryness. Purification by flash chromatography gives 15β-ethyl-3β-t-butyldimethylsilyloxy-androst-5-en-17-one, which is deprotected as in Example 19C to give the corresponding 3-alcohol, which is then oxidized as in Example 16D to obtain the title compound, which has the following formula:

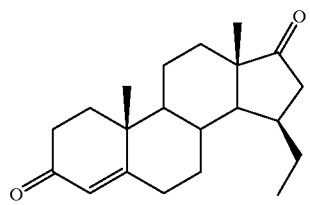

Example 28E

15β-ethyl-4-aza-androst-5-ene-3,17-dione

15β-Ethyl-androst-4-ene-3,17-dione from Example 28D or otherwise obtained is oxidized into 15β-ethyl-5,17-dioxo-4-nor-3,5-seco-androstane-3-carboxylic acid (seco-acid) as in Example 6A, which is then converted into 15β-ethyl-4-aza-androst-5-en-3,17-dione as in Example 6B.

Example 28F

15β-ethyl-17β-cyclopropylamino-4-aza-androst-5-en-3-one

15β-Ethyl-4-aza-androst-5-ene-3,17-dione is cycloaminated as in Example 6E to give the title compound.

Example 29

15-ethyl-17β-cyclopropyloxy-4-aza-androst-5-en-3-one

Example 29A

15β-ethyl-17β-hydroxy-4-aza-androst-5-en-3-one

15β-Ethyl-4-aza-androst-5-ene-3,17-dione is reduced as in Example 20A to give the title compound.

Example 29B

15β-ethyl-17β-cyclopropyloxy-4-aza-androst-5-en-3-one

15β-Ethyl-17β-hydroxy-4-aza-androst-5-en-3-one from Example 29A is etherified and cyclopropanated as in Example 7D to give the title compound.

Example 29C

15β-ethyl-17β-cyclopropyloxy-4-aza-5α-androst-3-one

15β-Ethyl-17β-hydroxy-4-aza-androst-5-en-3-one is hydrogenated as in Example 27C and then etherified and cyclopropanated as in Example 7D to give the title compound.

What is claimed is:

1. A compound, or a pharmaceutically acceptable salt thereof having the following formula:

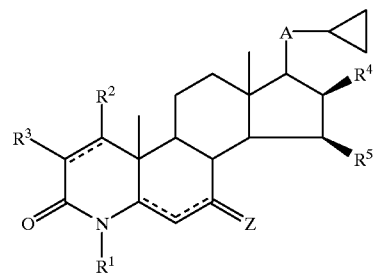

wherein:

A is O or NH;

R$^1$ is H or C$_{1-4}$ alkyl;

R$^2$ is H, halo, phenylthio, phenylsulfinyl or phenylsulfonyl;

R$^3$ is H, halo, C$_{1-4}$ alkylthio, C$_{1-4}$ alkylsulfinyl or C$_{1-4}$ alkylsulfonyl;

R$^4$ is H, C$_{1-4}$ alkyl or C$_{2-4}$ alkenyl;

R$^5$ is H or C$_{1-4}$ alkyl;

Z is:

(a) oxo; or (b) (H) (H) or an α-hydrogen and β-substituent selected from the group consisting of: $C_{1-4}$ alkyl, $C_{2-4}$ alkenyl, hydroxy, $C_{1-4}$ alkanoyloxy, $C_{1-4}$ alkoxycarbonylmethyl, carboxymethyl, $C_{1-4}$ alkoxycarbonyl, carboxy, $C_{1-4}$ alkanoyl and halo; with the proviso that when:

(a) $R^2$ is present and is other than hydrogen, a 1,2 double bond is present, or (b) Z is oxo, a 6,7 double bond is not present, or (c) $R^1$ is H or $C_{1-4}$ alkyl, and $R^2$, $R^3$, $R^4$, and $R^5$ are H, and Z is (H)(H), and no double bonds exist in any of the positions 1(2), 5(6) or 6(7), A is not NH, or (d) A is O, and Z is (H)(H), and $R^2$, $R^3$, $R^4$ and $R^5$ are H, $R^1$ is $C_{3-4}$ alkyl.

2. The compounds or a pharmaceutically acceptable salt thereof, according to claim 1 having the following formula:

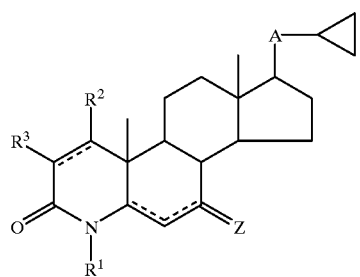

wherein:

A is O or NH;

$R^1$ is $C_{1-4}$ or alkyl;

$R^2$ is H or halo;

$R^3$ is H or halo; and

Z is (H) (H) or an α-hydrogen and β-substituent selected from the group consisting of: $C_{1-4}$ alkyl, $C_{1-4}$ alkoxycarbonylmethyl, and carboxymethyl.

3. The compound, or a pharmaceutically acceptable salt thereof, according to claim 2 having the following formula:

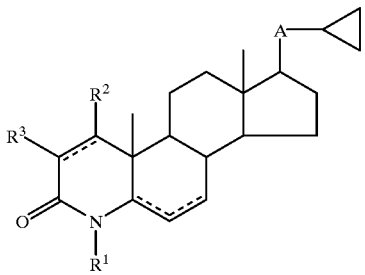

wherein:

A is O or NH;

$R^1$ is H or $C_{1-4}$ alkyl;

$R^2$ is H or fluoro.

4. A pharmaceutical composition having $C_{17-20}$ lyase and 5α-reductase activity comprising a pharmaceutical carrier and an effective inhibitory amount of a compound or a pharmaceutically acceptable salt thereof, of the formula:

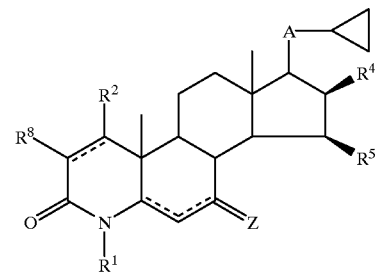

wherein:

A is O or NH;

$R^1$ is H or $C_{1-4}$ alkyl;

$R^2$ is H, halo, phenylthio, phenylsulfinyl or phenylsulfonyl;

$R^3$ is H, halo, $C_{1-4}$ alkylthio, $C_{1-4}$ alkylsulfinyl or $C_{1-4}$ alkylsulfonyl;

$R^4$ is H, $C_{1-4}$ alkyl or $C_{2-4}$ alkenyl;

$R^5$ is H or $C_{1-4}$ alkyl;

Z is:

(a) oxo;

(b) (H) (H) or an α-hydrogen and β-substituent selected from the group consisting of: $C_{1-4}$ alkyl, $C_{2-4}$ alkenyl, hydroxy, $C_{1-4}$ alkanoyloxy, $C_{1-4}$ alkoxycarbonylmethyl, carboxymethyl, $C_{1-4}$ alkoxycarbonyl, carboxy, $C_{1-4}$ alkanoyl and halo; with the proviso that when:

(a) $R^2$ is present and is other than hydrogen, a 1,2 double bond is present, or (b) Z is oxo, a 6,7 double bond is not present, or (c) $R^1$ is H or $C_{1-4}$ alkyl, and $R^2$, $R^3$, $R^4$, and $R^5$ are H, and Z is (H)(H), and no double bonds exist in any of the positions 1(2), 5(6) or 6(7), A is not NH, or (d) A is O, and Z is (H)(H), and $R^2$, $R^3$, $R^4$ and $R^5$ are H, $R^1$ is $C_{3-4}$ alkyl.

5. The pharmaceutical composition according to claim 4 having $C_{17-20}$ lyase and 5α-reductase activity comprising a pharmaceutical carrier and an effective inhibitory amount of a compound or a pharmaceutically acceptable salt thereof, of the formula:

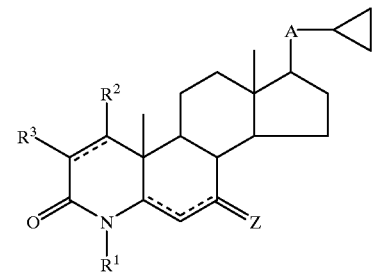

wherein:

A is O or NH;

$R^1$ is H or $C_{1-4}$ alkyl;

$R^2$ is H or halol; and $R^3$ is or halo; and Z is(H) (H) or an α-hydrogen and β-substituent selected from the group consisting of: $C_{1-4}$ alkoxycarbonylmethyl, and carboxymethyl.

6. The pharmaceutical composition according to claim 5 having $C_{17-20}$ lyase and 5α-reductase activity comprising a pharmaceutical carrier and an effective inhibitory amount of a compound or a pharmaceutically acceptable salt thereof, of the formula:

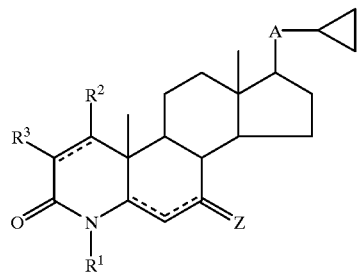

wherein:

A is O or NH;

$R^1$ is H or $C_{1-4}$ alkyl;

$R^2$ is H or fluoro.

7. A method for treating acne which comprises administering to a patient in need thereof an effective inhibitory amount of a compound or a pharmaceutically acceptable salt thereof, of the formula:

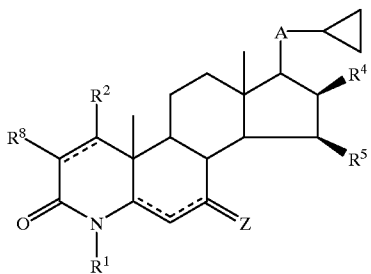

wherein:

A is O or NH;

$R^1$ is H or $C_{1-4}$ alkyl;

$R^2$ is H, halo, phenylthio, phenylsulfinyl or phenylsulfonyl;

$R^3$ is H, halo, $C_{1-4}$ alkylthio, $C_{1-4}$ alkylsulfinyl or $C_{1-4}$ alkylsulfonyl;

$R^4$ is H, $C_{1-4}$ alkyl or $C_{2-4}$ alkenyl;

$R^5$ is H or $C_{1-4}$ alkyl;

Z is:
  (a) oxo; or
  (b) (H)(H) or an α-hydrogen and β-substituent selected from the group consisting of: $C_{1-4}$ alkyl, $C_{2-4}$ alkenyl, hydroxy, $C_{1-4}$ alkanoyloxy, $C_{1-4}$ alkoxycarbonylmethyl, carboxymethyl, $C_{1-4}$ alkoxycarbonyl, carboxy, $C_{1-4}$ alkanoyl and halo;
with the proviso that when:
  (a) $R^2$ is present and is other than hydrogen, a 1,2 double bond is present, or
  (b) Z is oxo, a 6,7 double bond is not present, or
  (c) $R^1$ is H or $C_{1-4}$ alkyl, and $R^2$, $R^3$, $R^4$, and $R^5$ are H, and Z is (H)(H), and no double bonds exist in any of the positions 1(2), 5(6) or 6(7), A is not NH,
  (d) A is O, and Z is (H)(H), and $R^2$, $R^3$, $R^4$ and $R^5$ are H, $R^1$ is $C_{3-4}$ alkyl.

8. The method according to claim 7 for treating acne which comprises administering to a patient in need thereof an effective inhibitory amount of a compound or a pharmacutically acceptable salt thereof, of the formula:

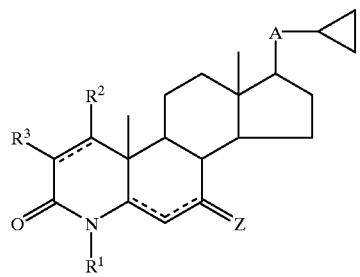

wherein:

A is O or NH;

$R^1$ is H or $C_{1-4}$ alkyl;

$R^2$ is H or halo;

$R^3$ is H or halo; and

Z is (H)(H) or an α-hydrogen and β-substituent selected from the group consisting of: $C_{1-4}$ alkyl, $C_{1-4}$ alkoxycarbonylmethyl, and carboxymethyl.

9. A method according to claim 8 for treating acne which comprises administering to a patient in need thereof an effective inhibitory amount of a compound or a pharmaceutically acceptable salt thereof, of the formula:

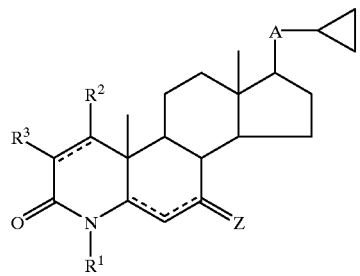

wherein:

A is O or NH;

$R^1$ is H or $C_{1-4}$ alkyl;

$R^2$ is H or fluoro.

10. The method according to claim 9 wherein the compound administered has the formula:

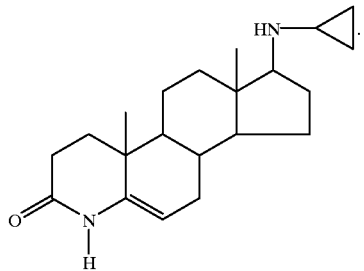

* * * * *

UNITED STATES PATENT AND TRADEMARK OFFICE
CERTIFICATE OF CORRECTION

PATENT NO. : 6,365,597 B1
DATED : April 2, 2002
INVENTOR(S) : James R. Pribish, Cynthia A. Gates and Philip M. Weintraub It is certified that error appears in the above-identified patent and that said Letters Patent is hereby corrected as shown below:

Column 2,
Line 3, reads "ediated", and should read -- mediated --.

Column 3,
Line 8, reads "a-hydrogen" should read -- α-hydrogen --.
Line 16, reads "6, 7, double", and should read -- 6, 7 double --.

Column 4,
Line 28, reads "or example", and should read -- For example --.

Column 9,
Line 50, reads "illustrate", and should read -- illustrates --.

Columns 11,
Scheme C, compound 14, the $C_{5-6}$ double bond should be a $C_{5-6}$ single bond.

Column 12,
Line 62, reads "The", and should read -- the --.

Column 15,
Line 66, reads "[14]", and should read -- [24] --.

Column 16,
Line 14, reads "[14]", and should read -- [24] --.

Columns 17-18,
Scheme F, reads

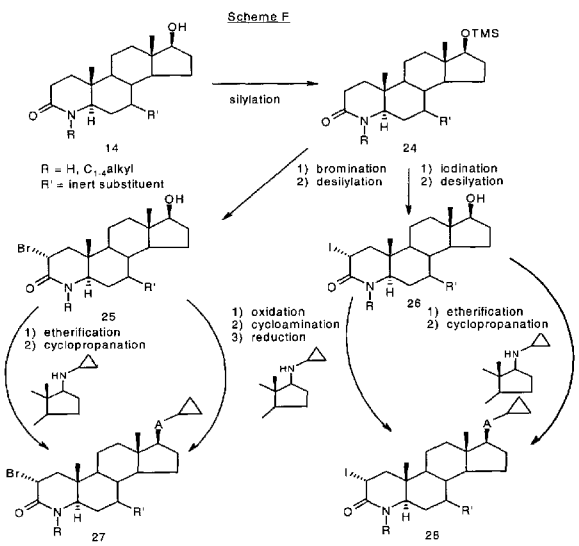

UNITED STATES PATENT AND TRADEMARK OFFICE
CERTIFICATE OF CORRECTION

PATENT NO. : 6,365,597 B1
DATED : April 2, 2002
INVENTOR(S) : James R. Pribish, Cynthia A. Gates and Philip M. Weintraub It is certified that error appears in the above-identified patent and that said Letters Patent is hereby corrected as shown below:

and
Columns 17-18,
Scheme F, should read

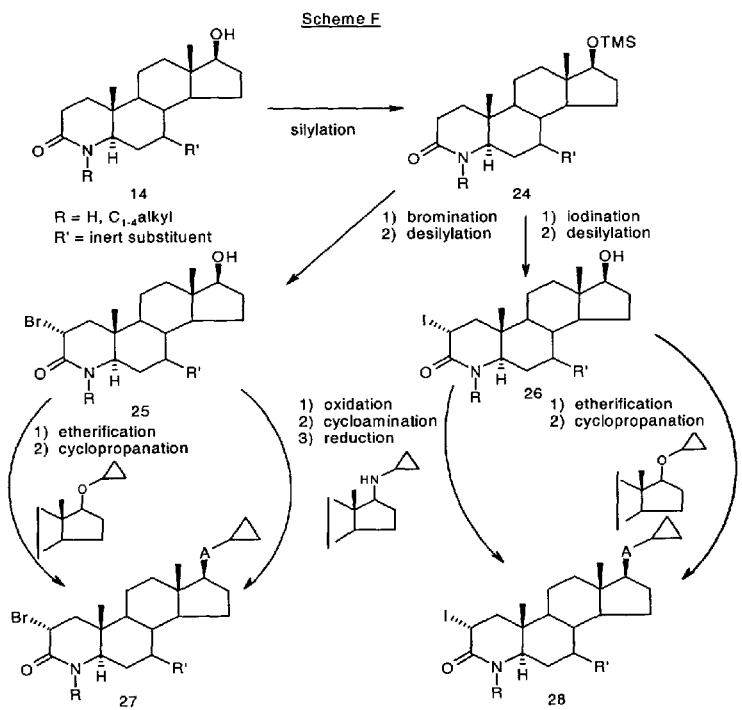

Column 21,
Scheme $H_2$, compound 38,

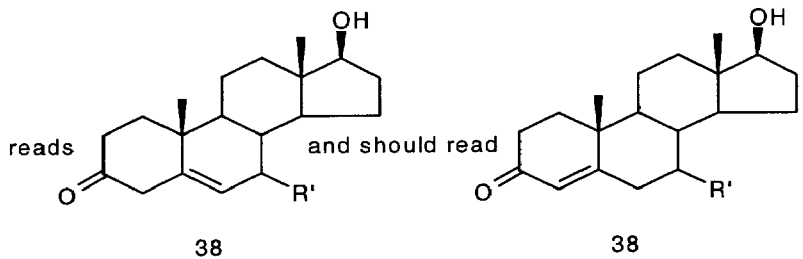

UNITED STATES PATENT AND TRADEMARK OFFICE
CERTIFICATE OF CORRECTION

PATENT NO. : 6,365,597 B1  Page 3 of 6
DATED : April 2, 2002
INVENTOR(S) : James R. Pribish, Cynthia A. Gates and Philip M. Weintraub It is certified that error appears in the above-identified patent and that said Letters Patent is hereby corrected as shown below:

Column 26,
Scheme I, compound 47, the $C_{5-6}$ double bond should be a $C_{5-6}$ single bond.

Column 33,
Scheme M, below the Option B arrow, the partial structure reads

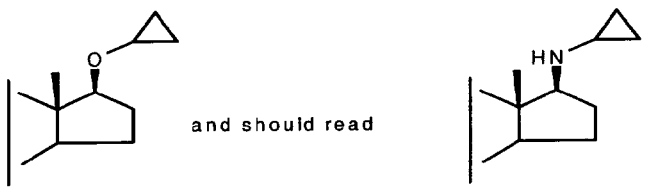

and should read

Column 37,
Scheme $O_1$, compound 80, the $C_{15-16}$ double bond should be a $C_{15-16}$ single bond.

Column 39,
Line 46, reads "Carboxy and Methyl Carboxy", and should read -- carboxy and methyl carboxy --.

Columns 39-40,
Scheme $O_2$, compound 84, reads

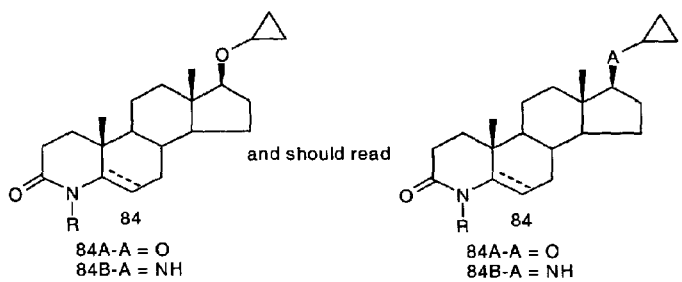

and should read

Column 42,
Line 60, reads "7%", and should read -- 7.5% --.

UNITED STATES PATENT AND TRADEMARK OFFICE
CERTIFICATE OF CORRECTION

PATENT NO. : 6,365,597 B1
DATED : April 2, 2002
INVENTOR(S) : James R. Pribish, Cynthia A. Gates and Philip M. Weintraub It is certified that error appears in the above-identified patent and that said Letters Patent is hereby corrected as shown below:

Column 44,
Line 28, reads "41:6070-5075", and should read -- 41:5070-5075 --.
Line 35, reads "5001]", and should read -- 5001 --.

Column 45,
Lines 11 and 12, reads "10583", and should read -- 105831 --.
Table 4, last column heading, reads "(day 35± day 0)", and should read -- (day 35-day 0) --.

Column 47,
Line 52, reads "chared", and should read -- charged --.

Column 48,
Line 26, reads "androstane-3-arboxylic acid", and should read -- androstane-3-carboxylic acid --.
Line 47, reads "residue in", and should read -- residue is --.

Column 49,
Line 65, reads "HOAC$_3$", and should read -- HOAc --.

Column 52,
Line 14, reads "vinyloxy-androstan-3-one", and should read -- hydroxy-androstan-3-one --.

Column 54,
Line 14, reads "(CH$_3$CH$_2$CHCH$_2$,", and should read -- (CH$_3$CH$_2$OCHCH$_2$, --.
Line 53, reads "NH$_4$CO", and should read -- NH$_4$Cl --.

Column 63,
Line 34, reads "17β-Cyclopropyloxy-4-methyl-l-phenylthio-4-aza-5α-", and should read -- 17β-Cyclopropyloxy-4-methyl-1β-phenylthio-4-aza-5α- --.
Line 64, reads "dries", and should read -- dried --.

Column 64,
Line 25, reads "cyclomaminated", and should read -- cycloaminated --.

UNITED STATES PATENT AND TRADEMARK OFFICE
CERTIFICATE OF CORRECTION

PATENT NO. : 6,365,597 B1
DATED : April 2, 2002
INVENTOR(S) : James R. Pribish, Cynthia A. Gates and Philip M. Weintraub It is certified that error appears in the above-identified patent and that said Letters Patent is hereby corrected as shown below:

Column 67,
Line 2, reads "to give to give", and should read -- to give --.

Column 68,
Lines 1-2, reads "to give the title compound to afford the title compound.", and should read -- to give the title compound. --.

Column 69,
Line 3, reads "5α-androstant-3-one", and should read -- 5α-androstan-3-one --.
Line 6, reads "androstant-3-one", and should read -- androstan-3-one --.

Column 70,
Line 48, reads "*Org. Synth. Cell Vol. Vi*", and should read -- *Org. Synth. Coll. Vol. VI* --.

Column 72,
Line 26, reads "17β-cyclopropylamino-7α-ethyl-" should read
-- 17β-cyclopropylamino-7β-ethyl- --.
Line 39, reads "7,7-ethylenedioxy-17β-t-butyldimethylsilylyoxy-" should read -- 7,7-ethylenedioxy-17β-t-butyldimethylsilyloxy- --.
Line 65, reads "7,7-Ethylenedioxy-17β-t-butyldimethylsilylyoxy- ", and should read --7,7-Ethylenedioxy-17β-t-butyldimethylsilyloxy- --.

Column 73,
Line 1, reads "7,7-ethylenedioxy-17β-t-butyldimethylsilylyoxy- ", and should read -- 7,7-ethylenedioxy-l7β-t-butyldimethylsilyloxy- --.
Line 3, reads "butyldimethylsilylyoxy-", and should read -- butyldimethylsilyloxy- --.
Line 35, reads "17β-Cyclopropylamino-4-aza-androst-5-diene-3,7-dione", and should read -- 17β-Cyclopropylamino-4-aza-androst-5-ene-3,7-dione --.

Column 74,
Line 14, reads "7-(t-butyldimethylsilyloxy)-4-trimethylsilyloxy-17β-", and should read --7-(t-butyldimethylsilyloxy)-4-trimethylsilyl-17β- --.
Line 16, reads "androst-5,7-en-3-one", and should read -- androst-5,7-diene-3-one --.
Line 61, reads "4-aza-7-hydroxy/7-oxo-androstene", and should read -- 4-aza-7β-hydroxy/7-oxo-androstene --.

UNITED STATES PATENT AND TRADEMARK OFFICE
CERTIFICATE OF CORRECTION

PATENT NO. : 6,365,597 B1
DATED : April 2, 2002
INVENTOR(S) : James R. Pribish, Cynthia A. Gates and Philip M. Weintraub It is certified that error appears in the above-identified patent and that said Letters Patent is hereby corrected as shown below:

Column 79,
Line 6, reads "reissue", and should read -- residue --.
Line 30, reads "$C_7$-a-diastereomers.", and should read -- $C_7$-α-diastereomers. --.

Column 81,
Line 10, reads "(1:1:2 EtOAc/$CH_2CH_2$)", and should read --(1:1:2 EtOAc/$CH_2C_2$/hexane) --.

Column 83,
Line 16, reads "40°", and should should read -- 4° --.

Column 85,
Line 16, reads "The compounds", and should read -- The compound --.
Line 35, reads "$R^1$ is $C_{1-4}$ or alkyl;", and should read -- $R^1$ is H or $C_{1-4}$ or alkyl; --.

Column 86,
Lines 1-14, the chemical formula $C_2$ substituent reads as "$R^8$" and should read as -- $R^3$ --.
Line 62, reads "$R^2$ is H or halol; and", and should read -- $R^2$ is H or halo; and --.
Line 63, reads "$R^3$ is or halo;", and should read -- $R^3$ is H or halo; --.

Column 87,
Lines 26-38, the chemical formula $C_2$ substituent reads as "$R^8$" and should read as -- $R^3$ --.

Signed and Sealed this

Nineteenth Day of August, 2003

JAMES E. ROGAN
*Director of the United States Patent and Trademark Office*